US012281060B2

(12) United States Patent
Solway et al.

(10) Patent No.: US 12,281,060 B2
(45) Date of Patent: Apr. 22, 2025

(54) REMODILINS FOR AIRWAY REMODELING AND ORGAN FIBROSIS

(71) Applicants: The University of Chicago, Chicago, IL (US); The United States of America, as Represented by the Secretary, Department of Health and Human Services, Bethesda, MD (US); President and Fellows of Harvard College, Cambridge, MA (US); IIT Research Institute, Chicago, IL (US); Beth Israel Deaconess Medical Center, Inc., Boston, MA (US); REGENTS OF THE UNIVERSITY OF MINNESOTA, Minneapolis, MN (US); THE TRUSTEES OF PURDUE UNIVERSITY, Lafayette, IN (US)

(72) Inventors: Julian Solway, Glencoe, IL (US); Nickolai Dulin, Chicago, IL (US); Diane Luci, Germantown, MD (US); David Maloney, Point of Rocks, MD (US); Chan Young Park, Belmont, MA (US); Jeffrey Fredberg, Newton, MA (US); David McCormick, Chicago, IL (US); Ramaswamy Krishnan, Boston, MA (US)

(73) Assignees: The University of Chicago, Chicago, IL (US); The United States of America, as Represented by the Secretary, Department of Health and Human Services, Bethesda, MD (US); President and Fellows of Harvard College, Cambridge, MA (US); IIT Research Institute, Chicago, IL (US); Beth Israel Deaconess Medical Center Inc., Boston, MA (US)

( * ) Notice: Subject to any disclaimer, the term of this patent is extended or adjusted under 35 U.S.C. 154(b) by 24 days.

(21) Appl. No.: 17/594,086

(22) PCT Filed: Apr. 2, 2020

(86) PCT No.: PCT/US2020/026371
§ 371 (c)(1),
(2) Date: Oct. 1, 2021

(87) PCT Pub. No.: WO2020/206109
PCT Pub. Date: Oct. 8, 2020

(65) Prior Publication Data
US 2022/0177422 A1  Jun. 9, 2022

Related U.S. Application Data

(60) Provisional application No. 62/827,980, filed on Apr. 2, 2019.

(51) Int. Cl.
| | |
|---|---|
| C07D 311/46 | (2006.01) |
| A61P 11/00 | (2006.01) |
| C07C 311/46 | (2006.01) |
| C07D 207/48 | (2006.01) |
| C07D 211/96 | (2006.01) |
| C07D 277/52 | (2006.01) |
| C07D 295/26 | (2006.01) |

(52) U.S. Cl.
CPC ............. *C07C 311/46* (2013.01); *A61P 11/00* (2018.01); *C07D 207/48* (2013.01); *C07D 211/96* (2013.01); *C07D 277/52* (2013.01); *C07D 295/26* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 4,025,508 A | 5/1977 | Perrault | |
| 5,512,563 A * | 4/1996 | Albright | ............... C07D 513/04 514/217 |
| 6,506,936 B1 | 1/2003 | Ho | |
| 7,417,058 B2 | 8/2008 | Halazy et al. | |

(Continued)

FOREIGN PATENT DOCUMENTS

| | | | |
|---|---|---|---|
| WO | 0127084 A1 | | 4/2001 |
| WO | WO 2005/013914 | * | 2/2005 |

(Continued)

OTHER PUBLICATIONS

"N-[4-(Azepan-1-ylsulfonyl)phenyl]-3-iodo-4-methoxybenzamide" Pubchem, Sep. 26, 2005, https://pubchem.ncbi.nlm.nih.gov/compound/5186271. Accessed Jul. 27, 2020.
"N-[4-(Diethylsu Ifamoly)phenyl]-4-methoxybenzamide." Pubchem, Jul. 9, 2005, https://pubchem.ncbi.nlm.nih.giv/compound/1010395. Accessed Jul. 27, 2020.
International Search Report and Written Opinion issued in Corresponding PCT Application No. PCT/US2020/026371, dated Aug. 17, 2020.

(Continued)

*Primary Examiner* — Craig D Ricci
(74) *Attorney, Agent, or Firm* — Norton Rose Fulbright US LLP

(57) ABSTRACT

Disclosed herein is a class of molecules termed remodilins that are effective in treating asthma, pulmonary fibrosis, and associated disorders. The molecules ameliorate asthma and pulmonary fibrosis symptoms by various mechanisms, including inhibiting airway smooth muscle contractile protein accumulation, reducing airway constrictor hyperresponsiveness, inhibiting bronchial fibroblast transformation into myofibroblasts, and/or treating or preventing airway or pulmonary fibrosis.

3 Claims, 11 Drawing Sheets

(56) References Cited

U.S. PATENT DOCUMENTS

| | | | |
|---|---|---|---|
| 8,153,803 B2* | 4/2012 | Kazantsev | C07D 405/12 546/171 |
| 8,299,096 B2 | 10/2012 | Navratil et al. | |
| 2006/0041006 A1 | 2/2006 | Ibrahim et al. | |
| 2008/0090788 A1 | 4/2008 | Packham et al. | |
| 2013/0274215 A1 | 10/2013 | Thies et al. | |
| 2014/0271955 A1* | 9/2014 | Schultz | C07C 233/81 514/452 |

FOREIGN PATENT DOCUMENTS

| WO | 2005037257 A2 | 4/2005 |
|---|---|---|
| WO | WO 2010/125831 | 11/2010 |
| WO | 2018112077 A1 | 6/2018 |

OTHER PUBLICATIONS

Turtle, et al.: "Design and synthesis of procollagen C-proteinase inhibitors," Bioorganic & Medicinal Chemistry Letters 22 (2012), pp. 7397-7401.

Supplementaty European Search Report and Opinion ssued on Jul. 6, 2023 in the corresponding Patent Application No. 20783111.6-1112.

* cited by examiner

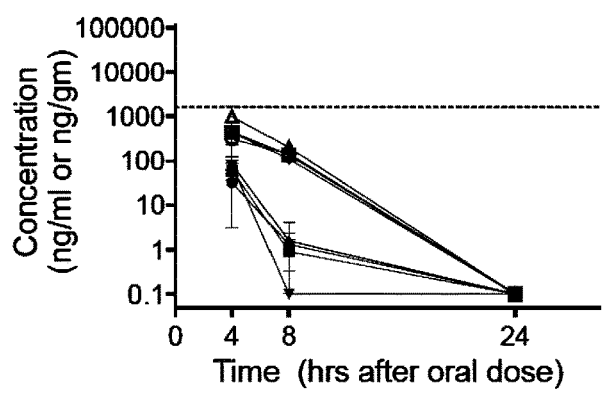 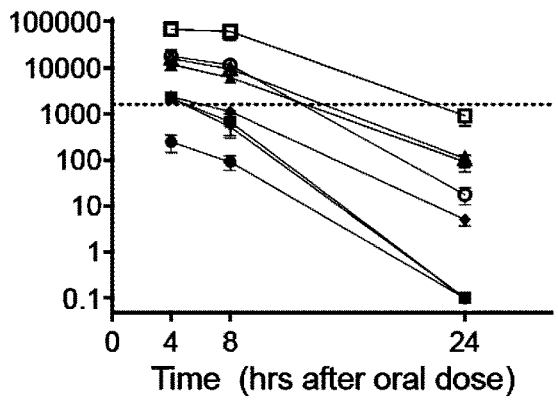
FIG. 3A  FIG. 3B
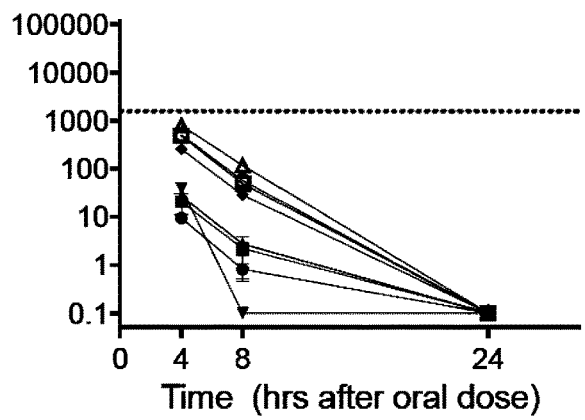 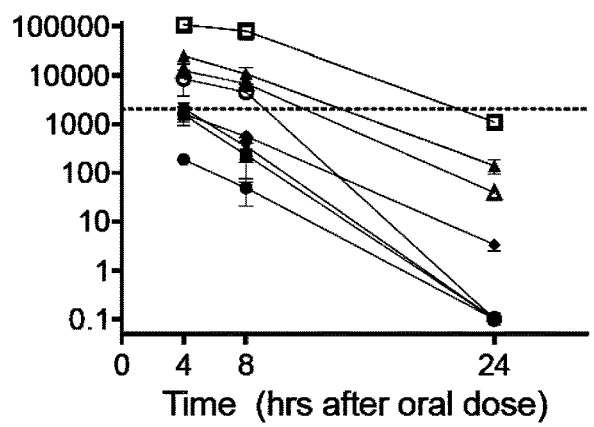
FIG. 3C  FIG. 3D
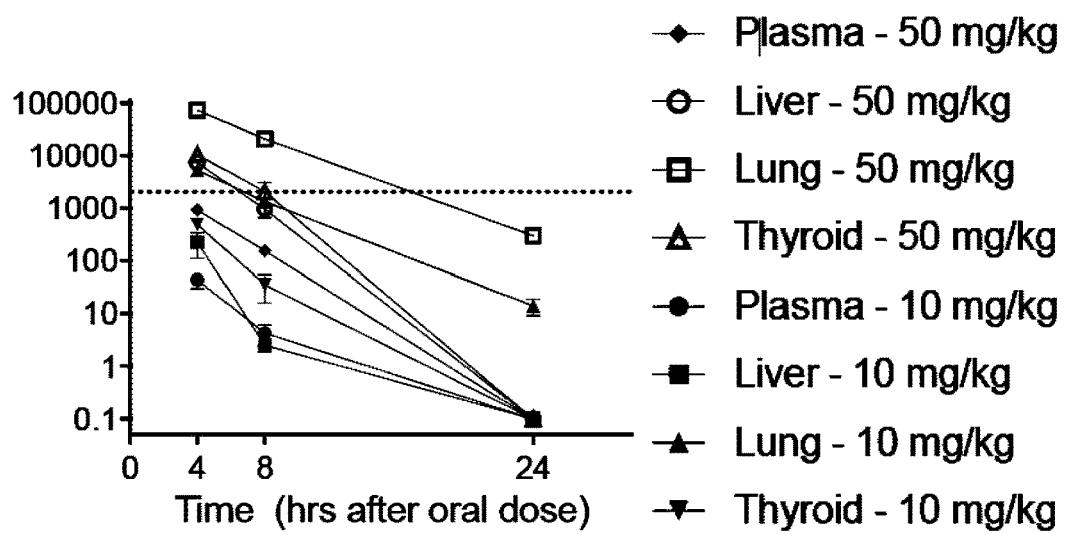
FIG. 3E

| Remodilin 39 ΔTm | P-value | Remodilin 83 ΔTm | P-value | Protein ID | Description |
|---|---|---|---|---|---|
| 1.36693526 | 0.00011494 | 2.28907804 | 0.00526134 | O14974 | Protein phosphatase 1 regulatory subunit 12A |
| 1.59914948 | 0.00828163 | -3.4898662 | 0.01538857 | O75494 | Serine/arginine-rich splicing factor 10 |
| 1.48585247 | 0.02402668 | 1.07907846 | 0.04529971 | O75935 | Dynactin subunit 3 |
| 0.97254759 | 0.00977301 | 1.85820773 | 0.00225864 | O94979 | Protein transport protein Sec31A |
| 5.01041444 | 0.00032693 | 2.22680366 | 0.03720002 | O95816* | BAG family molecular chaperone regulator 2 |
| 1.71013027 | 0.01330618 | -1.718215 | 0.02030068 | P04181 | Ornithine aminotransferase, mitochondrial |
| -0.8316286 | 0.00404044 | 1.57374239 | 7.6649E-5 | P08133 | Annexin A6 |
| 5.33118325 | 0.02547683 | 5.28373818 | 0.03329544 | P12110* | Collagen alpha-2(VI) chain |
| 1.75927318 | 0.04474579 | 3.4281037 | 0.00088319 | P30101 | Protein disulfide-isomerase A3 |
| 1.54185298 | 0.03652786 | 2.12177211 | 0.03308594 | P31689 | DnaJ homolog subfamily A member 1 |
| 0.96922371 | 0.04438623 | 1.86546614 | 0.00015984 | P31943 | Heterogeneous nuclear ribonucleoprotein H |
| 0.67741767 | 0.02790203 | 0.98507753 | 0.0024232 | P34932 | Heat shock 70 kDa protein 4 |
| -3.907456 | 0.000914969 | -2.1624199 | 0.00336515 | P46778* | 60S ribosomal protein L21 |
| 0.5793648 | 0.01807197 | 0.69114913 | 0.01275466 | P49327 | Fatty acid synthase |
| 0.45192241 | 0.00140696 | 0.64164321 | 0.00831253 | Q04637 | Eukaryotic translation initiation factor 4 gamma 1 |
| 2.31174497 | 0.03558715 | 2.06039532 | 0.0263984 | Q13492* | Phosphatidylinositol-binding clathrin assembly protein |
| 1.36713268 | 0.02690534 | 1.51534656 | 0.03179997 | Q13561 | Dynactin subunit 2 |

FIG. 10A

| Remodilin 39 ΔTm | P-value | Remodilin 83 ΔTm | P-value | Protein ID | Description |
|---|---|---|---|---|---|
| 2.5593559 | 0.04710309 | 6.6652219 | 0.00478595 | Q14554* | Protein disulfide-isomerase A5 |
| 0.99633677 | 0.00776293 | 5.11944526 | 0.00053581 | Q14697 | Neutral alpha-glucosidase AB |
| 2.32080869 | 0.02088582 | 3.70822822 | 0.00365012 | Q15121* | Astrocytic phosphoprotein PEA-15 |
| 0.99882288 | 0.03414793 | 1.45786531 | 0.0120523 | Q15365 | Poly(rc)-binding protein 1 |
| 0.59847746 | 0.02499562 | 1.48857452 | 0.00055879 | Q15366 | Poly(rC)-binding protein 2 |
| 2.76838212 | 0.00950603 | -2.1047092 | 0.02481098 | Q2M389 | WASH complex subunit 7 |
| -1.2898215 | 0.01881109 | 1.96317158 | 0.0304049 | Q7L2H7 | Eukaryotic translation initiation factor 3 subunit M |
| 2.38442058 | 0.03459073 | 3.86489856 | 0.01910752 | Q96HC4* | PDZ and LIM domain protein 5 |
| 5.01634633 | 0.01094827 | -3.8455513 | 0.04831903 | Q9BS18 | Anaphase promoting complex subunit 13 |
| 0.59280744 | 0.03545428 | 2.17198092 | 6.7626 E-05 | Q9NR12 | PDZ and LIM domain protein 7 |
| 0.75095449 | 0.00168212 | 1.13976775 | 0.00073897 | 09Y490 | Talin-1 |

FIG. 10B

REMODILINS FOR AIRWAY REMODELING AND ORGAN FIBROSIS

CROSS-REFERENCE TO RELATED APPLICATIONS

This application is a national phase application under 35 U.S.C. § 371 of International Application No. PCT/US2020/026371 filed Apr. 2, 2020, which claims the benefit of priority of U.S. Provisional Patent Application No. 62/827,980 filed Apr. 2, 2019, all of which are hereby incorporated by reference in their entirety.

This application is related by subject matter to U.S. Provisional Patent Application No. 62/828,122 filed Apr. 2, 2019, entitled Remodilins to Prevent or Treat Cancer Metastasis, Glaucoma, and Hypoxia by Julian Solway et al., which is incorporated by reference.

STATEMENT OF GOVERNMENT SUPPORT

This invention was made with government support under grant numbers HL 123816, HL120839, HL107171, awarded by the National Institutes of Health. The government has certain rights in the invention.

FIELD OF THE INVENTION

The present invention relates generally to the fields of medicine, medicinal chemistry, organic chemistry, and pharmacology.

BACKGROUND

Asthma is a common chronic disorder of the airways that involves a complex interaction of airflow obstruction, airway constrictor hyperresponsiveness, airway remodeling, and underlying inflammation. In asthma, the dominant physiological event leading to clinical symptoms is airway narrowing and subsequent restriction of airflow.

Airway constrictor hyperresponsiveness—an exaggerated bronchoconstrictor response to a wide variety of stimuli—is a major feature of asthma. There are multiple mechanisms that influence airway constrictor hyperresponsiveness, including inflammation and airway structural changes. Airway constrictor hyperresponsiveness is a basis for the variable airflow obstruction associated with many of the day-to-day symptoms of asthma, including those associated with exercise-induced asthma, nocturnal asthma, and asthma exacerbation induced by fumes or cold air.

In some cases of asthma, permanent airway remodeling occurs and leads to progressive loss of lung function that is not prevented by or fully reversible by current therapies. Airway remodeling involves activation of various airway structural cell types, with permanent airway changes that impede airflow and impair airway responsiveness, thereby rendering the patient less responsive to therapy. These structural changes can include fibrosis, thickening of the sub-epithelial basement membrane, airway smooth muscle hypertrophy and hyperplasia, blood vessel proliferation and dilation, and mucous gland hyperplasia and hypersecretion.

Excessive accumulation of airway smooth muscle, through hypertrophy and/or hyperplasia, is a principal contributor to airway hyperresponsiveness and excessive luminal narrowing during asthma attacks. Excessive accumulation of smooth muscle and vascular wall scarring also contribute to the development and worsening of pulmonary hypertension and pulmonary vascular remodeling. Because of its important role in asthma pathogenesis, inhibition of its contraction (for example using beta-2 adrenergic agonists) has been a mainstay of asthma therapy. Even destruction of airway smooth muscle (for example using bronchial thermoplasty) has found a role in asthma treatment. However, no previous therapies have been designed to inhibit the ability of airway smooth muscle to contract by depleting it of its contractile apparatus proteins.

Fibrosis is another of the key pathological features of airway remodeling in asthma. In the normal airway, the amount of collagen and other extracellular matrix components is kept in equilibrium by regulation of synthesis and degradation. In asthma, this homeostasis is disrupted, and there is excessive accumulation of airway smooth muscle contractile proteins, and extracellular matrix deposition. In idiopathic pulmonary fibrosis (IPF) there is progressive lung scarring effected by fibroblasts that have undergone TGFβ-driven transformation to the pro-fibrotic myofibroblast phenotype. These pathological abnormalities contribute to airway constrictor hyperresponsiveness and fixed airflow obstruction. Because myofibroblast transformation (MFT) represents a critical pathogenic step without which lung fibrosis would not occur, inhibition of MFT represents an attractive therapeutic strategy.

The lung scarring that occurs in idiopathic pulmonary fibrosis and other diseases in which lung scarring plays a critical pathogenic role (such as collagen vascular disease-related lung fibrosis, radiation-induced lung fibrosis, etc.) is poorly treated with current medications. There is therefore an unmet need in the field for improved treatment of these diseases. Presently, no medications directly target transformation of the fibroblast to the fibrosis-producing myofibroblast phenotype. Medications that prevent myofibroblast transformation could be useful in the treatment of lung diseases characterized by fibrosis. Such medications could also be useful in the treatment of diseases outside the lung, in which fibrosis plays an important pathogenic role. Examples include, but are not limited to, diseases of the liver, heart, kidney, and skin.

Many asthma treatments involve administration of corticosteroids or biologicals that target inflammation. Presently, however, no asthma treatments operate by targeting associated disorders like airway smooth muscle remodeling or airway fibrosis. There is therefore a need in the field for asthma therapeutics that can target one or more asthma-related disorders, including airway remodeling, bronchial contractile protein accumulation, myofibroblast transformation, airway fibrosis, and airway constrictor hyperresponsiveness.

SUMMARY OF THE INVENTION

The present disclosure provides compositions and methods for addressing the asthma- and fibrosis-associated pathophysiologies discussed above. The inventors have identified a series of novel small organic compounds, referred to herein as remodilins, that are useful for the treatment of asthma, fibrosis, and associated disorders discussed above. The inventors have discovered that these novel remodilins inhibit accumulation of contractile apparatus proteins (smooth muscle myosin heavy chain and smooth muscle alpha actin) in cultured human airway smooth muscle cells and inhibit transformation of cultured human lung or bronchial fibroblasts into the fibrosis-promoting myofibroblast phenotype. By affecting some of the underlying disorders associated with asthma and fibrosis, the remodilins provide methods and compositions ameliorating symptoms of asthma and associated disorders, including pulmonary fibrosis and fibrosis affecting organs outside the lung.

Certain aspects of the disclosure are directed towards compositions comprising a compound of Formula I:

Formula I

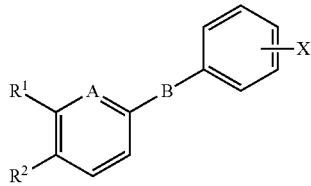

where A is —CH— or —N—, B is —C(O)—NH—, —NH—C(O)—, —CH₂—NH—, or —C(NH)—NH—, X is —(Y)—NR³R⁴ or NHSO₂Me, Y is —SO²—, —C(O)—, or —(CH₂)—, R¹ and R² are each independently hydrogen, hydroxyl, substituted or unsubstituted alkyl, substituted or unsubstituted alkynyl, alkoxy, halide, nitrile, amine, acylamine, substituted or unsubstituted aryl, 4-6 member carbocycle, substituted or unsubstituted heterocycle, and R³ and R⁴ are each independently hydrogen, substituted or unsubstituted alkyl, substituted or unsubstituted aromatic, substituted or unsubstituted carbocycle, substituted or unsubstituted heterocycle, substituted or unsubstituted bicyclic, or may join to form a carbocycle or heterocycle. In some embodiments, the compound is further defined as:

1

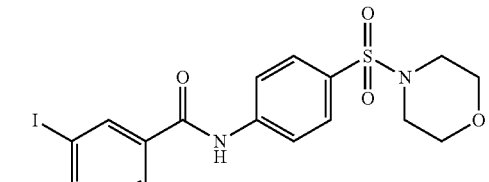

2

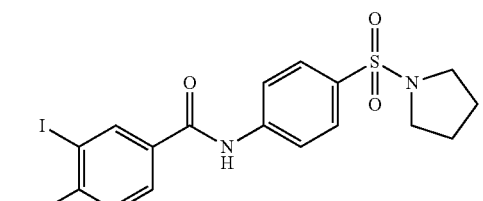

3

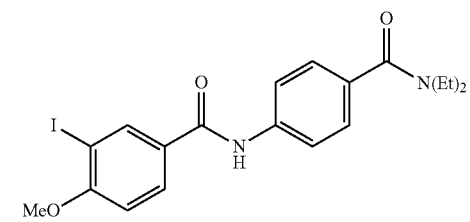

4

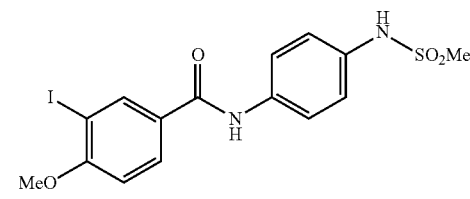

-continued

5

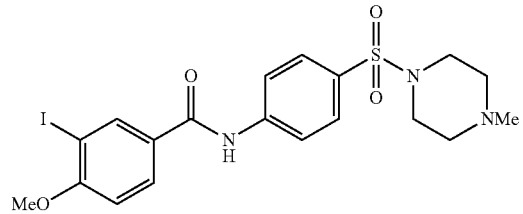

6

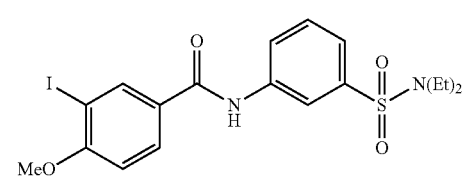

7

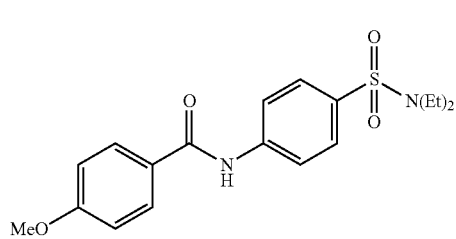

8

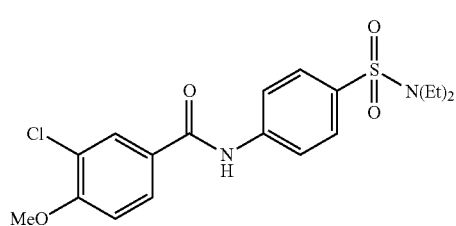

9

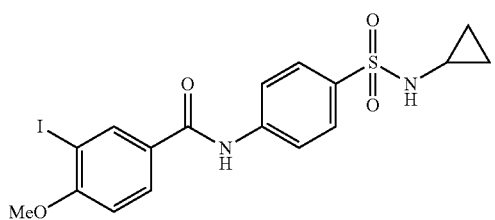

10

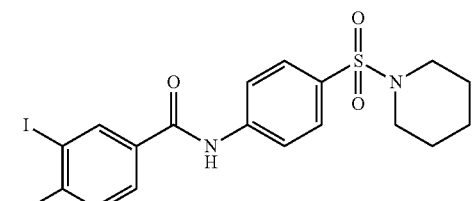

11

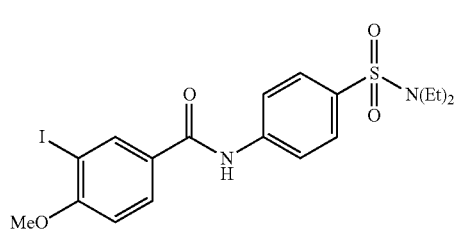

-continued
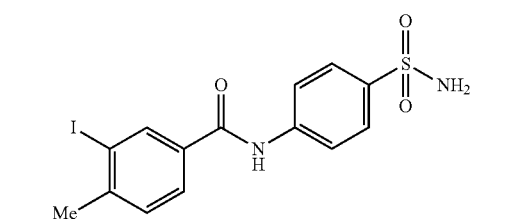
12
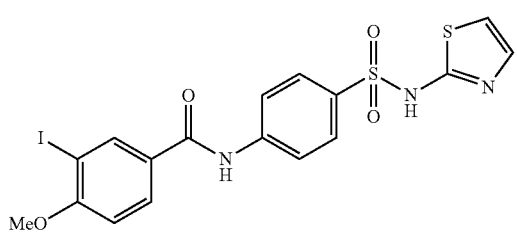
13
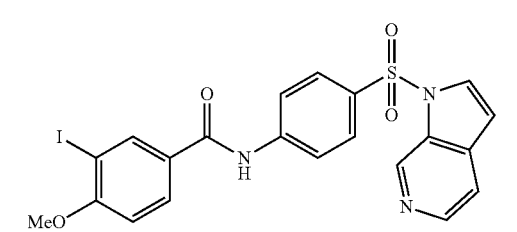
14
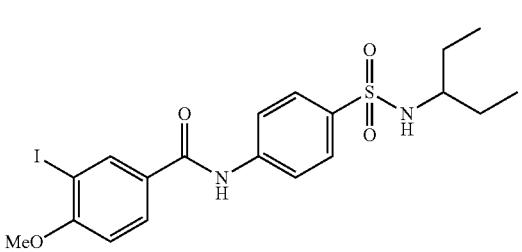
15
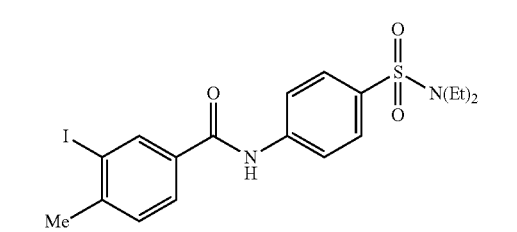
16
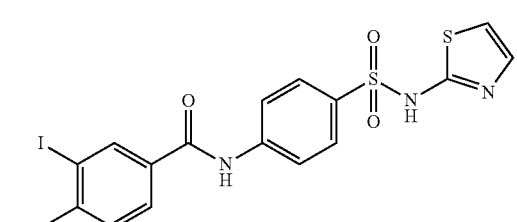
17
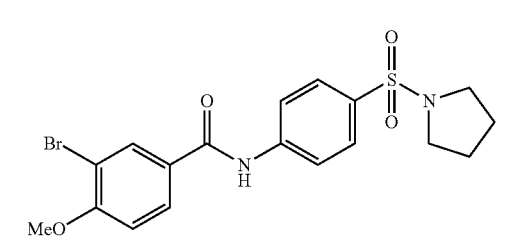
18
-continued
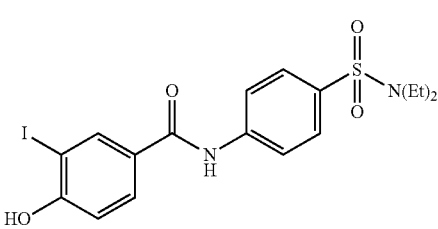
19
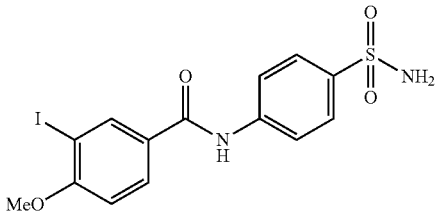
20
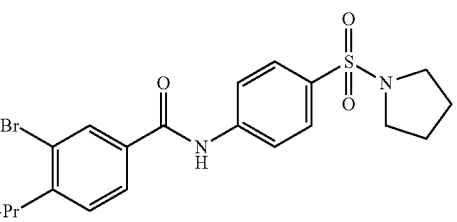
21
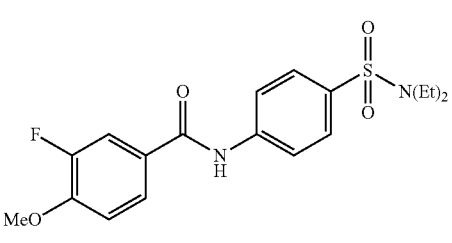
22
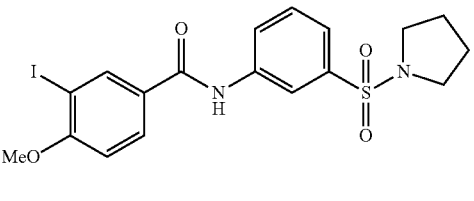
23
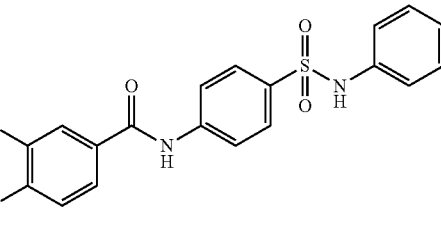
24
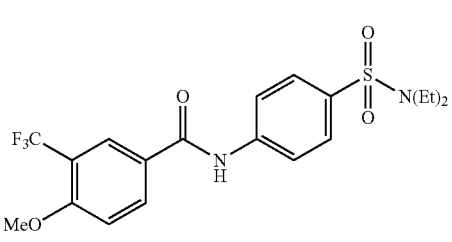
25

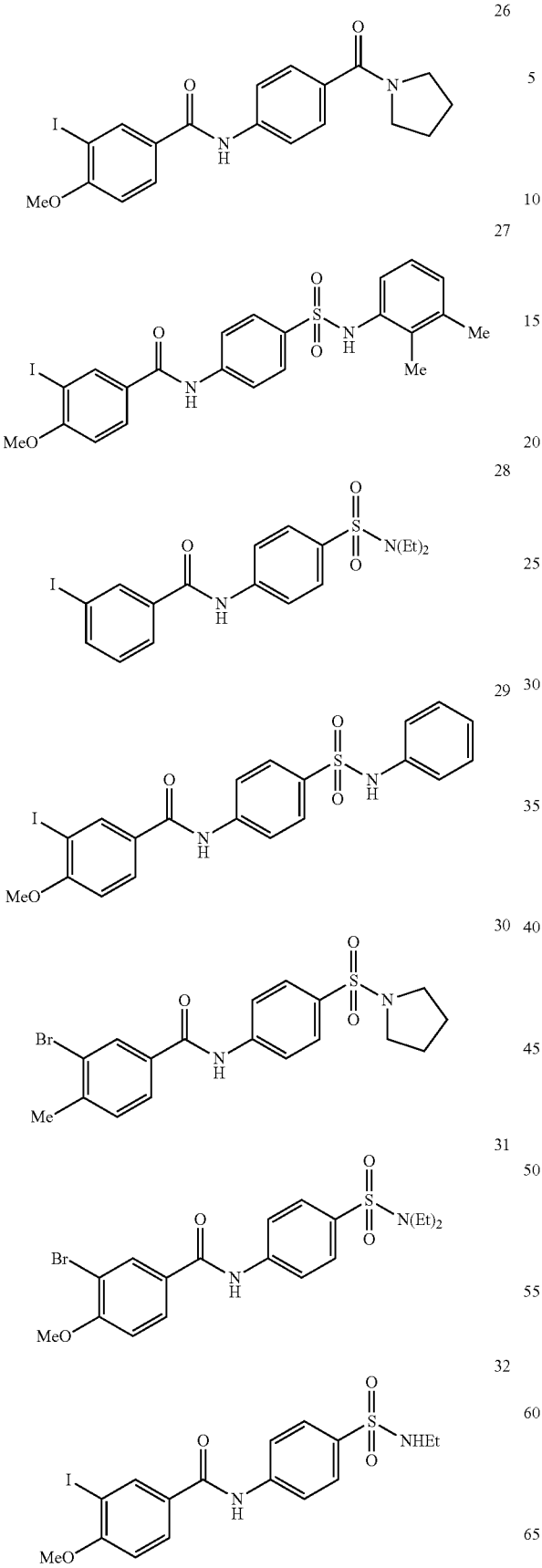
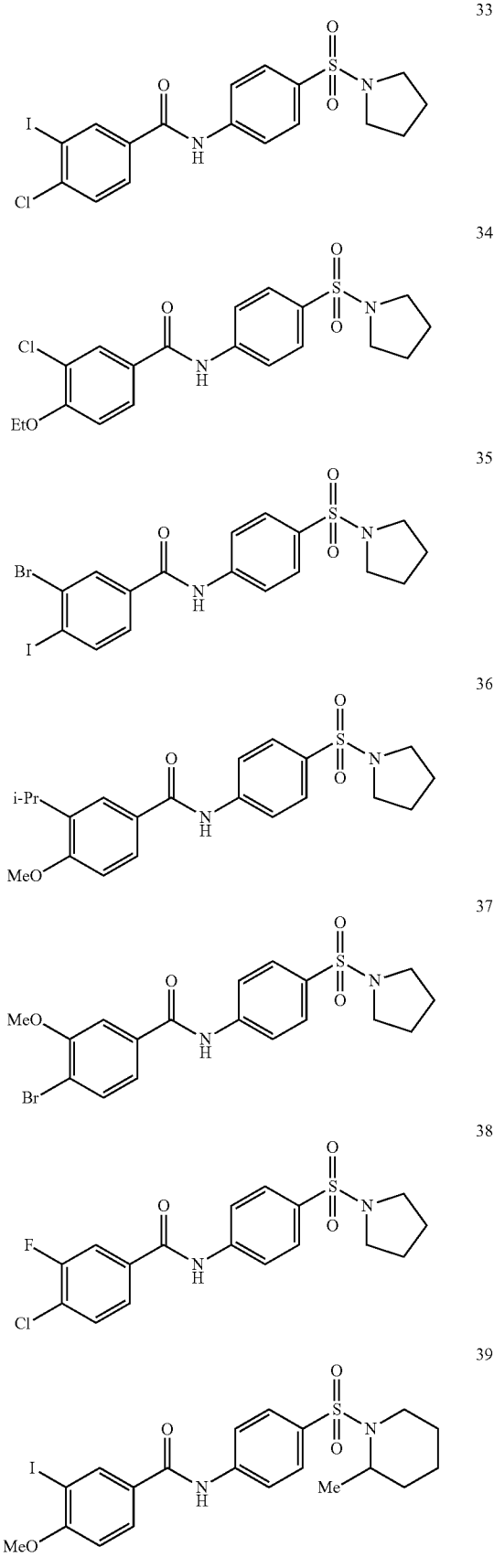

-continued (page of chemical structures, compounds 40–53)

54
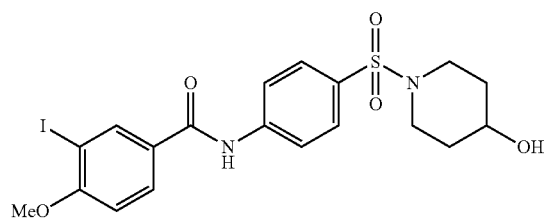
55
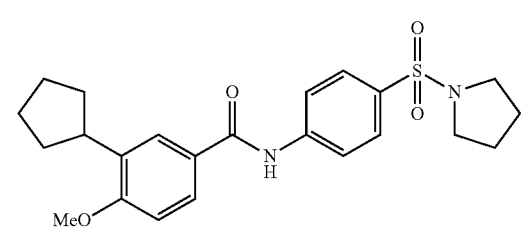
56
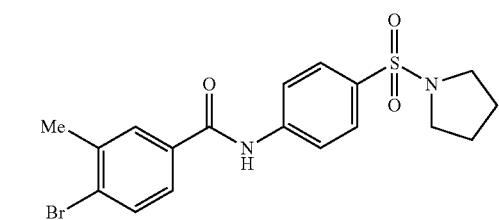
57
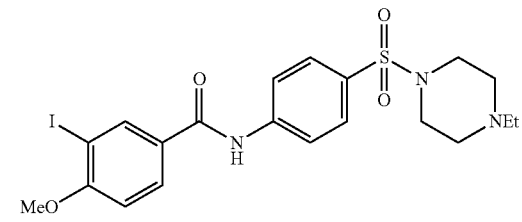
58
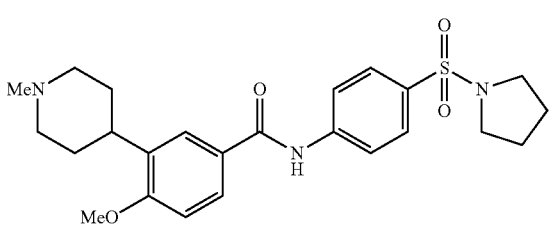
59
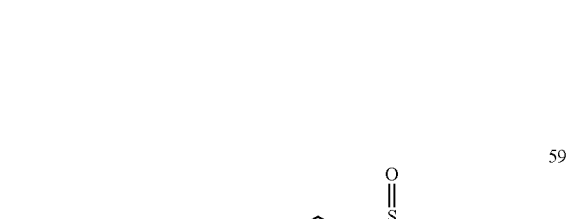
60
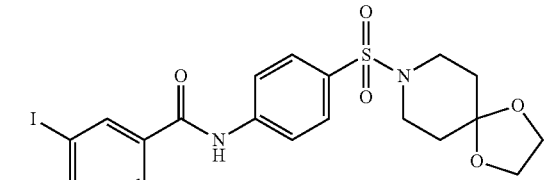
61
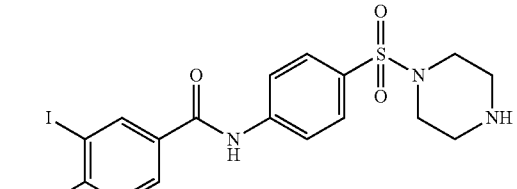
62
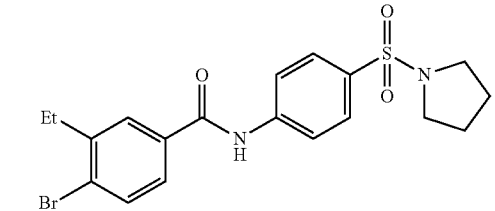
63
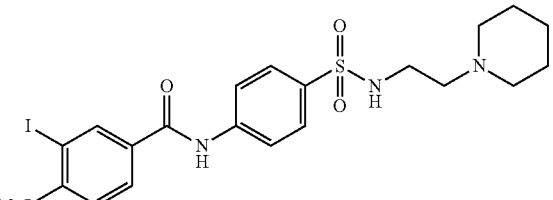
64
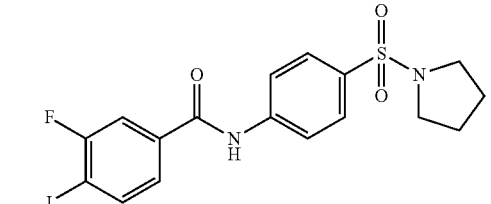
65
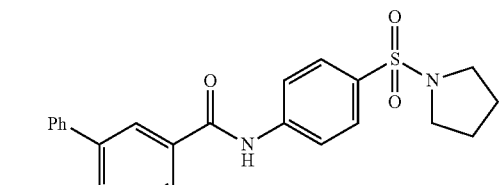
66
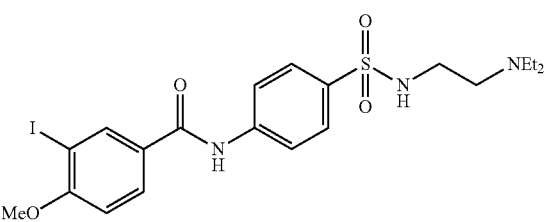

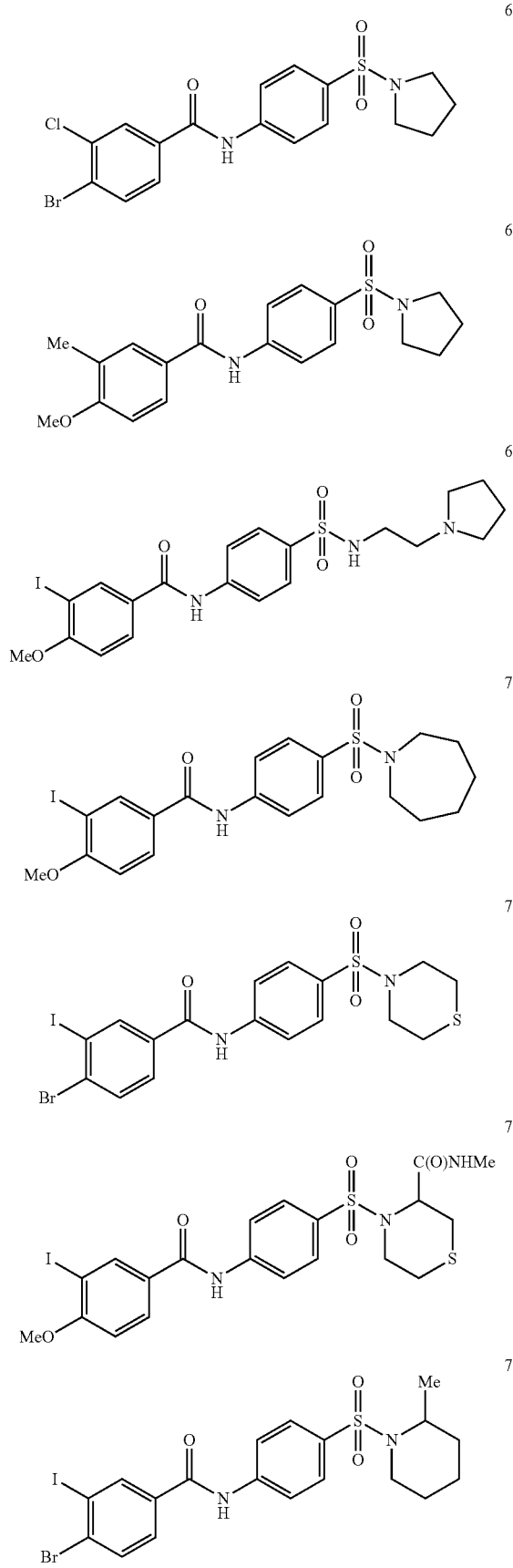
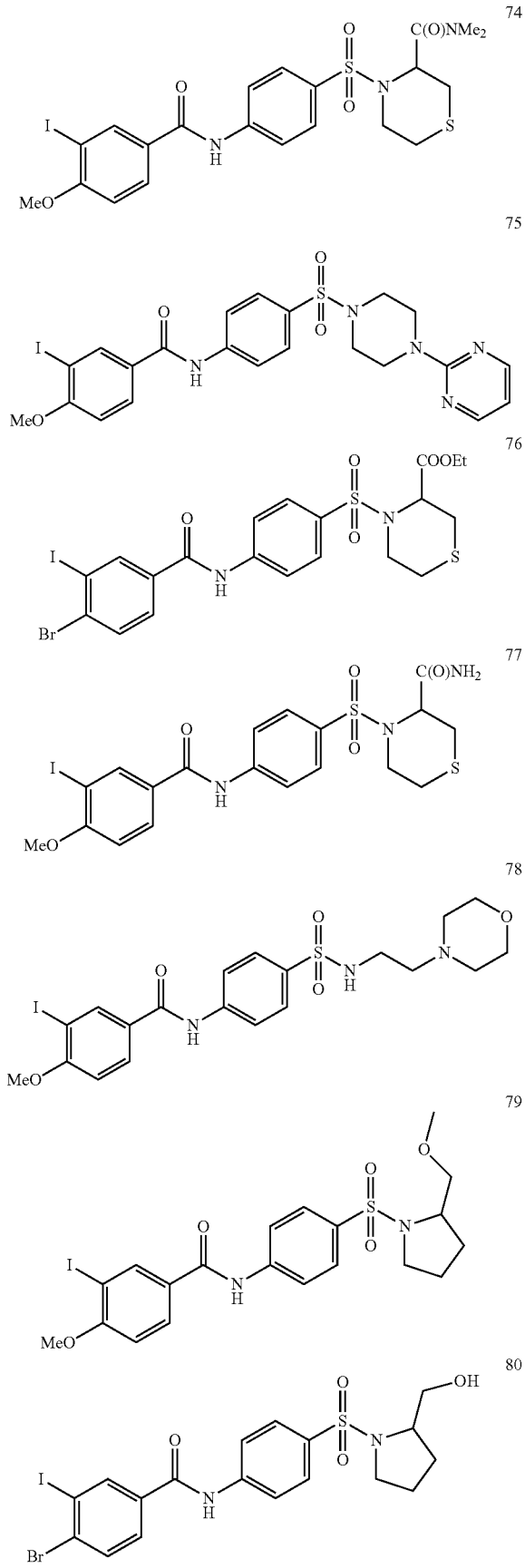

-continued
81 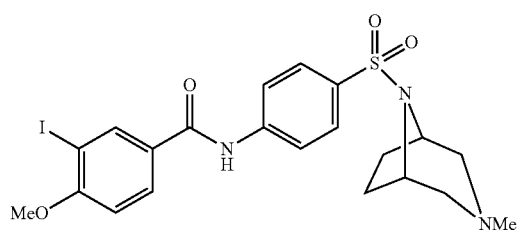
82 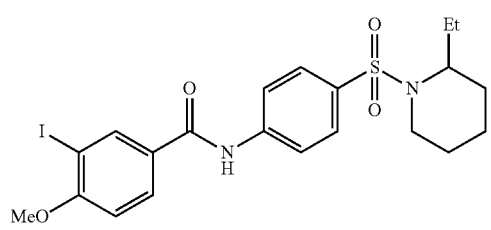
83 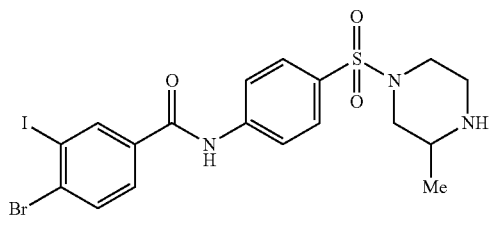
84 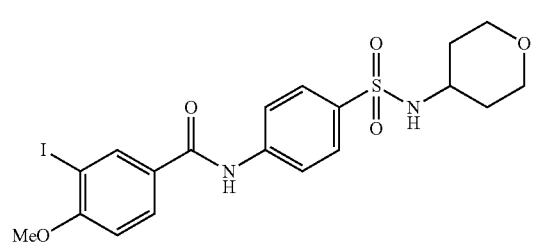
85 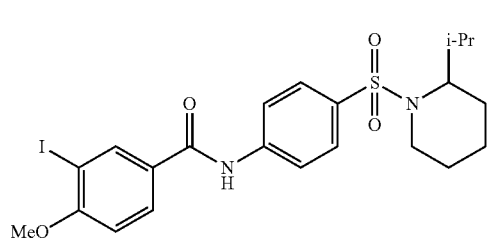
86 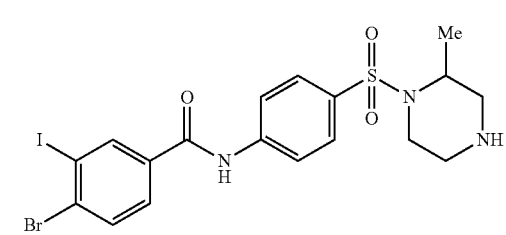
87 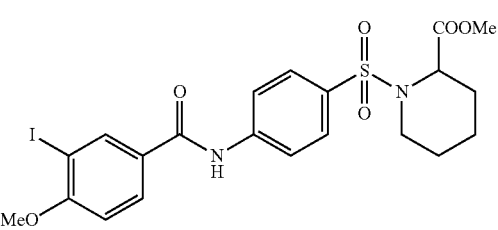
-continued
88 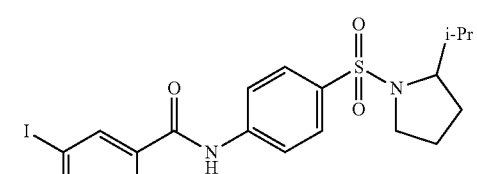
89 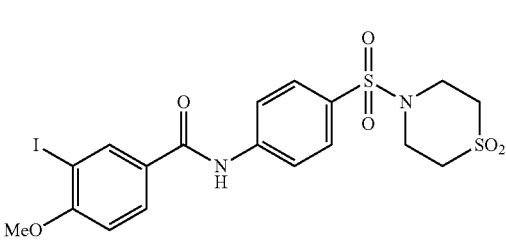
90 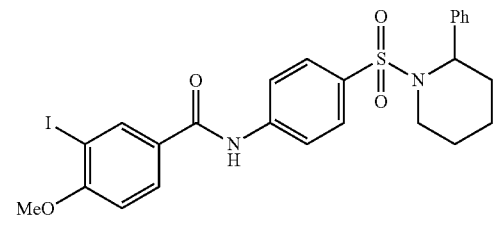
91 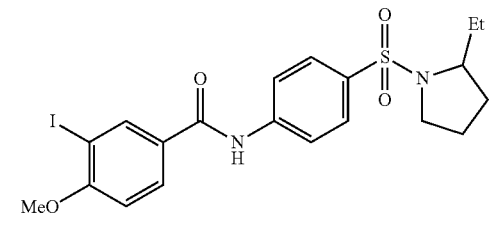
92 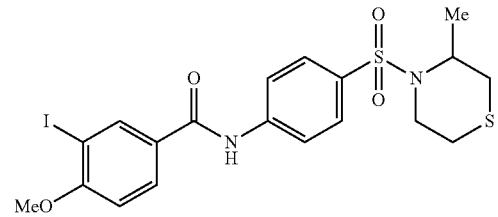
93 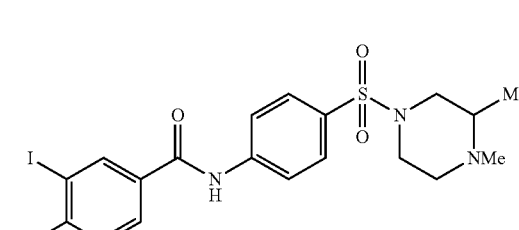
94 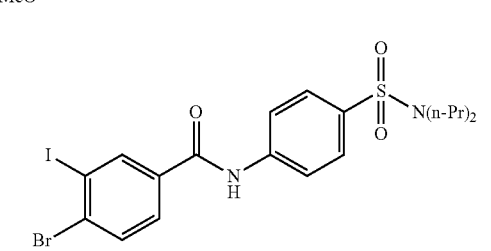

-continued

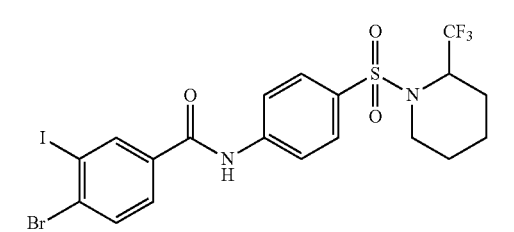
109
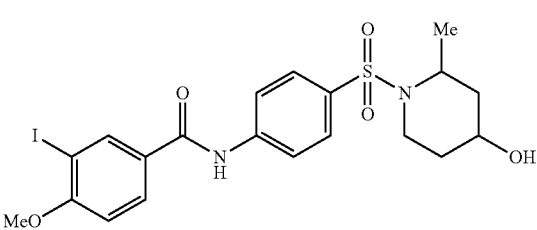
110
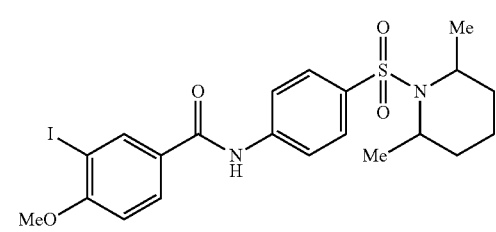
111
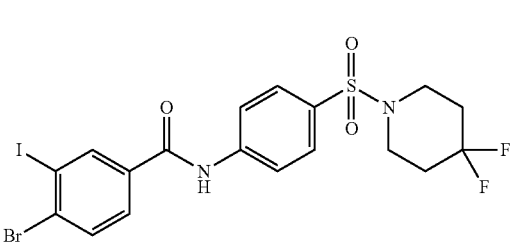
112
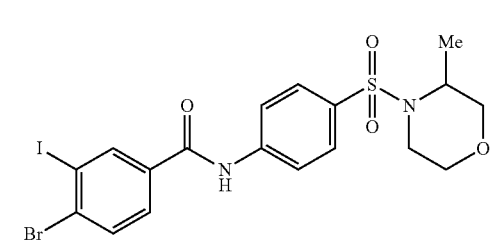
113
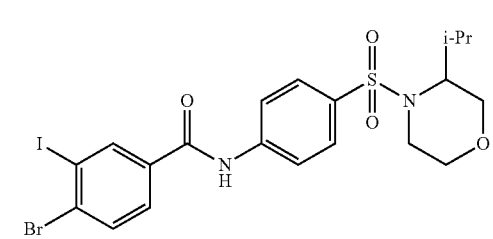
114
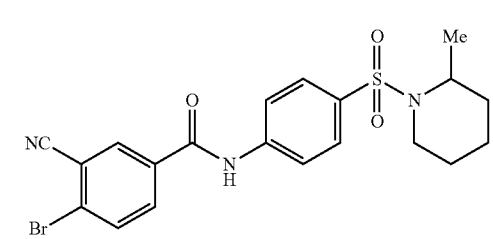
115
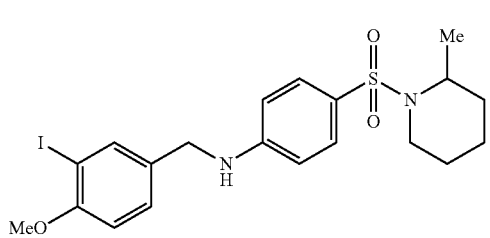
116
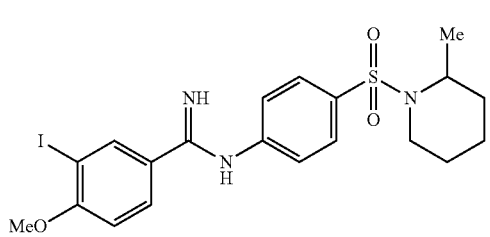
117
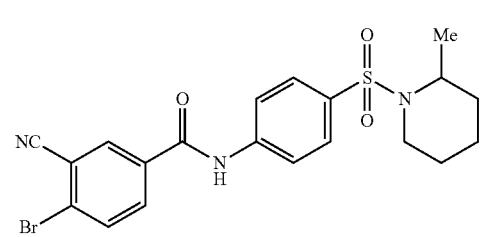
118
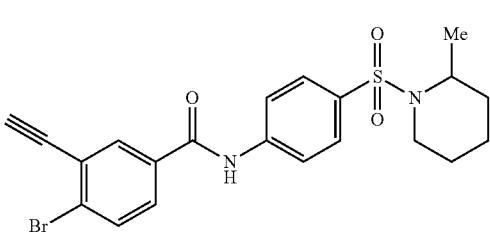
119
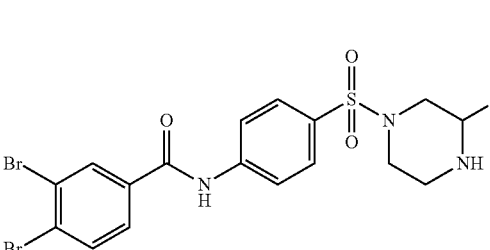
120
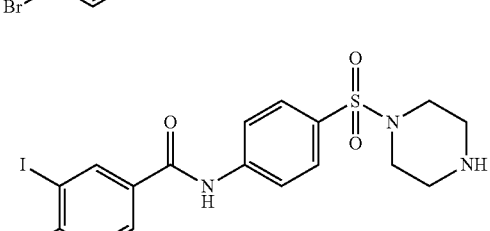
121
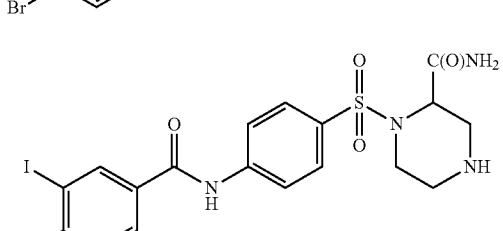
122

-continued

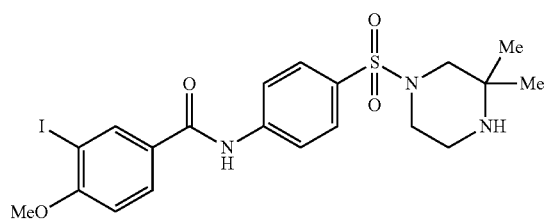

123

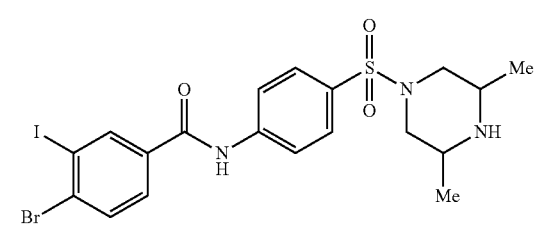

124

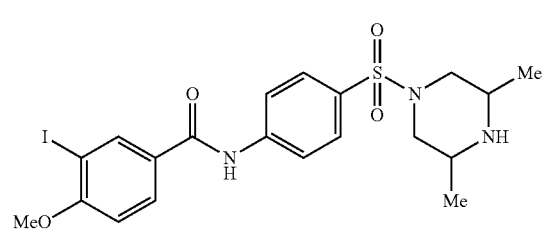

125

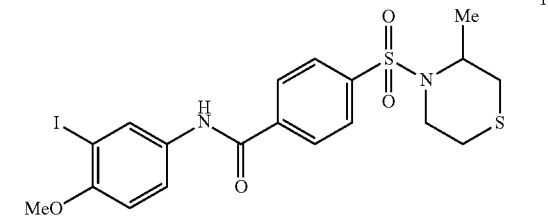

126

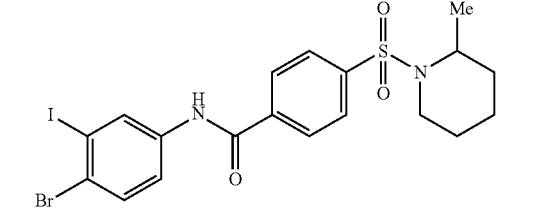

127

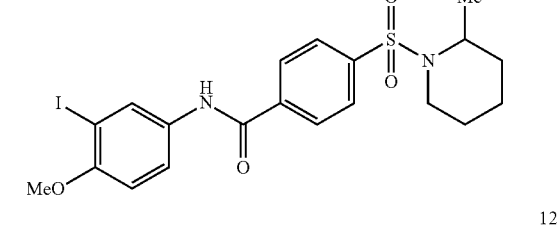

128

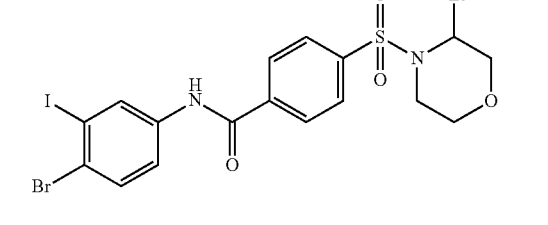

129

-continued

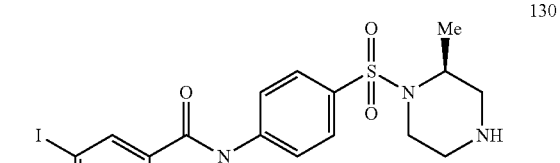

130

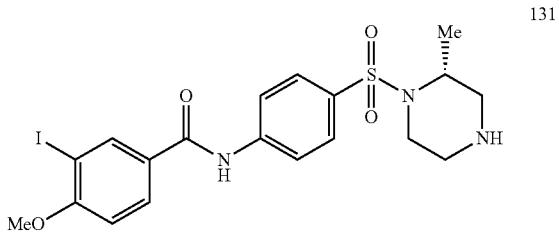

131

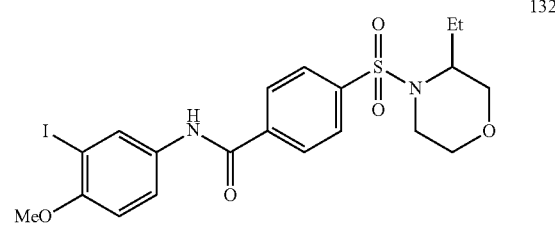

132

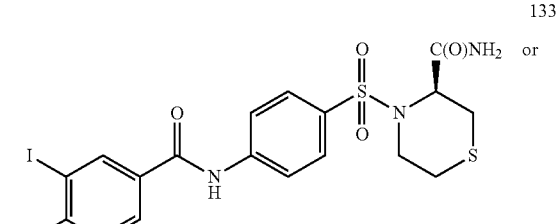

133

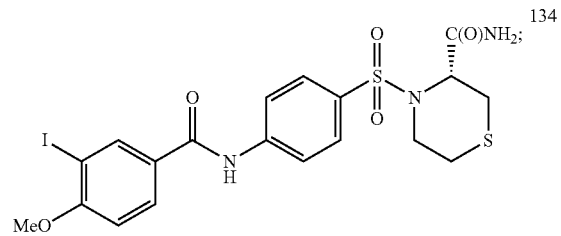

134 or a salt, enantiomer, or diastereomer thereof. It is specifically contemplated that any one or more of these compounds may be excluded in an embodiment described herein.

Certain aspects of the disclosure are directed towards compositions comprising a compound of Formula II:

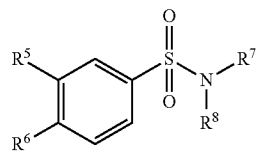

Formula II where $R^5$ and $R^6$ are each independently hydrogen, halide, substituted or unsubstituted alkyl, alkoxy, amine, alkylamine, sulfonamide, or join together to form a 5 or 6 member carbocycle or heterocycle; $R^7$, and $R^8$ are each independently hydrogen alkyl, substituted or unsubstituted aryl, wherein the substituted aryl may be substituted with amide, sulfonamide, substituted or unsubstituted alkyl, or two adjacent carbon atoms on the substituted aryl ring form a carbocycle or heterocycle ring. In some aspects, a compound of Formula II is further defined as:

135
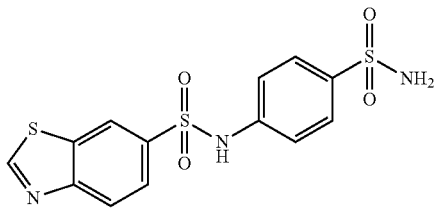

136
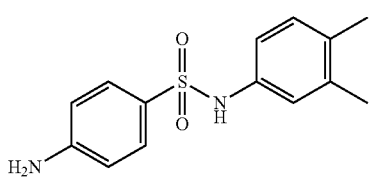

137
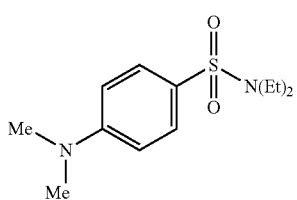

138
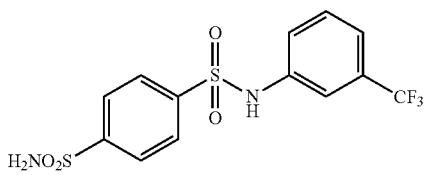

139
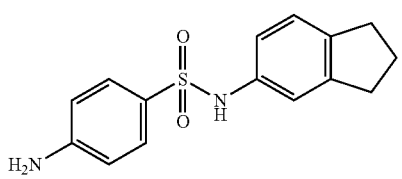

140
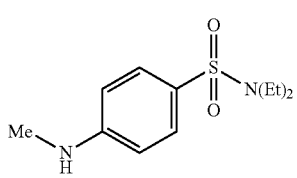

141
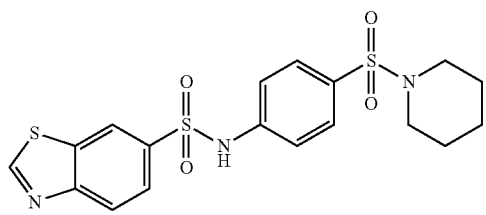

or

142
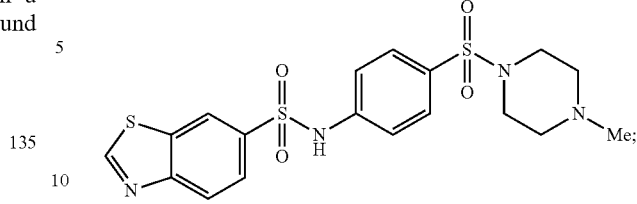

or a salt, enantiomer, or diastereomer thereof. It is specifically contemplated that one or more of these compounds may be excluded in an embodiment disclosed herein.

Certain aspects of the disclosure are directed to a method of treating a disease of the airway, a method for treating or preventing fibrosis, including pulmonary fibrosis and fibrosis outside the lung, a method for preventing or inhibiting fibroblast transformation into myofibroblasts, a method for treating, preventing, or inhibiting smooth muscle contractile protein accumulation, a method for treating or preventing airway constrictor hyperresponsiveness, a method for treating asthma, and/or a method for reversing fibrosis comprising administering to a subject a composition comprising a compound of Formula I as described herein. In some aspects, fibroblast transformation into myofibroblasts is induced by TGFβ, and a compound of Formula I will inhibit TGFβ-induced transformation of human lung fibroblasts into myofibroblasts without blocking proximal TGFβ signaling. In some embodiments, administration of a compound of Formula I inhibits localized accumulation of smooth muscle myosin heavy chains. In some aspects, administration of a compound of Formula I inhibits localized accumulation of smooth muscle alpha actin. Smooth muscle contractile proteins include bronchial, vascular, and other smooth muscle contractile proteins. The asthma may be allergic asthma, exercise-induced asthma, cough variant asthma, occupational asthma, nocturnal asthma, non-allergic asthma, adult-onset or childhood-onset asthma, asthma with fixed airflow obstruction, asthma occurring within the asthma-COPD overlap syndrome, obesity-associated asthma, asthma associated with other airways diseases such as allergic bronchopulmonary dysplasia or bronchiectasis, asthma that is associated with aspirin-exacerbated respiratory disease, or other type of asthma. The compositions and methods disclosed herein may be used in combination, i.e., a composition comprising a compound of Formula I may include at least one compound of Formula II and/or at least one additional compound of Formula I.

Some aspects of the disclosure are directed toward treating a subject that has been diagnosed with a disease of the airway comprising administering to the subject a compound of Formula I. In some aspects, a disease of the airway is bronchial fibrosis or asthma, including allergic asthma, asthma associated with aspirin-exacerbated respiratory disease, exercise-induced asthma, cough variant asthma, or occupational asthma. In some embodiments, the subject presents chronic bronchoconstriction.

In some embodiments, administration of a compound of Formula I reduces accumulation of connective tissue. In some aspects, administration of a compound of Formula I inhibits accumulation of hydroxyproline. In some embodiments, administration of a compound of Formula I inhibits accumulation of collagen. The fibrosis that may be treated by a compound of Formula I includes, but is not limited to, idiopathic pulmonary fibrosis, pulmonary fibrosis that accompanies lung diseases such as sarcoidosis or other interstitial lung diseases (e.g., those associated with collagen vascular diseases), fibrosis caused by drug toxicity (e.g., that associated with bleomycin or amiodarone), or fibrosis caused by irradiation. Other diseases involving organ fibrosis, such as those of the heart, liver, kidney, or skin, or other organs, may also be treated by a compound of Formula I, or a salt, enantiomer, diastereomer, or prodrug thereof.

Certain aspects of the disclosure are directed to a method of treating a disease of the airway, a method for treating or preventing fibrosis, including pulmonary fibrosis and fibrosis outside the lung, a method for preventing or inhibiting fibroblast transformation into myofibroblasts, a method for inhibiting or preventing smooth muscle contractile protein accumulation, a method for treating or preventing airway constrictor hyperresponsiveness, a method for treating asthma, and/or a method for reversing fibrosis comprising administering to a subject a composition comprising a compound of Formula II as described herein. In some aspects, fibroblast transformation into myofibroblasts is induced by TGFβ, and a compound of Formula II will inhibit TGFβ-induced transformation of human lung fibroblasts into myofibroblasts without blocking proximal TGFβ signaling. In some embodiments, administration of a compound of Formula II inhibits localized accumulation of smooth muscle myosin heavy chains. In some aspects, administration of a compound of Formula II inhibits localized accumulation of smooth muscle alpha actin. Smooth muscle contractile proteins include bronchial, vascular, and other smooth muscle contractile proteins. The asthma may be allergic asthma, exercise-induced asthma, cough variant asthma, occupational asthma, nocturnal asthma, non-allergic asthma, adult-onset or childhood-onset asthma, asthma with fixed airflow obstruction, asthma occurring within the asthma-COPD overlap syndrome, obesity-associated asthma, asthma associated with other airways diseases such as allergic bronchopulmonary dysplasia or bronchiectasis, asthma that is associated with aspirin-exacerbated respiratory disease, or other type of asthma. The compositions and methods disclosed herein may be used in combination, i.e., a composition comprising a compound of Formula II may include at least one compound of Formula I and/or at least one additional compound of Formula II.

Some aspects of the disclosure are directed toward treating a subject that has been diagnosed with a disease of the airway comprising administering to the subject a compound of Formula II. In some aspects, a disease of the airway is bronchial fibrosis or asthma, including allergic asthma, asthma associated with aspirin-exacerbated respiratory disease, exercise-induced asthma, cough variant asthma, or occupational asthma. In some embodiments, the subject presents chronic bronchoconstriction.

In some embodiments, administration of a compound of Formula II reduces accumulation of connective tissue. In some aspects, administration of a compound of Formula II reduces accumulation of hydroxyproline. In some embodiments, administration of a compound of Formula II inhibits accumulation of collagen. The pulmonary fibrosis that may be treated by a compound of Formula II includes, but is not limited to, idiopathic pulmonary fibrosis, pulmonary fibrosis that accompanies lung diseases such as sarcoidosis or other interstitial lung diseases (e.g., those associated with collagen vascular diseases), fibrosis caused by drug toxicity (e.g., that associated with bleomycin or amiodarone), or fibrosis caused by irradiation. Other diseases involving organ fibrosis, such as those of the heart, liver, kidney, or skin, or other organs, may also be treated by a compound of Formula II, or a salt, enantiomer, diastereomer, or prodrug thereof.

Other embodiments of the invention are discussed throughout this application. Any embodiment discussed with respect to one aspect applies to other aspects as well and vice versa. Each embodiment described herein is understood to be embodiments that are applicable to all aspects. It is contemplated that any embodiment discussed herein can be implemented with respect to any method or composition, and vice versa. Furthermore, compositions and kits can be used to achieve methods disclosed herein.

The terms "effective amount" or "therapeutically effective amount" refer to that amount of a composition of the disclosure that is sufficient to effect treatment, as defined herein, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

The term "fibrosis" refers to excessive growth of fibrous connective tissue in an organ, part, or tissue. The phrase "pulmonary fibrosis" refers to excessive growth of fibrous connective tissue in a lung. The phrase "airway constrictor hyperresponsiveness" refers to a characteristic feature of asthma in which the airway demonstrates increased sensitivity to an inhaled constrictor agonist. The phrase "airway remodeling" refers to altering airway structural cells and tissues.

The "numerical values" and "ranges" provided for the various substituents are intended to encompass all integers within the recited range. For example, when defining n as an integer representing a mixture including from about 1 to 100, where the mixture typically encompasses the integer specified as n±10% (or for smaller integers from 1 to about 25, ±3), it should be understood that n can be an integer from 1 to 100 (e.g., 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110, or any between those listed). The combined terms "about" and "±10%" or "±3" should be understood to disclose and provide specific support for equivalent ranges wherever used.

The term "optional" or "optionally" means that the subsequently described event or circumstance may or may not occur, and that the description includes instances where said event or circumstance occurs and instances in which it does not.

As used herein, "pharmaceutically acceptable carrier" or "pharmaceutically acceptable excipient" includes any and all solvents, dispersion media, coatings, antibacterial and antifungal agents, isotonic and absorption delaying agents and the like. In several embodiments, these media and agents can be used in combination with pharmaceutically active substances. Except insofar as any conventional media or agent is incompatible with the active ingredient, its use in the therapeutic compositions is contemplated. Supplementary active ingredients can also be incorporated into the compositions.

The term "remodilin" refers to any compound represented by Formula I or Formula II.

The term "treatment" or "treating" means any treatment of a disease or disorder in a mammal, including: preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device and/or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that embodiments described herein in the context of the term "comprising" may also be implemented in the context of the term "consisting of" or "consisting essentially of."

A "disease" is defined as a pathological condition of a body part, an organ, or a system resulting from any cause, such as infection, genetic defect, or environmental stress. In particular embodiments, the disease or condition is related to asthma.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Some aspects of the disclosure are directed towards the use of a composition as disclosed herein in any method disclosed herein. Some embodiments provide for the use of any composition disclosed herein for treating a disease of the airway, asthma, smooth muscle contractile protein accumulation, airway constrictor hyperresponsiveness, inhibiting transformation of fibroblasts into myofibroblasts, and for treating fibrosis, including pulmonary fibrosis and fibrosis outside the lung, or any method disclosed herein. It is specifically contemplated that any step or element of an embodiments may be implemented in the context of any other step(s) or element(s) of a different embodiment disclosed herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 3A-3E. Pharmacokinetic data showing selective accumulation remodilin 50 (FIG. 3A), remodilin 61 (FIG. 3B), remodilin 39 (FIG. 3C), remodilin 83 (FIG. 3D), and remodilin 86 (FIG. 3E) in lung (vs. other tissues or plasma), with lung concentrations $\geq 3$ µM (dotted lines) for $\geq 8$ hours after single oral doses of 10 or 50 mg/kg.

FIG. 4A Airway constrictor hyperresponsiveness methacholine dose-response curves for mice treated with remodilin 83 or 20% Solutol (vehicle). FIG. 4B Airway remodeling is reduced in remodilin-treated mice, as reflected in significantly lower MYH11 immunostain-positive airway smooth muscle area normalized to epithelial length compared with 20% Solutol (vehicle), in the large airways.

FIGS. 10A-10B. Proteins significantly stabilized or significantly destabilized by remodilin treatment. Starred Protein IDs refer to those proteins that exhibited significant ΔTm shifts of 2° C. or greater.

DETAILED DESCRIPTION

Figure 1A:
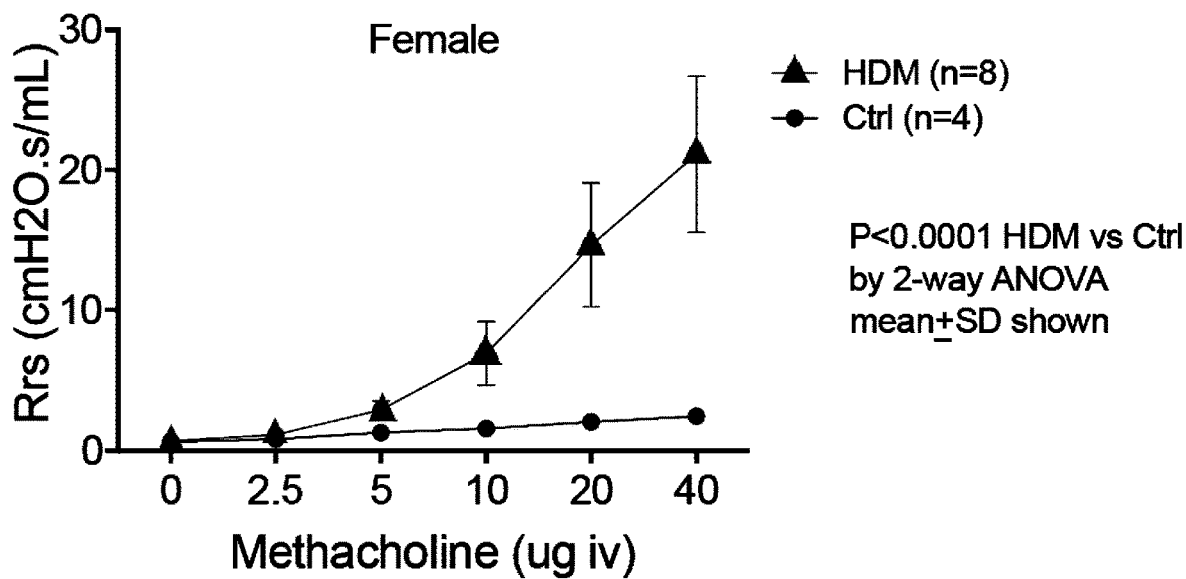
FIGS. 1A-1B. Dose-response curves for demonstrating airway constrictor hyperresponsiveness to methacholine in Balb/c female and male mice, FIG. 1A and FIG. 1B, respectively, treated with intratracheal house dust mite (HDM). Airway constrictor hyperresponsiveness was present in HDM-treated mice of each sex, compared with naïve control (Ctrl) mice.

The present invention overcomes the deficiencies of the prior art by providing remodilin compositions effective at treating asthma and associated conditions including pulmonary fibrosis, fibrosis outside the lung, contractile protein accumulation, airway constrictor hyperresponsiveness, and inhibiting transformation of fibroblasts into myofibroblasts. Because the remodilins disclosed herein target fibrosis-producing effector cells (fibroblast/myofibroblast transformation) in some embodiments, remodilins prevent fibrosis associated with a wide range of disease processes in the lung and in other organs including but not limited to skin, liver, heart, kidney, and bone marrow.

A. CHEMICAL DEFINITIONS

As used herein, a "small molecule" refers to an organic compound that is frequently synthesized via conventional organic chemistry methods (e.g., in a laboratory). Typically, a small molecule is characterized in that it contains several carbon-carbon bonds, and has a molecular weight of less than 1500 grams/mole. In certain embodiments, small molecules are less than 1000 grams/mole. In certain embodiments, small molecules are less than 550 grams/mole. In certain embodiments, small molecules are between 200 and 550 grams/mole. In certain embodiments, small molecules exclude peptides (e.g., compounds comprising 2 or more amino acids joined by a peptidyl bond). In certain embodiments, small molecules exclude nucleic acids.

As used herein, the term "amino" means —NH2; the term "nitro" means —NO2; the term "halo" or "halogen" designates —F, —Cl, —Br or —I; the term "mercapto" means —SH; the term "cyano" means —CN; the term "azido" means —N3; the term "silyl" means —SiH3, and the term "hydroxy" means —OH. In certain embodiments, a halogen may be —Br or —I.

As used herein, a "monovalent anion" refers to anions of a −1 charge. Such anions are well-known to those of skill in the art. Non-limiting examples of monovalent anions include halides (e.g., F—, Cl—, Br— and I—), NO2-, NO3-, hydroxide (OH—) and azide (N3-).

As used herein, the structure ═══ indicates that the bond may be a single bond or a double bond. Those of skill in the chemical arts understand that in certain circumstances, a double bond between two particular atoms is chemically feasible and in certain circumstances, a double bond is not. The present invention therefore contemplates that a double bond may be formed only when chemically feasible.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted Cn-alkyl, and heteroatom-substituted Cn-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted Cn-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted C1-C10-alkyl has 1 to 10 carbon atoms. The groups, —CH3 (Me), —CH2CH3 (Et), —CH2CH2CH3 (n-Pr), —CH(CH3)2 (iso-Pr), —CH(CH2)2 (cyclopropyl), —CH2CH2CH2CH3 (n-Bu), —CH(CH3)CH2CH3 (sec-butyl), —CH2CH(CH3)2 (iso-butyl), —C(CH3)3 (tert-butyl), —CH2C(CH3)3 (neo-pentyl), cyclobutyl, cyclopentyl, and cyclohexyl, are all non-limiting examples of heteroatom-unsubstituted alkyl groups. The term "heteroatom-substituted Cn-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted C1-C10-alkyl has 1 to 10 carbon atoms. The following groups are all non-limiting examples of heteroatom-substituted alkyl groups: trifluoromethyl, —CH2F, —CH2Cl, —CH2Br, —CH2OH, —CH2OCH3, —CH2OCH2CF3, —CH2OC(O)CH3, —CH2NH2, —CH2NHCH3, —CH2N(CH3)2, —CH2CH2Cl, —CH2CH2OH, CH2CH2OC(O)CH3, —CH2CH2NHCO2C(CH3)3, and —CH2Si(CH3)3.

The term "alkenyl" includes straight-chain alkenyl, branched-chain alkenyl, cycloalkenyl, cyclic alkenyl, heteroatom-unsubstituted alkenyl, heteroatom-substituted alkenyl, heteroatom-unsubstituted Cn-alkenyl, and heteroatom-substituted Cn-alkenyl. In certain embodiments, lower alkenyls are contemplated. The term "lower alkenyl" refers to alkenyls of 1-6 carbon atoms (that is, 1, 2, 3, 4, 5 or 6 carbon atoms). The term "heteroatom-unsubstituted Cn-alkenyl" refers to a radical, having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted C2-C10-alkenyl has 2 to 10 carbon atoms. Heteroatom-unsubstituted alkenyl groups include: —CH═CH2 (vinyl), —CH═CHCH3, —CH═CHCH2CH3, —CH2CH═CH2 (allyl), —CH2CH═CHCH3, and —CH═CH—C6H5. The term "heteroatom-substituted Cn-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted C2-C10-alkenyl has 2 to 10 carbon atoms. The groups, —CH═CHF, —CH═CHCl and —CH═CHBr, are non-limiting examples of heteroatom-substituted alkenyl groups.

The term "aryl" includes heteroatom-unsubstituted aryl, heteroatom-substituted aryl, heteroatom-unsubstituted Cn-aryl, heteroatom-substituted Cn-aryl, heteroaryl, heterocyclic aryl groups, carbocyclic aryl groups, biaryl groups, and single-valent radicals derived from polycyclic fused hydrocarbons (PAHs). The term "heteroatom-unsubstituted Cn-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted C6-C10-aryl has 6 to 10 carbon atoms. Non-limiting examples of heteroatom-unsubstituted aryl groups include phenyl (Ph), methylphenyl, (dimethyl)phenyl, —C6H4CH2CH3, —C6H4CH2CH2CH3, —C6H4CH(CH3)2, —C6H4CH(CH2)2, —C6H3(CH3)CH2CH3, —C6H4CH=CH2, —C6H4CH=CHCH3, —C6H4CCH, —C6H4CCCH3, naphthyl, and the radical derived from biphenyl. The term "heteroatom-substituted Cn-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted C1-C10-heteroaryl has 1 to 10 carbon atoms. Non-limiting examples of heteroatom-substituted aryl groups include the groups: —C6H4F, —C6H4Cl, —C6H4Br, —C6H4I, —C6H4OH, —C6H4OCH3, —C6H4OCH2CH3, —C6H4OC(O)CH3, —C6H4NH2, —C6H4NHCH3, —C6H4N(CH3)2, —C6H4CH2OH, —C6H4CH2OC(O)CH3, —C6H4CH2NH2, —C6H4CF3, —C6H4CN, —C6H4CHO, —C6H4CHO, —C6H4C(O)CH3, —C6H4C(O)C6H5, —C6H4CO2H, —C6H4CO2CH3, —C6H4CONH2, —C6H4CONHCH3, —C6H4CON(CH3)2, furanyl, thienyl, pyridyl, pyrrolyl, pyrimidyl, pyrazinyl, quinolyl, indolyl, and imidazoyl. In certain embodiments, heteroatom-substituted aryl groups are contemplated. In certain embodiments, heteroatom-unsubstituted aryl groups are contemplate. In certain embodiments, an aryl group may be mono-, di-, tri-, tetra- or penta-substituted with one or more heteroatom-containing substitutents.

The term "aralkyl" includes heteroatom-unsubstituted aralkyl, heteroatom-substituted aralkyl, heteroatom-unsubstituted Cn-aralkyl, heteroatom-substituted Cn-aralkyl, heteroaralkyl, and heterocyclic aralkyl groups. In certain embodiments, lower aralkyls are contemplated. The term "lower aralkyl" refers to aralkyls of 7-12 carbon atoms (that is, 7, 8, 9, 10, 11 or 12 carbon atoms). The term "heteroatom-unsubstituted Cn-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted C7-C10-aralkyl has 7 to 10 carbon atoms. Non-limiting examples of heteroatom-unsubstituted aralkyls are: phenylmethyl (benzyl, Bn) and phenylethyl. The term "heteroatom-substituted Cn-aralkyl" refers to a radical, having a single saturated carbon atom as the point of attachment, further having a total of n carbon atoms, 0, 1, or more than one hydrogen atom, and at least one heteroatom, wherein at least one of the carbon atoms is incorporated an aromatic ring structures, further wherein each heteroatom is independently selected from the group consisting of N, O, F, Cl, Br, I, Si, P, and S. For example, a heteroatom-substituted C2-C10-heteroaralkyl has 2 to 10 carbon atoms.

The term "acyl" includes straight-chain acyl, branched-chain acyl, cycloacyl, cyclic acyl, heteroatom-unsubstituted acyl, heteroatom-substituted acyl, heteroatom-unsubstituted Cn-acyl, heteroatom-substituted Cn-acyl, alkylcarbonyl, alkoxycarbonyl and aminocarbonyl groups. In certain embodiments, lower acyls are contemplated. The term "lower acyl" refers to acyls of 1-6 carbon atoms (that is, 1, 2, 3, 4, 5 or 6 carbon atoms). The term "heteroatom-unsubstituted Cn-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted C1-C10-acyl has 1 to 10 carbon atoms. The groups, —CHO, —C(O)CH3, —C(O)CH2CH3, —C(O)CH2CH2CH3, —C(O)CH(CH3)2, —C(O)CH(CH2)2, —C(O)C6H5, —C(O)C6H4CH3, —C(O)C6H4CH2CH3, and —COC6H3(CH3)2, are non-limiting examples of heteroatom-unsubstituted acyl groups. The term "heteroatom-substituted Cn-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted C1-C10-acyl has 1 to 10 carbon atoms. The groups, —C(O)CH2CF3, —CO2H, —CO2-, —CO2CH3, —CO2CH2CH3, —CO2CH2CH2CH3, —CO2CH(CH3)2, —CO2CH(CH2)2, —C(O)NH2 (carbamoyl), —C(O)NHCH3, —C(O)NHCH2CH3, —CONHCH(CH3)2, —CONHCH(CH2)2, —CON(CH3)2, and —CONHCH2CF3, are non-limiting examples of heteroatom-substituted acyl groups.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted Cn-alkoxy, and heteroatom-substituted Cn-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted Cn-alkoxy" refers to a group, having the structure —OR, in which R is a heteroatom-unsubstituted Cn-alkyl, as that term is defined above. Heteroatom-unsubstituted alkoxy groups include: —OCH3, —OCH2CH3, —OCH2CH2CH3, —OCH(CH3)2, and —OCH(CH2)2. The term "heteroatom-substituted Cn-alkoxy" refers to a group, having the structure —OR, in which R is a heteroatom-substituted Cn-alkyl, as that term is defined above. For example, —OCH2CF3 is a heteroatom-substituted alkoxy group.

The term "alkenyloxy" includes straight-chain alkenyloxy, branched-chain alkenyloxy, cycloalkenyloxy, cyclic alkenyloxy, heteroatom-unsubstituted alkenyloxy, heteroatom-substituted alkenyloxy, heteroatom-unsubstituted Cn-alkenyloxy, and heteroatom-substituted Cn-alkenyloxy. The term "heteroatom-unsubstituted Cn-alkenyloxy" refers to a group, having the structure —OR, in which R is a heteroatom-unsubstituted Cn-alkenyl, as that term is defined above. The term "heteroatom-substituted Cn-alkenyloxy" refers to a group, having the structure —OR, in which R is a heteroatom-substituted Cn-alkenyl, as that term is defined above.

The term "alkynyloxy" includes straight-chain alkynyloxy, branched-chain alkynyloxy, cycloalkynyloxy, cyclic alkynyloxy, heteroatom-unsubstituted alkynyloxy, heteroatom-substituted alkynyloxy, heteroatom-unsubstituted Cn-alkynyloxy, and heteroatom-substituted Cn-alkynyloxy. The term "heteroatom-unsubstituted Cn-alkynyloxy" refers to a group, having the structure —OR, in which R is a heteroatom-unsubstituted Cn-alkynyl, as that term is defined above. The term "heteroatom-substituted Cn-alkynyloxy" refers to a group, having the structure —OR, in which R is a heteroatom-substituted Cn-alkynyl, as that term is defined above.

The term "aryloxy" includes heteroatom-unsubstituted aryloxy, heteroatom-substituted aryloxy, heteroatom-unsubstituted Cn-aryloxy, heteroatom-substituted Cn-aryloxy, heteroaryloxy, and heterocyclic aryloxy groups. The term "heteroatom-unsubstituted Cn-aryloxy" refers to a group, having the structure —OAr, in which Ar is a heteroatom-unsubstituted Cn-aryl, as that term is defined above. A non-limiting example of a heteroatom-unsubstituted aryloxy group is —OC6H5. The term "heteroatom-substituted Cn-aryloxy" refers to a group, having the structure —OAr, in which Ar is a heteroatom-substituted Cn-aryl, as that term is defined above.

The term "aralkyloxy" includes heteroatom-unsubstituted aralkyloxy, heteroatom-substituted aralkyloxy, heteroatom-unsubstituted Cn-aralkyloxy, heteroatom-substituted Cn-aralkyloxy, heteroaralkyloxy, and heterocyclic aralkyloxy groups. The term "heteroatom-unsubstituted Cn-aralkyloxy" refers to a group, having the structure —OAr, in which Ar is a heteroatom-unsubstituted Cn-aralkyl, as that term is defined above. The term "heteroatom-substituted Cn-aralkyloxy" refers to a group, having the structure —OAr, in which Ar is a heteroatom-substituted Cn-aralkyl, as that term is defined above.

The term "acyloxy" includes straight-chain acyloxy, branched-chain acyloxy, cycloacyloxy, cyclic acyloxy, heteroatom-unsubstituted acyloxy, heteroatom-substituted acyloxy, heteroatom-unsubstituted Cn-acyloxy, heteroatom-substituted Cn-acyloxy, alkylcarbonyloxy, arylcarbonyloxy, alkoxycarbonyloxy, aryloxycarbonyloxy, and carboxylate groups. The term "heteroatom-unsubstituted Cn-acyloxy" refers to a group, having the structure —OAc, in which Ac is a heteroatom-unsubstituted Cn-acyl, as that term is defined above. For example, —OC(O)CH3 is a non-limiting example of a heteroatom-unsubstituted acyloxy group. The term "heteroatom-substituted Cn-acyloxy" refers to a group, having the structure —OAc, in which Ac is a heteroatom-substituted Cn-acyl, as that term is defined above. For example, —OC(O)OCH3 and —OC(O)NHCH3 are non-limiting examples of heteroatom-unsubstituted acyloxy groups.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted Cn-alkylamino, and heteroatom-substituted Cn-alkylamino. The term "heteroatom-unsubstituted Cn-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted C1-C10-alkylamino has 1 to 10 carbon atoms. The term "heteroatom-unsubstituted Cn-alkylamino" includes groups, having the structure —NHR, in which R is a heteroatom-unsubstituted Cn-alkyl, as that term is defined above. A heteroatom-unsubstituted alkylamino group would include —NHCH3, —NHCH2CH3, —NHCH2CH2CH3, —NHCH(CH3)2, —NHCH(CH2)2, —NHCH2 CH2 CH2 CH3, —NHCH(CH3)CH2 CH3, —NHCH2CH(CH3)2, —NHC(CH3)3, —N(CH3)2, —N(CH3)CH2CH3, —N(CH2CH3)2, N-pyrrolidinyl, and N-piperidinyl. The term "heteroatom-substituted Cn-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted C1-C10-alkylamino has 1 to 10 carbon atoms. The term "heteroatom-substituted Cn-alkylamino" includes groups, having the structure —NHR, in which R is a heteroatom-substituted Cn-alkyl, as that term is defined above.

The term "alkenylamino" includes straight-chain alkenylamino, branched-chain alkenylamino, cycloalkenylamino, cyclic alkenylamino, heteroatom-unsubstituted alkenylamino, heteroatom-substituted alkenylamino, heteroatom-unsubstituted Cn-alkenylamino, heteroatom-substituted Cn-alkenylamino, dialkenylamino, and alkyl(alkenyl)amino groups. The term "heteroatom-unsubstituted Cn-alkenylamino" refers to a radical, having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted C2-C10-alkenylamino has 2 to 10 carbon atoms. The term "heteroatom-unsubstituted Cn-alkenylamino" includes groups, having the structure —NHR, in which R is a heteroatom-unsubstituted Cn-alkenyl, as that term is defined above. The term "heteroatom-substituted Cn-alkenylamino" refers to a radical, having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted C2-C10-alkenylamino has 2 to 10 carbon atoms. The term "heteroatom-substituted Cn-alkenylamino" includes groups, having the structure —NHR, in which R is a heteroatom-substituted Cn-alkenyl, as that term is defined above.

The term "alkynylamino" includes straight-chain alkynylamino, branched-chain alkynylamino, cycloalkynylamino, cyclic alkynylamino, heteroatom-unsubstituted alkynylamino, heteroatom-substituted alkynylamino, heteroatom-unsubstituted Cn-alkynylamino, heteroatom-substituted Cn-alkynylamino, dialkynylamino, alkyl(alkynyl)amino, and alkenyl(alkynyl)amino groups. The term "heteroatom-unsubstituted Cn-alkynylamino" refers to a radical, having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atoms, a total of one nitrogen atom, and no additional heteroatoms. For example, a heteroatom-unsubstituted C2-C10-alkynylamino has 2 to 10 carbon atoms. The term "heteroatom-unsubstituted Cn-alkynylamino" includes groups, having the structure —NHR, in which R is a heteroatom-unsubstituted Cn-alkynyl, as that term is defined above. The term "heteroatom-substituted Cn-alkynylamino" refers to a radical, having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted C2-C10-alkynylamino has 2 to 10 carbon atoms. The term "heteroatom-substituted Cn-alkynylamino" includes groups, having the structure —NHR, in which R is a heteroatom-substituted Cn-alkynyl, as that term is defined above.

The term "arylamino" includes heteroatom-unsubstituted arylamino, heteroatom-substituted arylamino, heteroatom-unsubstituted Cn-arylamino, heteroatom-substituted Cn-arylamino, heteroarylamino, heterocyclic arylamino, and alkyl(aryl)amino groups. The term "heteroatom-unsubstituted Cn-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted C6-C10-arylamino has 6 to 10 carbon atoms. The term "heteroatom-unsubstituted Cn-arylamino" includes groups, having the structure —NHR, in which R is a heteroatom-unsubstituted Cn-aryl, as that term is defined above. The term "heteroatom-substituted Cn-arylamino" refers to a radical, having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted C6-C10-arylamino has 6 to 10 carbon atoms. The term "heteroatom-substituted Cn-arylamino" includes groups, having the structure —NHR, in which R is a heteroatom-substituted Cn-aryl, as that term is defined above.

The term "aralkylamino" includes heteroatom-unsubstituted aralkylamino, heteroatom-substituted aralkylamino, heteroatom-unsubstituted Cn-aralkylamino, heteroatom-substituted Cn-aralkylamino, heteroaralkylamino, heterocyclic aralkylamino groups, and diaralkylamino groups. The term "heteroatom-unsubstituted Cn-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted C7-C10-aralkylamino has 7 to 10 carbon atoms. The term "heteroatom-unsubstituted Cn-aralkylamino" includes groups, having the structure —NHR, in which R is a heteroatom-unsubstituted Cn-aralkyl, as that term is defined above. The term "heteroatom-substituted Cn-aralkylamino" refers to a radical, having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted C7-C10-aralkylamino has 7 to 10 carbon atoms. The term "heteroatom-substituted Cn-aralkylamino" includes groups, having the structure —NHR, in which R is a heteroatom-substituted Cn-aralkyl, as that term is defined above.

The term "amido" includes straight-chain amido, branched-chain amido, cycloamido, cyclic amido, heteroatom-unsubstituted amido, heteroatom-substituted amido, heteroatom-unsubstituted Cn-amido, heteroatom-substituted Cn-amido, alkylcarbonylamino, arylcarbonylamino, alkoxycarbonylamino, aryloxycarbonylamino, acylamino, alkylaminocarbonylamino, arylaminocarbonylamino, and ureido groups. The term "heteroatom-unsubstituted Cn-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted C1-C10-amido has 1 to 10 carbon atoms. The term "heteroatom-unsubstituted Cn-amido" includes groups, having the structure —NHR, in which R is a heteroatom-unsubstituted Cn-acyl, as that term is defined above. The group, —NHC(O)CH3, is a non-limiting example of a heteroatom-unsubstituted amido group. The term "heteroatom-substituted Cn-amido" refers to a radical, having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted C1-C10-amido has 1 to 10 carbon atoms. The term "heteroatom-substituted Cn-amido" includes groups, having the structure —NHR, in which R is a heteroatom-unsubstituted Cn-acyl, as that term is defined above. The group, —NHCO2CH3, is a non-limiting example of a heteroatom-substituted amido group.

The term "alkylthio" includes straight-chain alkylthio, branched-chain alkylthio, cycloalkylthio, cyclic alkylthio, heteroatom-unsubstituted alkylthio, heteroatom-substituted alkylthio, heteroatom-unsubstituted Cn-alkylthio, and heteroatom-substituted Cn-alkylthio. The term "heteroatom-unsubstituted Cn-alkylthio" refers to a group, having the structure —SR, in which R is a heteroatom-unsubstituted Cn-alkyl, as that term is defined above. The group, —SCH3, is an example of a heteroatom-unsubstituted alkylthio group. The term "heteroatom-substituted Cn-alkylthio" refers to a group, having the structure —SR, in which R is a heteroatom-substituted Cn-alkyl, as that term is defined above.

The term "alkenylthio" includes straight-chain alkenylthio, branched-chain alkenylthio, cycloalkenylthio, cyclic alkenylthio, heteroatom-unsubstituted alkenylthio, heteroatom-substituted alkenylthio, heteroatom-unsubstituted Cn-alkenylthio, and heteroatom-substituted Cn-alkenylthio. The term "heteroatom-unsubstituted Cn-alkenylthio" refers to a group, having the structure —SR, in which R is a heteroatom-unsubstituted Cn-alkenyl, as that term is defined above. The term "heteroatom-substituted Cn-alkenylthio" refers to a group, having the structure —SR, in which R is a heteroatom-substituted Cn-alkenyl, as that term is defined above.

The term "alkynylthio" includes straight-chain alkynylthio, branched-chain alkynylthio, cycloalkynylthio, cyclic alkynylthio, heteroatom-unsubstituted alkynylthio, heteroatom-substituted alkynylthio, heteroatom-unsubstituted Cn-alkynylthio, and heteroatom-substituted Cn-alkynylthio. The term "heteroatom-unsubstituted Cn-alkynylthio" refers to a group, having the structure —SR, in which R is a heteroatom-unsubstituted Cn-alkynyl, as that term is defined above. The term "heteroatom-substituted Cn-alkynylthio" refers to a group, having the structure —SR, in which R is a heteroatom-substituted Cn-alkynyl, as that term is defined above.

The term "arylthio" includes heteroatom-unsubstituted arylthio, heteroatom-substituted arylthio, heteroatom-unsubstituted Cn-arylthio, heteroatom-substituted Cn-arylthio, heteroarylthio, and heterocyclic arylthio groups. The term "heteroatom-unsubstituted Cn-arylthio" refers to a group, having the structure —SAr, in which Ar is a heteroatom-unsubstituted Cn-aryl, as that term is defined above. The group, —SC6H5, is an example of a heteroatom-unsubstituted arylthio group. The term "heteroatom-substituted Cn-arylthio" refers to a group, having the structure —SAr, in which Ar is a heteroatom-substituted Cn-aryl, as that term is defined above.

The term "aralkylthio" includes heteroatom-unsubstituted aralkylthio, heteroatom-substituted aralkylthio, heteroatom-unsubstituted Cn-aralkylthio, heteroatom-substituted Cn-aralkylthio, heteroaralkylthio, and heterocyclic aralkylthio groups. The term "heteroatom-unsubstituted Cn-aralkylthio" refers to a group, having the structure —SAr, in which Ar is a heteroatom-unsubstituted Cn-aralkyl, as that term is defined above. The group, —SCH2C6H5, is an example of a heteroatom-unsubstituted aralkyl group. The term "heteroatom-substituted Cn-aralkylthio" refers to a group, having the structure —SAr, in which Ar is a heteroatom-substituted Cn-aralkyl, as that term is defined above.

The term "acylthio" includes straight-chain acylthio, branched-chain acylthio, cycloacylthio, cyclic acylthio, heteroatom-unsubstituted acylthio, heteroatom-substituted acylthio, heteroatom-unsubstituted Cn-acylthio, heteroatom-substituted Cn-acylthio, alkylcarbonyloxy, arylcarbonyloxy, alkoxycarbonyloxy, aryloxycarbonyloxy, and carboxylate groups. The term "heteroatom-unsubstituted Cn-acylthio" refers to a group, having the structure —SAc, in which Ac is a heteroatom-unsubstituted Cn-acyl, as that term is defined above. The group, —SCOCH3, is an example of a heteroatom-unsubstituted acylthio group. The term "heteroatom-substituted Cn-acylthio" refers to a group, having the structure —SAc, in which Ac is a heteroatom-substituted Cn-acyl, as that term is defined above.

The term "alkylsilyl" includes straight-chain alkylsilyl, branched-chain alkylsilyl, cycloalkylsilyl, cyclic alkyl silyl, heteroatom-unsubstituted alkyl silyl, heteroatom-substituted alkyl silyl, heteroatom-unsubstituted Cn-alkyl silyl, and heteroatom-substituted Cn-alkyl silyl. The term "heteroatom-unsubstituted Cn-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, a heteroatom-unsubstituted C1-C10-alkylsilyl has 1 to 10 carbon atoms. An alkylsilyl group includes dialkylamino groups. The groups, —Si(CH3)3 and —Si(CH3)2C(CH3)3, are non-limiting examples of heteroatom-unsubstituted alkylsilyl groups. The term "heteroatom-substituted Cn-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a heteroatom-substituted C1-C10-alkylsilyl has 1 to 10 carbon atoms.

The term "phosphonate" includes straight-chain phosphonate, branched-chain phosphonate, cyclophosphonate, cyclic phosphonate, heteroatom-unsubstituted phosphonate, heteroatom-substituted phosphonate, heteroatom-unsubstituted Cn-phosphonate, and heteroatom-substituted Cn-phosphonate. The term "heteroatom-unsubstituted Cn-phosphonate" refers to a radical, having a single phosphorous atom as the point of attachment, further having a linear or branched, cyclic or acyclic structure, further having a total of n carbon atoms, 2 or more hydrogen atoms, a total of three oxygen atom, and no additional heteroatoms. The three oxygen atoms are directly attached to the phosphorous atom, with one of these oxygen atoms doubly bonded to the phosphorous atom. For example, a heteroatom-unsubstituted C0-C10-phosphonate has 0 to 10 carbon atoms. The groups, —P(O)(OH)2, —P(O)(OH)OCH3, —P(O)(OH)OCH2CH3, —P(O)(OCH3)2, and —P(O)(OH)(OC6H5) are non-limiting examples of heteroatom-unsubstituted phosphonate groups. The term "heteroatom-substituted Cn-phosphonate" refers to a radical, having a single phosphorous atom as the point of attachment, further having a linear or branched, cyclic or acyclic structure, further having a total of n carbon atoms, 2 or more hydrogen atoms, three or more oxygen atoms, three of which are directly attached to the phosphorous atom, with one of these three oxygen atoms doubly bonded to the phosphorous atom, and further having at least one additional heteroatom in addition to the three oxygen atoms, wherein each additional heteroatom is independently selected from the group consisting of N, O, F, Cl, Br, I, Si, P, and S. For example, a heteroatom-unsubstituted C0-C10-phosphonate has 0 to 10 carbon atoms.

The term "phosphinate" includes straight-chain phosphinate, branched-chain phosphinate, cyclophosphinate, cyclic phosphinate, heteroatom-unsubstituted phosphinate, heteroatom-substituted phosphinate, heteroatom-unsubstituted Cn-phosphinate, and heteroatom-substituted Cn-phosphinate. The term "heteroatom-unsubstituted Cn-phosphinate" refers to a radical, having a single phosphorous atom as the point of attachment, further having a linear or branched, cyclic or acyclic structure, further having a total of n carbon atoms, 2 or more hydrogen atoms, a total of two oxygen atom, and no additional heteroatoms. The two oxygen atoms are directly attached to the phosphorous atom, with one of these oxygen atoms doubly bonded to the phosphorous atom. For example, a heteroatom-unsubstituted C0-C10-phosphinate has 0 to 10 carbon atoms. The groups, —P(O)(OH)H, —P(O)(OH)CH3, —P(O)(OH)CH2CH3, —P(O)(OCH3)CH3, and —P(O)(OC6H5)H are non-limiting examples of heteroatom-unsubstituted phosphinate groups. The term "heteroatom-substituted Cn-phosphinate" refers to a radical, having a single phosphorous atom as the point of attachment, further having a linear or branched, cyclic or acyclic structure, further having a total of n carbon atoms, 2 or more hydrogen atoms, two or more oxygen atoms, two of which are directly attached to the phosphorous atom, with one of these two oxygen atoms doubly bonded to the phosphorous atom, and further having at least one additional heteroatom in addition to the two oxygen atoms, wherein each additional heteroatom is independently selected from the group consisting of N, O, F, Cl, Br, I, Si, P, and S. For example, a heteroatom-unsubstituted C0-C10-phosphinate has 0 to 10 carbon atoms.

Any apparently unfulfilled valency is to be understood to be properly filled by hydrogen atom(s). For example, a compound with a substituent of —O or —N is to be understood to be —OH or —NH2, respectively.

Any genus, subgenus, or specific compound discussed herein is specifically contemplated as being excluded from any embodiment described herein.

Compounds described herein may be prepared synthetically using conventional organic chemistry methods known to those of skill in the art and/or are commercially available (e.g., ChemBridge Co., San Diego, CA).

Embodiments are also intended to encompass salts of any of the compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps during synthesis. Salts include, but are not limited to, sodium, lithium, potassium, amines, tartrates, citrates, hydrohalides, phosphates and the like. A salt may be a pharmaceutically acceptable salt, for example. Thus, pharmaceutically acceptable salts of compounds of the present invention are contemplated.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

Derivatives of compounds of the present invention are also contemplated. In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S- or the R-configuration, as defined by the IUPAC 1974 Recommendations. Compounds may be of the D- or L-form, for example. It is well known in the art how to prepare and isolate such optically active forms. For example, mixtures of stereoisomers may be separated by standard techniques including, but not limited to, resolution of racemic form, normal, reverse-phase, and chiral chromatography, preferential salt formation, recrystallization, and the like, or by chiral synthesis either from chiral starting materials or by deliberate synthesis of target chiral centers.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include 13C and 14C.

As noted above, compounds of the present invention may exist in prodrug form. As used herein, "prodrug" is intended to include any covalently bonded carriers which release the active parent drug or compounds that are metabolized in vivo to an active drug or other compounds employed in the methods of the invention in vivo when such prodrug is administered to a subject. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a subject, cleaves to form a free hydroxyl, free amino, or carboxylic acid, respectively. Other examples include, but are not limited to, acetate, formate, and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, Selection and Use (2002), which is incorporated herein by reference.

B. PHARMACEUTICAL FORMULATIONS AND ADMINISTRATION THEREOF

1. Pharmaceutical Formulations and Routes of Administration

Pharmaceutical compositions are provided herein that comprise an effective amount of one or more substances and/or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of the invention may comprise different types of carriers depending on whether it is to be administered in solid, liquid or aerosol form, and whether it need to be sterile for such routes of administration as injection. The present invention can be administered orally, intraadiposally, intraarterially, intraarticularly, intracranially, intradermally, intralesionally, intramuscularly, intraperitoneally, intrapleurally, intranasally, intraocularally, intrapericardially, intraprostaticaly, intrarectally, intrathecally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990).

The actual dosage amount of a composition administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0% of an active ingredient (or any range derivable therein). In other embodiments, the active ingredient may comprise between about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% of the weight of the unit, or between about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60%, for example, and any range derivable therein.

In certain embodiments, pharmaceutical compositions may comprise, for example, at least about 0.1% of a compound described herein. In other embodiments, the compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Methods may involve administering to the patient or subject at least or at most 1, 2, 3, 4, 5, 6, 7, 8, 9, 10 or more doses of a therapeutic composition. A dose may be a composition comprising about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/ml or micrograms/ml or mM or μM (or any range derivable therein) of each remodilin or the total amount of a combination of remodelins.

The composition may be administered in a dose of 1-100 (this such range includes intervening doses) or more μg or any number in between the foregoing amount per dose. Each dose may be in a volume of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more μl or ml or any number in between the foregoing.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of an infection are exhibited or felt by a patient or after a clinician evaluates the patient for an infection. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of an infection (or any range derivable therein). The patient may be treated for 1, 2, 3, 4, 5, 6, 7, 8, 9, 10 or more days (or any range derivable therein) or until symptoms of an infection have disappeared or been reduced or after 6, 12, 18, or 24 hours or 1, 2, 3, 4, or 5 days after symptoms of an infection have disappeared or been reduced.

Compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months. Compositions may also be administered 30 seconds, 1, 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months or more.

It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a disease or disorder.

In additional embodiments, the composition may be administered to (or taken by) the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 μl/min, μl/hour, μl/day, μl/week, μl/month, ml/min, ml/hour, ml/day, ml/week, ml/month, μg/min, μg/hour, μg/day, μg/week, μg/month, mg/min, mg/hour, mg/day, mg/week, mg/month or any range derivable therein.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

In other embodiments, one may use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin, or combinations thereof 2. Combination Therapy The compositions and methods disclosed herein may be used in combination, i.e., a composition comprising a compound of Formula I may include at least one compound of Formula II and/or at least one additional compound of Formula I. A composition comprising a compound of Formula II may include at least one compound of Formula I and/or at least one additional compound of Formula II. The compositions and methods disclosed herein may be used in combination with traditional asthma therapies. These include, but are not limited to, administration of bronchodilators, beta-agonists, and corticosteroids, and immunotherapeutic methods, including, but not limited to omalizumab. The compositions and methods disclosed herein may be used in combination with other fibrosis therapies. These include, but are not limited to, administration of pirfenidone, nintedanib, and other anti-fibrotic therapies that are not yet FDA-approved.

Compounds discussed herein may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more remodilins may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to administering a different asthma therapeutic. In some embodiments, more than one course of therapy may be employed. It is contemplated that multiple courses may be implemented.

C. ORGANISMS AND CELL SOURCE

Methods can involve cells, tissues, or organs involving the heart, lung, kidney, liver, bone marrow, pancreas, skin, bone, vein, artery, cornea, blood, small intestine, large intestine, brain, spinal cord, smooth muscle, skeletal muscle, ovary, testis, uterus, and umbilical cord.

Moreover, methods can be employed in cells of the following type: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Chemistry Methods

All air or moisture sensitive reactions were performed under positive pressure of nitrogen with oven-dried glassware. Chemical reagents and anhydrous solvents were obtained from commercial sources and used as-is. Preparative purification was performed on a Waters semi-preparative HPLC. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis for purity was determined by a Final QC Method:

Final QC Method analysis was performed on an Agilent 1260 with a 7 minute gradient of 4% to 100% acetonitrile (containing 0.025% trifluoroacetic acid) in water (containing 0.05% trifluoroacetic acid) over 8 minute run time at a flow rate of 1 mL/min. A Phenomenex Luna C18 column (3 micron, 3×75 mm) was used at a temperature of 50° C. Purity determination was performed using an Agilent Diode Array Detector. Mass determination was performed using an Agilent 6130 mass spectrometer with electrospray ionization in the positive mode. All of the analogues for assay have purity greater than 95% based on both analytical methods. 1H and 13C NMR spectra were recorded on a Varian 400 (100) MHz spectrometer. High resolution mass spectrometry was recorded on Agilent 6210 Time-of-Flight LC/MS system. Method A: Amide coupling via acid chloride intermediate

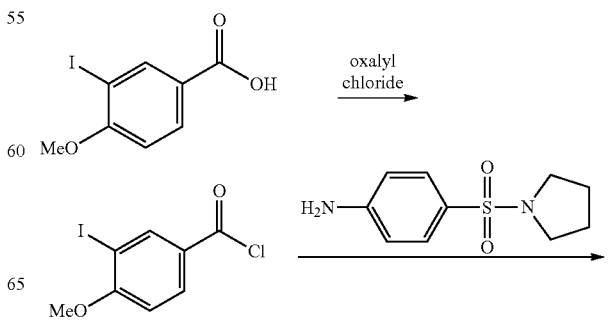

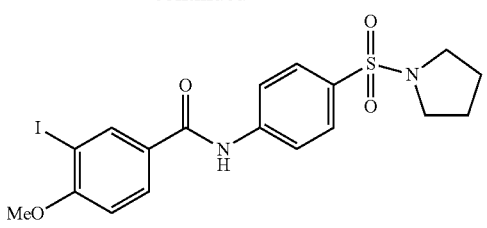

4-Bromo-3-iodobenzoic acid (0.25 g, 0.77 mmol), and oxalyl chloride (0.09 ml, 0.99 mmol) was stirred in DCM (5.00 mL) at room temperature (rt) before adding DMF (2.96 µl, 0.04 mmol) slowly. The mixture was stirred at rt for 72 h, at which time the reaction was concentrated to a white solid. The acid chloride product was reacted with 4-(pyrrolidin-1-ylsulfonyl)aniline to afford the amide product. An alternative reaction entails refluxing 1 equivalent of carboxylic acid with 1.2 equivalents of $PCl_5$ in $CHCl_3$ (1.0 mL). This reaction mixture is refluxed for 3 h then cooled and concentrated. This mixture is used neat for the acid chloride-amine coupling reaction.

Method B: Negishi coupling of organozinc and aryl halide

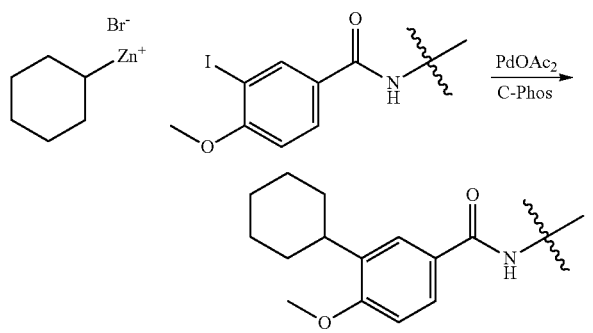

Method C: Sulfonamide formation by reaction with sulfonyl chloride intermediate, acetamide hydrolysis, and reaction between resulting amine and aromatic acid chloride

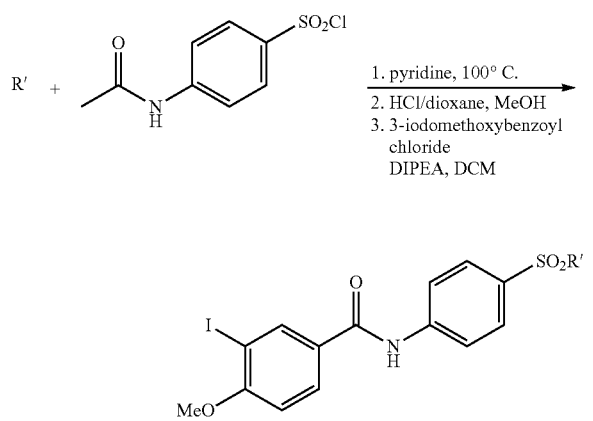

Method D: Sulfonamide formation by reaction with sulfonyl chloride intermediate, reduction of nitro to amine, and reaction between resulting amine and aromatic acid chloride

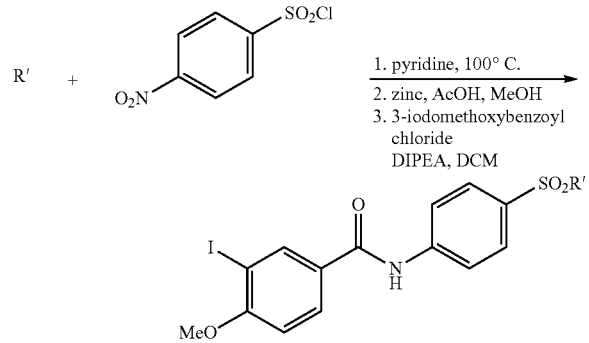

N-(4-(N,N-diethylsulfamoyl)phenyl)-3-iodo-4-methoxybenzamide (4)

4-amino-N,N-diethylbenzenesulfonamide (0.35 mmol), in DIPEA (1.00 mmol) was stirred at rt in DCM (1.0 mL) before a 1 M solution of 3-iodo-4-methoxybenzoyl chloride (0.42 mL, 0.42 mmol) in DCM was added. This solution was stirred overnight and when complete the reaction was diluted with DCM, poured into 1 N HCl and extracted 3×'s with DCM. The organic layers were combined and wash 1× with saturated bicarb and 1× with brine. The organic layer was dried with $Na_2SO_4$, filtered and concentrated. The oil was the purified by reverse phase to give the named compound. 1H NMR (400 MHz, DMSO-d6) δ 10.47 (s, 1H), 8.39 (d, J=2.2 Hz, 1H), 8.14-7.89 (m, 3H), 7.88-7.65 (m, 2H), 7.13 (d, J=8.8 Hz, 1H), 3.90 (s, 3H), 3.13 (q, J=7.1 Hz, 4H), and 1.02 (t, J=7.1 Hz, 6H); LC-MS Retention Time=5.630 min; HRMS: m/z (M+Na)+=(Calculated for C18H21IN2NaO4S, 511.0159) found, 511.0157.

3-Iodo-4-methoxy-N-(4-(pyrrolidin-1-ylsulfonyl)phenyl)benzamide (6)

Synthesize as in Method A using 4-(pyrrolidin-1-ylsulfonyl)aniline as the starting material instead of 4-amino-N,N-diethylbenzenesulfonamide. 1H NMR (400 MHz, DMSO-d6) δ 10.49 (s, 1H), 8.38 (d, J=2.2 Hz, 1H), 8.00 (dd, J=8.7, and 10.8 Hz, 3H), 7.81-7.73 (m, 2H), 7.13 (d, J=8.8 Hz, 1H), 3.90 (s, 3H), 3.17-3.07 (m, 4H), and 1.66-1.58 (m, 4H); LC-MS Retention Time=5.471 min; HRMS: m/z (M+H)+= (Calculated for C18H20IN2O4S, 487.0183) found, 487.0168.

3-Iodo-4-methoxy-N-(4-(piperidin-1-ylsulfonyl)phenyl)benzamide (3)

Synthesize as in Method A using 4-(piperidin-1-ylsulfonyl)aniline, HCl as the starting material instead of 4-amino-N,N-diethylbenzenesulfonamide. 1H NMR (400 MHz, DMSO-d6) δ 10.50 (s, 1H), 8.39 (d, J=2.2 Hz, 1H), 8.05-7.95 (m, 3H), 7.72-7.64 (m, 2H), 7.13 (d, J=8.8 Hz, 1H), 3.90 (s, 3H), 2.84 (t, J=5.5 Hz, 4H), 1.57-1.46 (m, 4H), and 1.34 (s, 2H); LC-MS Retention Time=5.826 min; HRMS: m/z (M+Na)+=(Calculated for $C_{19}H_{21}IN_2NaO_4S$, 523.0159) found, 523.0169.

N-(4-(N,N-diethylsulfamoyl)phenyl)-4-methoxybenzamide (1)

Synthesize as in Method A using 4-methoxybenzoyl chloride instead of 3-iodo-4-methoxybenzoyl chloride. ¹H NMR (400 MHz, Chloroform-d) δ 8.22 (s, 1H), 7.89-7.80 (m, 2H), 7.80-7.68 (m, 4H), 6.98-6.90 (m, 2H), 3.85 (s, 3H), 3.43 (s, 1H), 3.21 (q, J=7.12 Hz, 4H), and 1.11 (t, J=7.13 Hz, 6H); LC-MS Retention Time=5.084 min; HRMS: m/z (M+H)+= (Calculated for $C_{18}H_{23}N_2O_4S$, 363.1373) found, 363.1363.

N-(4-(N,N-diethylsulfamoyl)phenyl)-3-iodo-4-methylbenzamide (16)

Synthesize as in Method A using 3-iodo-4-methylbenzoyl chloride instead of 3-iodo-4-methoxybenzoyl chloride. $^1$H NMR (400 MHz, DMSO-$d_6$) δ 10.56 (s, 1H), 8.39 (d, J=1.9 Hz, 1H), 8.00-7.92 (m, 2H), 7.89 (dd, J=1.9, and 7.9 Hz, 1H), 7.80-7.71 (m, 2H), 7.48 (dd, J=0.8, and 7.9 Hz, 1H), 3.13 (q, J=7.1 Hz, 4H), 2.43 (s, 3H), and 1.02 (t, J=7.1 Hz, 6H); LC-MS Retention Time=6.381 min; HRMS: m/z (M+H)=(Calculated for $C_{18}H_{22}IN_2O_3S$, 473.0390) found, 473.0377.

N-(4-(N,N-diethylsulfamoyl)phenyl)-4-hydroxy-3-iodobenzamide (19)

Synthesize as in Method A using 4-hydroxy-3-iodobenzoyl chloride instead of 3-iodo-4-methoxybenzoyl chloride. $^1$H NMR (400 MHz, DMSO-$d_6$) δ 10.98 (s, 1H), 10.36 (s, 1H), 8.32 (d, J=2.2 Hz, 1H), 7.99-7.90 (m, 2H), 7.83 (dd, J=2.2, and 8.5 Hz, 1H), 7.78-7.69 (m, 2H), 6.94 (d, J=8.6 Hz, 1H), 3.13 (q, J=7.1 Hz, 4H), and 1.02 (t, J=7.1 Hz, 6H); LC-MS Retention Time=5.332 min; HRMS: m/z (M+Na)+=(Calculated for $C_{17}H_{19}IN_2NaO_4S$, 497.0002) found, 497.0025.

N-(4-(N,N-diethylsulfamoyl)phenyl)-3-fluoro-4-methoxybenzamide (22)

Synthesize as in Method A using 3-fluoro-4-methoxybenzoyl chloride instead of 3-iodo-4-methoxybenzoyl chloride. $^1$H NMR (400 MHz, DMSO-$d_6$) δ 10.45 (s, 1H), 8.00-7.92 (m, 2H), 7.88-7.80 (m, 2H), 7.79-7.71 (m, 2H), 7.36-7.26 (m, 1H), 3.91 (s, 3H), 3.13 (q, J=7.1 Hz, 4H), and 1.02 (t, J=7.1 Hz, 6H); LC-MS Retention Time=5.542 min; HRMS: m/z (M+H)+=(Calculated for $C_{18}H_{22}FN_2O_4S$, 381.1279) found, 381.1274.

N-(4-(N,N-diethylsulfamoyl)phenyl)-4-methoxy-3-(trifluoromethyl) benzamide (25)

Synthesize as in Method A using 4-methoxy-3-trifluoromethylbenzoyl chloride instead of 3-iodo-4-methoxybenzoyl chloride. $^1$H NMR (400 MHz, DMSO-$d_6$) δ 10.60 (s, 1H), 8.31-8.20 (m, 2H), 8.00-7.93 (m, 2H), 7.81-7.73 (m, 2H), 7.42 (d, J=8.8 Hz, 1H), 3.97 (s, 3H), 3.14 (q, J=7.1 Hz, 4H), and 1.02 (t, J=7.1 Hz, 6H); LC-MS Retention Time=6.012 min; HRMS: m/z (M+H)+=(Calculated for $C_{19}H_{22}F_3N_2O_4S$, 431.1247) found, 431.1234.

N-(4-(N,N-diethylsulfamoyl)phenyl)-3-iodobenzamide (28)

Synthesize as in Method A using 3-iodobenzoyl chloride instead of 3-iodo-4-methoxybenzoyl chloride. $^1$H NMR (400 MHz, DMSO-$d_6$) δ 10.63 (s, 1H), 8.28 (t, J=1.5 Hz, 1H), 7.95 (tdd, J=0.8, 1.7, and 7.2 Hz, 4H), 7.81-7.72 (m, 2H), 7.38-7.29 (m, 1H), 3.13 (q, J=7.1 Hz, 4H), and 1.02 (t, J=7.1 Hz, 6H); Retention Time=6.109 min; HRMS: m/z (M+H)+=(Calculated for $C_{17}H_{20}IN_2O_3S$, 459.0234) found, 459.0216.

3-Bromo-N-(4-(N,N-diethylsulfamoyl)phenyl)-4-methoxybenzamide (31)

Synthesize as in Method A using 3-bromo-4-methoxybenzoyl chloride instead of 3-iodo-4-methoxybenzoyl chloride. $^1$H NMR (400 MHz, DMSO-$d_6$) δ 10.48 (s, 1H), 8.22 (q, J=2.4 Hz, 1H), 7.98 (dd, J=8.3, and 17.8 Hz, 3H), 7.87-7.65 (m, 2H), 7.25 (dd, J=1.9, and 8.8 Hz, 1H), 3.92 (t, J=2.2 Hz, 3H), 3.13 (p, J=5.5, and 6.5 Hz, 4H), and 1.19-0.81 (m, 6H); Retention Time=5.882 min; HRMS: m/z (M+H)+=(Calculated for $C_{18}H_{22}BrN_2O_4S$, 442.0509) found, 442.0509.

3-Chloro-N-(4-(N,N-diethylsulfamoyl)phenyl)-4-methoxybenzamide (2)

Synthesize as in Method A using 3-chloro-4-methoxybenzoyl chloride instead of 3-iodo-4-methoxybenzoyl chloride. $^1$H NMR (400 MHz, DMSO-$d_6$) δ 10.48 (s, 1H), 8.07 (d, J=2.8 Hz, 1H), 8.01-7.91 (m, 3H), 7.79-7.69 (m, 2H), 7.44-7.11 (m, 1H), 3.93 (t, J=2.1 Hz, 3H), 3.27-2.97 (m, 4H), and 1.17-0.72 (m, 6H); Retention Time=5.798 min; HRMS: m/z (M+H)+=(Calculated for $C_{18}H_{22}ClN_2O_4S$, 397.0983) found, 397.0974.

N-(3-(N,N-diethylsulfamoyl)phenyl)-3-iodo-4-methoxybenzamide (10)

Synthesize as in Method A. $^1$H NMR (400 MHz, DMSO-$d_6$) δ 10.42 (s, 1H), 8.41 (d, J=2.2 Hz, 1H), 8.25 (t, J=1.9 Hz, 1H), 8.08-7.99 (m, 2H), 7.60-7.51 (m, 1H), 7.47 (ddd, J=1.1, 1.8, and 7.8 Hz, 1H), 7.13 (d, J=8.8 Hz, 1H), 3.90 (s, 3H), 3.16 (q, J=7.1 Hz, 4H), and 1.04 (t, J=7.1 Hz, 6H); Retention Time=6.038 min; HRMS: m/z (M+H)+=(Calculated for $C_{18}H_{22}IN_2O_4S$, 489.0339) found, 489.0363.

4-Bromo-N-(4-(N,N-diethylsulfamoyl)phenyl)-3-iodobenzamide (44)

Synthesize as in Method A using 4-bromo-3-iodobenzoyl chloride instead of 3-iodo-4-methoxybenzoyl chloride. $^1$H NMR (400 MHz, DMSO-$d_6$) δ 10.65 (s, 1H), 8.45 (dd, J=0.5, and 2.0 Hz, 1H), 7.99-7.91 (m, 2H), 7.91-7.82 (m, 2H), 7.79-7.71 (m, 2H), 3.12 (q, J=7.1 Hz, 4H), and 1.01 (t, J=7.1 Hz, 6H); Retention Time=6.573 min; HRMS: m/z (M+H)+=(Calculated for $C_{17}H_{19}BrIN_2O_3S$, 538.9319) found, 538.9310.

3-Iodo-4-methoxy-N-(4-sulfamoylphenyl)benzamide, $NH_4^+$ (20)

Synthesize as in Method A using 4-aminobenzenesulfonamide as the starting material. $^1$H NMR (400 MHz, DMSO-$d_6$) δ 10.42 (s, 1H), 8.39 (d, J=2.2 Hz, 1H), 8.01 (dd, J=2.2, and 8.6 Hz, 1H), 7.97-7.82 (m, 2H), 7.84-7.70 (m, 2H), 7.23 (s, 2H), 7.13 (d, J=8.8 Hz, 1H), and 3.90 (s, 3H); Retention Time=4.470 min; HRMS: m/z (M+Na)+=(Calculated for $C_{14}H_{13}IN_2NaO_4S$, 454.9533) found, 454.9527.

3-Iodo-4-methoxy-N-(4-(methylsulfonamido)phenyl)benzamide (8)

Synthesize as in Method A, N-(4-aminophenyl)methanesulfonamide (0.06 g, 0.34 mmol), and DIPEA (0.24 mL, 1.36 mmol) were combined in DCM (1.700 mL) before a 1 M solution of 3-iodo-4-methoxybenzoyl chloride (0.10 g, 0.34 mmol) in DCM was added. The reaction was allowed to stir overnight and was quenched with methanol before the reaction was purified by reverse phase to give final product. $^1$H NMR (400 MHz, DMSO-$d_6$) δ 10.12 (s, 1H), 9.55 (s, 1H), 8.36 (d, J=2.2 Hz, 1H), 7.98 (dd, J=2.2, and 8.6 Hz, 1H), 7.72-7.63 (m, 2H), 7.20-7.07 (m, 3H), 3.88 (s, 3H), and 2.92 (s, 3H); Retention Time=4.792 min; HRMS: m/z (M+Na)+=(Calculated for $C_{15}H_{15}IN_2NaO_4S$, 468.9689) found, 468.9713.

N-(4-(N-ethylsulfamoyl)phenyl)-3-iodo-4-methoxybenzamide (32)

Synthesize as in Method A, using 4-amino-N-ethylbenzenesulfonamide as the starting material. $^1$H NMR (400 MHz, DMSO-$d_6$) δ 10.45 (s, 1H), 8.39 (d, J=2.2 Hz, 1H), 8.01 (dd, J=2.2, and 8.7 Hz, 1H), 7.98-7.89 (m, 2H), 7.77-7.69 (m, 2H), 7.41 (t, J=5.8 Hz, 1H), 7.13 (d, J=8.7 Hz, 1H), 3.90 (s, 3H), 2.75 (qd, J=5.7, and 7.2 Hz, 2H), and 0.94 (t, J=7.2 Hz, 3H); Retention Time=5.061 min; HRMS: m/z (M+H)+=(Calculated for $C_{16}H_{18}IN_2O_4S$, 461.0026) found, 461.0049.

3-Bromo-4-methoxy-N-(4-(pyrrolidin-1-ylsulfonyl)phenyl)benzamide (18)

Synthesize as in Method A using 4-(pyrrolidin-1-ylsulfonyl)aniline as the starting material and 3-bromo-4-methoxybenzoyl chloride. $^1$H NMR (400 MHz, DMSO-$d_6$) δ 10.51 (s, 1H), 8.22 (d, J=2.2 Hz, 1H), 8.04-7.95 (m, 3H), 7.81-7.72 (m, 2H), 7.25 (d, J=8.8 Hz, 1H), 3.92 (s, 3H), 3.15-3.06 (m, 4H), and 1.67-1.56 (m, 4H); Retention Time=5.774 min; HRMS: m/z (M+H)+=(Calculated for $C_{18}H_{20}BrN_2O_4S$, 441.0302) found, 441.0312.

3-Bromo-4-methyl-N-(4-(pyrrolidin-1-ylsulfonyl)phenyl)benzamide (30)

Synthesize as in Method A using 4-(pyrrolidin-1-ylsulfonyl)aniline as the starting material and 3-bromo-4-methylbenzoyl chloride. $^1$H NMR (400 MHz, DMSO-$d_6$) δ 10.61 (s, 1H), 8.17 (d, J=1.8 Hz, 1H), 8.04-7.95 (m, 2H), 7.87 (dd, J=1.8, and 7.9 Hz, 1H), 7.82-7.73 (m, 2H), 7.52 (dd, J=0.8, 7.9 Hz, 1H), 3.17-3.07 (m, 4H), 2.41 (s, 3H), and 1.67-1.56 (m, 4H); Retention Time=5.868 min; HRMS: m/z (M+H)+=(Calculated for $C_{18}H_{20}BrN_2O_3S$, 424.0403) found, 424.0407.

4-Chloro-3-iodo-N-(4-(pyrrolidin-1-ylsulfonyl)phenyl)benzamide (33)

Synthesize as in Method A using 4-(pyrrolidin-1-ylsulfonyl)aniline as the starting material and the 4-chloro-5-iodobenzoyl chloride was prepared using ref$^{ii}$. $^1$H NMR (400 MHz, DMSO-$d_6$) δ 10.68 (s, 1H), 8.48 (d, J=2.1 Hz, 1H), 8.02-7.91 (m, 3H), 7.83-7.70 (m, 3H), 3.17-3.07 (m, 4H), and 1.67-1.56 (m, 4H); Retention Time=6.033 min; HRMS: m/z (M+H)+=(Calculated for $C_{17}H_{17}ClIN_2O_3S$, 491.9718) found, 491.9729.

3-Bromo-4-isopropyl-N-(4-(pyrrolidin-1-ylsulfonyl)phenyl)benzamide (21)

Synthesize as in Method A using 4-(pyrrolidin-1-ylsulfonyl)aniline as the starting material and 3-bromo-4-isopropylbenzoyl chloride. $^1$H NMR (400 MHz, DMSO-$d_6$) δ 10.61 (s, 1H), 8.15 (d, J=1.9 Hz, 1H), 8.05-7.88 (m, 3H), 7.82-7.73 (m, 2H), 7.55 (d, J=8.2 Hz, 1H), 3.29 (s, 4H), 3.15-3.06 (m, 1H), 1.67-1.56 (m, 4H), and 1.22 (d, J=6.9 Hz, 6H); Retention Time=6.415 min; HRMS: m/z (M+H)+=(Calculated for $C_{20}H_{24}BrN_2O_3S$, 453.0667) found, 453.0654.

4-Bromo-3-iodo-N-(4-(pyrrolidin-1-ylsulfonyl)phenyl)benzamide (50)

4-(Pyrrolidin-1-ylsulfonyl)aniline (0.17 g, 0.77 mmol), DIPEA (0.27 ml, 1.53 mmol) in DCM 2.5 mL was stirred for 3 min before the addition of 4-bromo-3-iodobenzoyl chloride (0.26 g, 0.77 mmol) in DCM 1 mL was added directly to round bottom. The reaction mixture was stirred overnight, concentrated, and taken up in MeOH at which time the solution was turbid. Water was added and heated until solution turned clear and then let sit for 1 h. A tan solid came out of solution, was filtered, washed with water, and dried to give 285 mg as a tan solid. $^1$H NMR (400 MHz, DMSO-$d_6$) δ 10.68 (s, 1H), 8.46 (dd, J=0.4, and 2.0 Hz, 1H), 8.02-7.94 (m, 2H), 7.92-7.81 (m, 2H), 7.82-7.74 (m, 2H), 3.17-3.06 (m, 4H), and 1.67-1.56 (m, 4H); LC-MS retention time (Method 2) 6.052 min; HRMS: m/z (M+Na)+=
(Calculated for $C_{17}H_{16}BrIN_2NaO_3S$, 556.9002) found, 556.8965.

4-Bromo-3-methoxy-N-(4-(pyrrolidin-1-ylsulfonyl)phenyl)benzamide (37)

Synthesize as in Method A using 4-(pyrrolidin-1-ylsulfonyl)aniline as the starting material and 4-bromo-5-methoxybenzoyl chloride. $^1$H NMR (400 MHz, DMSO-$d_6$): δ 10.62 (s, 1H), 8.03-7.95 (m, 2H), 7.83-7.71 (m, 3H), 7.58 (d, J=1.9 Hz, 1H), 7.48 (dd, J=2.0, 8.2 Hz, 1H), 3.93 (s, 3H), 3.15-3.07 (m, 4H), and 1.67-1.56 (m, 4H); Retention Time=5.577 min; HRMS: m/z (M+Na)+=(Calculated for $C_{18}H_{19}BrN_2NaO_4S$ 463.0122) found, 463.0137.

3-Iodo-4-methyl-N-(4-(pyrrolidin-1-ylsulfonyl)phenyl)benzamide (40)

Synthesize as in Method A using 4-(pyrrolidin-1-ylsulfonyl)aniline as the starting material and 3-iodo-4-methylbenzoyl chloride. $^1$H NMR (400 MHz, DMSO-$d_6$): δ 10.58 (s, 1H), 8.38 (d, J=1.8 Hz, 1H), 8.03-7.95 (m, 2H), 7.89 (dd, J=2.0, and 8.0 Hz, 1H), 7.81-7.73 (m, 2H), 7.48 (dd, J=0.8, and 7.9 Hz, 1H), 3.11 (td, J=3.5, and 7.0 Hz, 4H), 2.42 (s, 3H), and 1.67-1.56 (m, 4H); Retention Time=5.994 min; HRMS: m/z (M+H)+=(Calculated for $C_{18}H_{20}IN_2O_3S$, 471.0234) found, 471.0233.

3-Bromo-4-ethyl-N-(4-(pyrrolidin-1-ylsulfonyl)phenyl)benzamide (47)

Synthesize as in Method A using 4-(pyrrolidin-1-ylsulfonyl)aniline as the starting material and 3-bromo-4-ethylbenzoyl chloride. $^1$H NMR (400 MHz, DMSO-$d_6$) δ 10.61 (s, 1H), 8.16 (d, J=1.8 Hz, 1H), 8.04-7.96 (m, 2H), 7.90 (dd, J=1.8, and 8.0 Hz, 1H), 7.82-7.70 (m, 2H), 7.51 (d, J=8.0 Hz, 1H), 3.25-2.91 (m, 4H), 2.76 (q, J=7.5 Hz, 2H), 1.81-1.50 (m, 4H), and 1.18 (t, J=7.5 Hz, 3H); Retention Time=6.161 min; HRMS: m/z (M+H)+=(Calculated for $C_{19}H_{22}BrN_2O_3S$, 438.0559) found, 438.0538.

4-Acetamido-3-iodo-N-(4-(pyrrolidin-1-ylsulfonyl)phenyl)benzamide (52)

Synthesize as in Method A using 4-(pyrrolidin-1-ylsulfonyl)aniline as the starting material and 4-acetamido-3-iodobenzoyl chloride. Retention Time=4.721 min; HRMS: m/z (M+H)+=(Calculated for $C_{19}H_{21}IN_3O_4S$, 514.0292) found, 514.0307.

3,4-Dibromo-N-(4-(pyrrolidin-1-ylsulfonyl)phenyl) benzamide (59)

Synthesize as in Method A using 4-(pyrrolidin-1-ylsulfonyl)aniline as the starting material and 3,4-dibromobenzoyl chloride. $^1$H NMR (400 MHz, DMSO-d$_6$) δ 10.71 (s, 1H), 8.30 (d, J=2.1 Hz, 1H), 8.03-7.90 (m, 3H), 7.85 (dd, J=2.1, and 8.4 Hz, 1H), 7.83-7.74 (m, 2H), 3.17-3.06 (m, 4H), and 1.67-1.56 (m, 4H); Retention Time=5.951 min; HRMS: m/z (M+Na)+=(Calculated for $C_{17}H_{16}Br_2N_2NaO_3S$, 510.9121) found, 510.9134.

3-Fluoro-4-iodo-N-(4-(pyrrolidin-1-ylsulfonyl)phenyl)benzamide (64)

Synthesize as in Method A using 4-(pyrrolidin-1-ylsulfonyl)aniline as the starting material and 3-fluoro-4-iodobenzoyl chloride. $^1$H NMR (400 MHz, DMSO-d$_6$) δ 10.67 (s, 1H), 8.08-7.95 (m, 3H), 7.85-7.74 (m, 3H), 7.58 (dd, J=2.0, and 8.2 Hz, 1H), 3.15-3.06 (m, 4H), and 1.68-1.55 (m, 4H); Retention Time=5.682 min; HRMS: m/z (M+H)+=(Calculated for $C_{17}H_{17}FIN_2O_3S$, 476.0013) found, 475.9985.

4-Bromo-3-chloro-N-(4-(pyrrolidin-1-ylsulfonyl) phenyl)benzamide (67)

Synthesize as in Method A using 4-(pyrrolidin-1-ylsulfonyl)aniline as the starting material and 4-bromo-3-chlorobenzoyl chloride. $^1$H NMR (400 MHz, DMSO-d$_6$) δ 10.72 (s, 1H), 8.18 (d, J=2.2 Hz, 1H), 8.03-7.91 (m, 3H), 7.86-7.75 (m, 3H), 3.17-3.07 (m, 4H), and 1.67-1.56 (m, 4H);); Retention Time=5.877 min; HRMS: m/z (M+H)+=(Calculated for $C_{17}H_{17}BrClN_2O_3S$, 444.9804) found, 444.9805.

3-Bromo-4-iodo-N-(4-(pyrrolidin-1-ylsulfonyl)phenyl)benzamide (35)

Synthesize as in Method A using 4-(pyrrolidin-1-ylsulfonyl)aniline as the starting material and 3-bromo-4-iodobenzoyl chloride. $^1$H NMR (400 MHz, DMSO-d$_6$) δ 10.69 (s, 1H), 8.25 (d, J=2.0 Hz, 1H), 8.12 (d, J=8.2 Hz, 1H), 8.02-7.94 (m, 2H), 7.82-7.74 (m, 2H), 7.65 (dd, J=2.1, and 8.2 Hz, 1H), 3.17-3.06 (m, 4H), and 1.67-1.55 (m, 4H); Retention Time=5.026 min; HRMS: m/z (M+H)+=(Calculated for $C_{17}H_{17}BrIN_2O_3S$, 536.9163) found, 536.9158.

4-Chloro-3-fluoro-N-(4-(pyrrolidin-1-ylsulfonyl) phenyl)benzamide (38)

Synthesize as in Method A using 4-(pyrrolidin-1-ylsulfonyl)aniline as the starting material and 3-fluoro-4-chlorobenzoyl chloride. NMR (400 MHz, DMSO-d$_6$) δ 10.69 (s, 1H), 8.03-7.94 (m, 3H), 7.86-7.74 (m, 4H), 3.17-3.07 (m, 4H), 1.68-1.55 (m, 4H); Retention Time=5.355 min; HRMS: m/z (M+H)+=(Calculated for $C_{17}H_{17}ClFN_2O_3S$, 383. 0627) found, 383.0620.

3-Bromo-4-chloro-N-(4-(pyrrolidin-1-ylsulfonyl) phenyl)benzamide (41)

Synthesize as in Method A using 4-(pyrrolidin-1-ylsulfonyl)aniline as the starting material and 3-bromo-4-chlorobenzoyl chloride. $^1$H NMR (400 MHz, DMSO-d$_6$) δ 10.71 (s, 1H), 8.33 (d, J=2.0 Hz, 1H), 8.03-7.92 (m, 3H), 7.85-7.75 (m, 3H), 3.11-3.05 (m, 4H), and 1.68-1.56 (m, 4H); Retention Time=5.879 min; HRMS: m/z (M+H)+=(Calculated for $C_{17}H_{17}BrClN_2O_3S$, 444.9804) found, 444.9825.

3-Iodo-4-methoxy-N-(3-(pyrrolidin-1-ylsulfonyl) phenyl)benzamide (23)

Synthesize using Method A using 3-(pyrrolidin-1-ylsulfonyl)aniline as the starting material. $^1$H NMR (400 MHz, DMSO-d$_6$) δ 10.43 (s, 1H), 8.41 (d, J=2.2 Hz, 1H), 8.24 (t, J=1.9 Hz, 1H), 8.12-7.99 (m, 2H), 7.58 (t, J=8.0 Hz, 1H), 7.48 (ddd, J=1.0, 1.8, and 7.9 Hz, 1H), 7.13 (d, J=8.7 Hz, 1H), 3.90 (s, 3H), 3.18-3.10 (m, 4H), and 1.68-1.58 (m, 4H); Retention Time=5.629 min; HRMS: m/z (M+H)+=(Calculated for $C_{18}H_{20}IN_2O_4S$, 487.0183) found, 487.0180.

3-Iodo-4-methoxy-N-(4-(N-(thiazol-2-yl)sulfamoyl) phenyl)benzamide (17)

Synthesize using Method A using 4-amino-N-(thiazol-2-yl)benzene sulfonamide. $^1$H NMR (400 MHz, DMSO-d$_6$) δ 12.65 (s, 1H), 10.41 (s, 1H), 8.37 (d, J=2.2 Hz, 1H), 8.00 (dd, J=2.2, and 8.6 Hz, 1H), 7.93-7.83 (m, 2H), 7.79-7.69 (m, 2H), 7.22 (d, J=4.6 Hz, 1H), 7.12 (d, J=8.8 Hz, 1H), 6.79 (d, J=4.6 Hz, 1H), and 3.89 (s, 3H); Retention Time=4.663 min; HRMS: m/z (M+Na)+=(Calculated for $C_{17}H_{14}IN_3NaO_4S_2$, 537.9363) found, 537.9377.

3,4-Dimethoxy-N-(4-(pyrrolidin-1-ylsulfonyl)phenyl)benzamide (53)

Synthesize as in Method A using 4-(pyrrolidin-1-ylsulfonyl)aniline as the starting material and 3,4-dimethoxybenzoyl chloride. $^1$H NMR (400 MHz, DMSO-d$_6$) δ 10.40 (s, 1H), 8.03-7.95 (m, 2H), 7.81-7.72 (m, 2H), 7.61 (dd, J=2.1, and 8.4 Hz, 1H), 7.50 (d, J=2.1 Hz, 1H), 7.08 (d, J=8.5 Hz, 1H), 3.82 (d, J=1.2 Hz, 6H), 3.16-3.07 (m, 4H), and 1.67-1.56 (m, 4H); Retention Time=4.718 min; HRMS: m/z (M+Na)+=(Calculated for $C_{19}H_{22}N_2NaO_5S$, 413.1142) found, 413.1148.

4-Bromo-3-methyl-N-(4-(pyrrolidin-1-ylsulfonyl) phenyl)benzamide (56)

Synthesize as in Method A using 4-(pyrrolidin-1-ylsulfonyl)aniline as the starting material and 4-bromo-5-methylbenzoyl chloride. $^1$H NMR (400 MHz, DMSO-d$_6$): δ 10.62 (s, 1H), 8.03-7.95 (m, 2H), 7.94-7.89 (m, 1H), 7.82-7.72 (m, 3H), 7.69 (ddd, J=0.6, 2.3, and 8.3 Hz, 1H), 3.20-3.00 (m, 4H), 2.42 (d, J=0.6 Hz, 3H), 1.67-1.55 (m, 4H); Retention Time=5.766 min; HRMS: m/z (M+H)+=(Calculated for $C_{18}H_{20}BrN_2O_3S$, 423.0373) found, 423.0380.

4-Bromo-3-ethyl-N-(4-(pyrrolidin-1-ylsulfonyl)phenyl)benzamide (62)

Synthesize as in Method A using 4-(pyrrolidin-1-ylsulfonyl)aniline as the starting material and 4-bromo-5-ethylbenzoyl chloride. $^1$H NMR (400 MHz, DMSO-d$_6$) δ 10.61 (s, 1H), 8.03-7.95 (m, 2H), 7.92-7.84 (m, 1H), 7.82-7.65 (m, 4H), 3.11 (td, J=2.3, and 4.7 Hz, 4H), 2.77 (q, J=7.5 Hz, 2H), 1.67-1.56 (m, 4H), and 1.25-1.09 (m, 3H). Retention Time=6.053 min; HRMS: m/z (M+H)+=(Calculated for $C_{19}H_{22}BrN_2O_3S$, 439.0510) found, 439.0522.

3-Isopropyl-4-methoxy-N-(4-(pyrrolidin-1-ylsulfonyl)phenyl) benzamide (36)

Synthesize as in Method A using 4-(pyrrolidin-1-ylsulfonyl)aniline as the starting material and 3-isopropyl-4-methoxybenzoyl chloride. $^1$H NMR (400 MHz, DMSO-d$_6$): δ 10.38 (s, 1H), 8.08-7.91 (m, 2H), 7.85 (dd, J=2.3, and 8.6 Hz, 1H), 7.81-7.78 (m, 1H), 7.78-7.74 (m, 2H), 7.06 (dd, J=8.6, and 11.1 Hz, 1H), 3.86 (s, 3H), 3.26-3.20 (m, 1H), 3.21-2.99 (m, 4H), 1.76-1.43 (m, 4H), 1.19 and (d, J=6.9 Hz, 6H); Retention Time=5.865 min; HRMS: m/z (M+H)+= (Calculated for C$_{21}$H$_{27}$N$_2$O$_4$S, 403.1698) found, 403.1698.

6-Methoxy-N-(4-(pyrrolidin-1-ylsulfonyl)phenyl)-[1,1'-biphenyl]-3-carboxamide (65)

Synthesize as in Method A using 4-(pyrrolidin-1-ylsulfonyl)aniline as the starting material and 3-phenyl-4-methoxybenzoyl chloride. $^1$H NMR (400 MHz, DMSO-d$_6$) δ 10.47 (s, 1H), 8.05-7.97 (m, 3H), 7.97-7.93 (m, 1H), 7.79-7.71 (m, 2H), 7.55-7.48 (m, 2H), 7.47-7.38 (m, 3H), 7.38-7.31 (m, 1H), 7.25 (d, J=8.8 Hz, 1H), 3.82 (s, 3H), 3.19-2.98 (m, 4H), and 1.72-1.38 (m, 4H); Retention Time=5.810 min; HRMS: m/z (M+H)+=(Calculated for C$_{21}$H$_{27}$N$_2$O$_4$S, 437.1530) found, 437.1544.

4-Methoxy-3-methyl-N-(4-(pyrrolidin-1-ylsulfonyl)phenyl)benzamide (68)

Synthesize as in Method A using 4-(pyrrolidin-1-ylsulfonyl)aniline as the starting material and 3-methyl-4-methoxybenzoyl chloride. $^1$H NMR (400 MHz, DMSO-d$_6$) δ 10.38 (s, 1H), 8.03-7.96 (m, 2H), 7.88-7.71 (m, 4H), 7.06 (d, J=8.6 Hz, 1H), 3.85 (s, 3H), 3.15-3.06 (m, 4H), 2.20 (s, 3H), and 1.69-1.56 (m, 4H). Retention Time=5.680 min; HRMS: m/z (M+H)+=(Calculated for C$_{19}$H$_{23}$N$_2$O$_4$S, 375.1373) found, 375.1359.

3-Cyclohexyl-4-methoxy-N-(4-(pyrrolidin-1-ylsulfonyl)phenyl) benzamide (46)

Method B. Starting with 3-iodo-4-methoxy-N-(4-(pyrrolidin-1-ylsulfonyl)phenyl)benzamide (0.05 g, 0.10 mmol), PdOAc2 (2.00 mg, 10.28 μmol) and C-Phos (5.00 mg, 10.30 mmol) in degassed THF slowly add cyclohexylzinc(II) bromide (1.00 mL, 0.51 mmol). This mixture was stirred at rt until no starting material was observed by HPLC (1.0 h). The reaction was quenched with the addition of NH$_4$Cl and extracted with EtOAc. A scavenger was added to the organic layer and stir for 6 h. The scavenger was filter concentrate and turn in for purification. $^1$H NMR (400 MHz, DMSO-d$_6$): δ 10.37 (s, 1H), 8.03-7.95 (m, 2H), 7.84 (dd, J=2.3, and 8.6 Hz, 1H), 7.79-7.73 (m, 3H), 7.07 (d, J=8.7 Hz, 1H), 3.84 (s, 3H), 3.16-3.05 (m, 4H), 2.91 (t, J=6.8 Hz, 1H), 1.74 (q, J=14.8 Hz, 6H), 1.65-1.58 (m, 4H), and 1.49-1.16 (m, 4H); Retention Time=7.062 min; HRMS: m/z (M+H)+=(Calculated for C$_{24}$H$_3$IN$_2$O$_4$S, 443.1999) found, 443.2004.

3-Cyclobutyl-4-methoxy-N-(4-(pyrrolidin-1-ylsulfonyl)phenyl) benzamide (49)

Synthesize as seen 3-iodo-4-methoxy-N-(4-(pyrrolidin-1-ylsulfonyl)phenyl)benzamide and follow Method B using cyclobutylzinc(II) bromide instead of cyclohexylzinc(II) bromide. $^1$H NMR (400 MHz, DMSO-d$_6$): δ 10.43 (s, 1H), 8.04-7.96 (m, 2H), 7.85 (ddd, J=0.5, 2.4, and 8.5 Hz, 1H), 7.81-7.72 (m, 3H), 7.04 (d, J=8.7 Hz, 1H), 3.82 (s, 3H), 3.67 (p, J=8.7 Hz, 1H), 3.11 (td, J=3.6, 5.6, and 6.8 Hz, 4H), 2.33-2.18 (m, 2H), 2.17-1.87 (m, 3H), 1.83-1.73 (m, 1H), and 1.68-1.51 (m, 4H); Retention Time=6.493 min; HRMS: m/z (M+H)+=(Calculated for C22H27N2O4S, 415.1686) found, 415.1687.

3-Cyclopentyl-4-methoxy-N-(4-(pyrrolidin-1-ylsulfonyl)phenyl) benzamide (55)

Synthesize as seen 3-iodo-4-methoxy-N-(4-(pyrrolidin-1-ylsulfonyl)phenyl)benzamide and follow Method B using cyclopentylzinc(II) bromide instead of cyclohexylzinc(II) bromide. $^1$H NMR (400 MHz, DMSO-d$_6$): δ 10.39 (s, 1H), 8.02-7.95 (m, 2H), 7.88-7.71 (m, 4H), 7.07 (d, J=8.7 Hz, 1H), 3.85 (s, 3H), 3.33-3.20 (m, 2H), 3.15-3.06 (m, 5H), 1.96 (s, 2H), 1.76 (q, J=3.3 Hz, 1H), and 1.74-1.49 (m, 7H); Retention Time=6.919 min; HRMS: m/z (M+H)+=(Calculated for C$_{23}$H$_{29}$N$_2$O$_4$S, 429.1843) found, 429.1833.

4-Methoxy-3-(1-methylpiperidin-4-yl)-N-(4-(pyrrolidin-1-ylsulfonyl)phenyl)benzamide, TFA (58)

Synthesize as seen 3-iodo-4-methoxy-N-(4-(pyrrolidin-1-ylsulfonyl)phenyl)benzamide and follow Method B using (1-methylpiperidin-4-yl)zinc(II) bromide instead of cyclohexylzinc(II)bromide. $^1$H NMR (400 MHz, DMSO-d$_6$): δ 10.46 (s, 1H), 8.03-7.90 (m, 3H), 7.81-7.68 (m, 3H), 7.21-7.10 (m, 1H), 3.88 (s, 3H), 3.50 (d, J=12.1 Hz, 2H), 3.22-2.99 (m, 5H), 2.79 (d, J=4.6 Hz, 3H), 2.03-1.73 (m, 4H), and 1.69-1.52 (m, 4H); Retention Time=3.920 min; HRMS: m/z (M+H)+=(Calculated for C$_{24}$H$_{32}$N$_3$O$_4$S, 458.2108) found, 458.2126.

3-Iodo-4-methoxy-N-(4-((2-methylpiperidin-1-yl)sulfonyl)phenyl) benzamide (39)

To a stirred solution of 2-methylpiperidine (0.48 mL, 4.72 mmol) in pyridine (2.10 mL, 25.70 mmol) the 4-acetamidobenzene-1-sulfonyl chloride (1.00 g, 4.28 mmol) was added slowly. The reaction was heated for 3 h at 100° C., then let stir overnight at rt. Concentrated crude reaction, dissolved residue in EtOAc, and washed with 1N HCl (1×). Extract the acidic layer with EtOAc (2×'s), combined the organic layers and washed with saturated bicarb, and brine. Dried the organic layer with MgSO$_4$, filtered, concentrated, and used as is in the next reaction. The glass like oil was taken up in methanol (21.0 mL), treated with 4 M HCl/dioxanes (3 mL), and heated to reflux for 2 h. Let reaction mixture cool to rt and concentrate to a glass like oil which was used as is in the next reaction. 4-((2-methylpiperidin-1-yl)sulfonyl)aniline (1 equiv) was treated with DIPEA (3 equiv) in DCM (0.2M) and 1 M solution of 3-iodo-4-methoxybenzoyl chloride (1.5 equiv) in DCM was added to the reaction at rt. This mixture was allowed to stir overnight and was quenched after 18 hr with MeOH. The reaction was concentrated and purified to give the targeted compound. The enantiomers were separated using CHIRALPAK AS column, at 35 mL/min, isocratic MeOH, to give ee's of >99% for the positive, and 98.7% of the negative compound. $^1$H NMR (400 MHz, DMSO-d$_6$): δ 10.46 (s, 1H), 8.38 (d, J=2.2 Hz, 1H), 8.04-7.90 (m, 3H), 7.79-7.70 (m, 2H), 7.13 (d, J=8.8 Hz, 1H), 4.07 (d, J=6.3 Hz, 1H), 3.90 (s, 3H), 3.57 (d, J=10.5 Hz, 1H), 2.93 (td, J=2.7, and 13.0 Hz, 1H), 1.56-1.34 (m, 5H), 1.25-1.10 (m, 1H), and 0.97 (d, J=6.9 Hz, 3H); Retention Time=6.329 min; HRMS: m/z (M+H)+= (Calculated for C$_{20}$H$_{24}$IN$_2$O$_4$S, 515.0496) found, 515.0491.

3-Iodo-4-methoxy-N-(3-(piperidin-1-ylsulfonyl) phenyl)benzamide (42)

Starting with commercially available 3-(piperidin-1-ylsulfonyl)aniline and freshly made 3-iodo-4-methoxybenzoyl chloride 1 M solution. Follow procedure for above compound (39). $^1$H NMR (400 MHz, DMSO-d$_6$): δ 10.44 (s, 1H), 8.41 (d, J=2.2 Hz, 1H), 8.17 (t, J=1.9 Hz, 1H), 8.12-7.98 (m, 2H), 7.58 (t, J=8.0 Hz, 1H), 7.40 (ddd, J=1.0, 1.8, and 7.8 Hz, 1H), 7.13 (d, J=8.8 Hz, 1H), 3.90 (s, 3H), 3.34 (s, 2H), 2.92-2.78 (m, 4H), and 1.53 (p, J=5.6 Hz, 5H);); Retention Time=6.076 min; HRMS: m/z (M+H)+=(Calculated for C$_{19}$H$_{21}$IN$_2$O$_4$S, 501.0339) found, 501.0356.

3,4-Dibromo-N-(4-((2-methylpiperidin-1-yl)sulfonyl)phenyl)benzamide

Synthesize using Method C: 4-((2-methylpiperidin-1-yl) sulfonyl)aniline HCl (1 equiv) was stirred with DIPEA (3 equiv), in DCM (0.2M) before the addition of 3,4-dibromobenzoyl chloride as the acid chloride as a 1 M solution in DCM. The reaction mixture was stirred overnight and quenched with MeOH when reaction was complete. The dibromobenzoyl chloride was synthesized the same as previously described for the 3-iodo-4-methyoxybenzolyl chloride. $^1$H NMR (400 MHz, DMSO-d$_6$): δ 10.69 (s, 1H), 8.30 (d, J=2.1 Hz, 1H), 7.89 (m, 3H), 7.84 (dd, J=2.1, and 8.3 Hz, 1H), 7.81-7.70 (m, 2H), 4.07 (dd, J=3.7, and 7.3 Hz, 1H), 3.57 (dd, J=3.8, and 13.4 Hz, 1H), 2.92 (td, J=2.6, and 13.0 Hz, 1H), 1.53-1.33 (m, 5H), 1.23-1.09 (m, 1H), and 0.96 (d, J=6.9 Hz, 3H); Retention Time=6.524 min; HRMS: m/z (M+H)+=(Calculated for C$_{19}$H$_{21}$Br$_2$N$_2$O$_3$S, 518.9596) found, 518.9598.

6-Chloro-5-methoxy-N-(4-((2-methylpiperidin-1-yl) sulfonyl)phenyl) picolinamide, NH$_4^+$ (100)

Synthesize using Method C, and synthesize the acid chloride using 6-chloro-5-methoxypicolinic acid (0.13 g, 0.47 mmol), and oxalyl chloride (0.10 mL, 1.14 mmol) was stirred in DCM (0.50 mL) at rt before DMF (2.0 µL, 0.02 mmol) was added. The mixture was stirred at rt for 72 h, at which time the reaction was concentrate to a white solid. The white solid was used as is in the next reaction by making a 1 M solution in dry DCM. 4-((2-methylpiperidin-1-yl)sulfonyl)aniline (1.0 equiv) was treated with DIPEA (3.0 equiv) in DCM (0.2M) and 1 M solution of 3-chloro-4-methoxybenzoyl chloride (1.5 equiv) in DCM was added to the reaction at rt. This mixture was allowed to stir overnight and was quenched after 18 h with MeOH. The reaction was concentrated and purified to give the targeted compound. $^1$H NMR (400 MHz DMSO-d$_6$): δ 10.61 (s, 1H), 8.16-8.03 (m, 3H), 7.80-7.71 (m, 3H), 4.08 (dq, J=3.9, and 7.5 Hz, 1H), 3.98 (s, 3H), 3.62-3.53 (m, 1H), 2.94 (td, J=2.7, and 13.1 Hz, 1H), 1.59-1.30 (m, 5H), 1.26-1.07 (m, 1H), and 0.98 (d, J=6.9 Hz, 3H); Retention Time=6.017 min; HRMS: m/z (M+H)+=(Calculated for C$_{20}$H$_{24}$IN$_2$O$_4$S 515.0496) found, 515.0491.

6-Iodo-5-methoxy-N-(4-((2-methylpiperidin-1-yl) sulfonyl)phenyl)picolinamide, TFA (102)

Synthesize using Method C, followed by an amide coupling. 4-((2-methylpiperidin-1-yl)sulfonyl)aniline, HCl (0.11 g, 0.37 mmol), 6-iodo-5-methoxypicolinic acid (0.10 g, 0.37 mmol), propane phosphonic acid anhydride in DMF (0.35 mL, 0.55 mmol), and TEA (0.15 mL, 1.10 mmol) was heated to 60° C. for 2 hr. in DMF (1.80 mL). The reaction mixture was cooled to rt, poured into EtOAc, and washed with saturated NaHCO$_3$, and brine. The organic layer was dried over MgSO$_4$, filtered, concentrated, and purified to give the desired compound. $^1$H NMR (400 MHz DMSO-d$_6$): δ 10.54 (s, 1H), 8.11-8.01 (m, 3H), 7.79-7.71 (m, 2H), 7.50 (d, J=8.6 Hz, 1H), 4.07 (td, J=3.7, and 7.1 Hz, 1H), 3.95 (s, 3H), 3.29 (s, 2H), 2.93 (td, J=2.7, and 13.1 Hz, 1H), 1.49 (dd, J=3.7, and 12.4 Hz, 1H), 1.48-1.33 (m, 1H), 1.37 (s, 2H), 1.23-1.11 (m, 1H), and 0.97 (d, J=6.9 Hz, 3H); Time=6.128 min; HRMS: m/z (M+H)+=(Calculated for C$_{19}$H$_{23}$IN$_3$O$_4$S, 516.0448) found, 516.0438.

3-Iodo-4-methoxy-N-(4-(thiomorpholinosulfonyl) phenyl)benzamide (51)

Synthesize using Method C and thiomorpholine as the starting material. $^1$H NMR (400 MHz, DMSO-d$_6$): δ 10.52 (s, 1H), 8.39 (d, J=2.2 Hz, 1H), 8.05-7.97 (m, 3H), 7.74-7.67 (m, 2H), 7.13 (d, J=8.8 Hz, 1H), 3.90 (s, 3H), 3.17 (dd, J=3.7, and 6.4 Hz, 4H), and 2.68-2.60 (m, 4H); Retention Time=5.853 min; HRMS: m/z (M+H)+=(Calculated for C$_{18}$H$_{20}$IN$_2$O$_4$S$_2$, 518.9904) found, 518.9924.

3-Iodo-4-methoxy-N-(4-((3-methylthiomorpholino) sulfonyl)phenyl) benzamide (92)

Synthesize using Method C and 3-methylthiomorpholine as the starting material. $^1$H NMR (400 MHz, DMSO-d$_6$): δ 10.49 (s, 1H), 8.38 (d, J=2.2 Hz, 1H), 8.05-7.93 (m, 3H), 7.80-7.73 (m, 2H), 7.13 (d, J=8.7 Hz, 1H), 4.27 (tq, J=3.4, and 6.7 Hz, 1H), 3.90 (s, 4H), 3.34-3.21 (m, 1H), 3.19-3.07 (m, 1H), 2.81-2.72 (m, 1H), 2.43 (s, 1H), 2.34 (dt, J=2.2, and 13.6 Hz, 1H), and 1.10 (dd, J=0.6, and 6.7 Hz, 3H); Retention Time=6.031 min; HRMS: m/z (M+H)+=(Calculated for C$_{19}$H$_{22}$IN$_2$O$_4$S$_2$, 531.0060) found, 531.0070.

4-((4-(3-Iodo-4-methoxybenzamido)phenyl)sulfonyl) thiomorpholine-3-carboxylic Acid (98)

Synthesize using Method C and ethyl thiomorpholine-3-carboxylate, HCl as the starting material. The final step was a basic hydrolysis from the ester to the acid using 1N LiOH/EtOH (1:1) heated to 60° C. for 5 hr. $^1$H NMR (400 MHz, DMSO-d$_6$): δ 13.07 (s, 1H), 10.47 (s, 1H), 8.39 (d, J=2.2 Hz, 1H), 8.05-7.90 (m, 3H), 7.81-7.72 (m, 2H), 7.13 (d, J=8.8 Hz, 1H), 4.86 (d, J=3.7 Hz, 1H), 3.90 (s, 4H), 3.36 (ddd, J=5.7, 9.4, and 14.4 Hz, 1H), 3.14 (d, J=5.1 Hz, 1H), 2.95-2.86 (m, 1H), 2.76 (dd, J=4.1, and 13.7 Hz, 1H), and 2.48-2.41 (m, 1H); Retention Time=5.191 min; HRMS: m/z (M+H)+=(Calculated for C$_{19}$H$_{20}$IN$_2$O$_6$S$_2$, 562.9802) found, 562.9795.

4-((4-(3-Iodo-4-methoxybenzamido)phenyl)sulfonyl)thiomorpholine-3-carboxamide (77)

Synthesize using Method C and ethyl thiomorpholine-3-carboxylate, follow the procedure to make the carboxylic acid. 4-((4-(3-Iodo-4-methoxybenzamido)phenyl) sulfonyl) thiomorpholine-3-carboxylic acid (65.0 mg, 0.12 mmol), was treated with HOBt (18.0 mg, 0.12 mmol), ammonium hydroxide (52 uL, 0.52 mmol), and EDC (100 mg, 0.52 mmol) in DMF (600 uL) and stirred for 5 h at rt. When the starting material was consumed the reaction was concentrated and purified to give the desired material. $^1$H NMR (400 MHz, DMSO-d$_6$): δ 10.48 (s, 1H), 8.39 (d, J=2.2 Hz, 1H), 8.05-7.92 (m, 3H), 7.83-7.74 (m, 2H), 7.25 (d, J=11.5

Hz, 2H), 7.14 (d, J=8.8 Hz, 1H), 4.64 (s, 1H), 3.99-3.91 (m, 1H), 3.90 (s, 3H), 3.51 (ddd, J=6.3, 8.9, and 14.5 Hz, 1H), 2.93 (dd, J=2.8, and 14.1 Hz, 1H), 2.60 (dd, J=4.2, and 13.9 Hz, 1H), and 2.41-2.30 (m, 2H); Retention Time=4.938 min; HRMS: m/z (M+H)+=(Calculated for $C_{19}H_{21}IN_3O_5S_2$, 561.9962) found, 561.9943.

4-((4-(3-Iodo-4-methoxybenzamido)phenyl)sulfonyl)-N-methylthiomorpholine-3-carboxamide (72)

Synthesize using Method C and procedure for the synthesis of 4-((4-(3-Iodo-4-methoxybenzamido)phenyl)sulfonyl)thiomorpholine-3-carboxylic acid. 4-((4-(3-iodo-4-methoxybenzamido)phenyl)sulfonyl)thiomorpholine-3-carboxylic acid (35.0 mg, 0.062 mmol), TEA (30 uL, 0.19 mmol), HOBt (10 mg, 0.063 mmol), and methylamine hydrochloride (9.0 mg, 0.13 mmol) were stirred in DMF (0.500 mL), at rt before the addition of HATU (35.0 mg, 0.09 mmol). This reaction mixture was stirred for 18 h and diluted with EtOAc, and saturated $NaHCO_3$ to quench and separated. The organic layer was washed with brine, dried over $MgSO_4$, filtered, and concentrated to give the desired product which was purified. $^1$H NMR (400 MHz, DMSO-$d_6$): δ 10.49 (s, 1H), 8.39 (d, J=2.2 Hz, 1H), 8.06-7.93 (m, 4H), 7.85-7.75 (m, 4H), 7.14 (d, J=8.8 Hz, 1H), 4.65 (s, 1H), 4.00 (dt, J=3.1, and 14.4 Hz, 1H), 3.90 (s, 3H), 3.45 (ddd, J=4.1, 11.0, and 14.8 Hz, 1H), 2.90 (dt, J=2.4, and 13.5 Hz, 1H), 2.59 (d, J=4.5 Hz, 4H), 2.51 (d, J=4.2 Hz, 1H), 2.33 (s, 1H), and 2.39-2.24 (m, 1H); Retention Time=5.134 min; HRMS: m/z (M+H)+=(Calculated for $C_{20}H_{23}IN_3O_5S_2$, 576.0118) found, 576.0142.

4-((4-(3-Iodo-4-methoxybenzamido)phenyl)sulfonyl)-N,N-dimethylthiomorpholine-3-carboxamide (74)

Synthesize using Method C and the procedure for 4-((4-(3-iodo-4-methoxybenzamido)phenyl)sulfonyl)-N-methylthiomorpholine-3-carboxamide. $^1$H NMR (400 MHz, DMSO-$d_6$): δ 10.46 (s, 1H), 8.39 (d, J=2.2 Hz, 1H), 8.02 (dd, J=2.2, and 8.6 Hz, 1H), 7.97-7.89 (m, 2H), 7.74-7.67 (m, 2H), 7.13 (d, J=8.8 Hz, 1H), 5.07 (dd, J=3.4, and 4.6 Hz, 1H), 3.95 (ddd, J=3.6, 11.4, and 13.2 Hz, 1H), 3.90 (s, 3H), 3.79 (dt, J=3.4, and 13.2 Hz, 1H), 3.01 (s, 3H), 2.94-2.75 (m, 3H), 2.69 (s, 3H), and 2.56-2.40 (m, 1H); Retention Time=5.309 min; HRMS: m/z (M+Na)+=(Calculated for $C_{21}H_{24}IN_3NaO_5S_2$, 612.0094) found, 612.0109.

Ethyl 4-((4-(4-bromo-3-iodobenzamido)phenyl)sulfonyl)thiomorpholine-3-carboxylate (76)

Synthesize using Method C with ethyl thiomorpholine-3-carboxylate as the starting material, and 4-bromo-3-iodobenzoyl chloride as the acid chloride. $^1$H NMR (400 MHz, DMSO-$d_6$): δ 10.67 (s, 1H), 8.46 (dd, J=0.6, and 1.9 Hz, 1H), 7.97-7.92 (m, 2H), 7.89-7.85 (m, 2H), 7.80-7.74 (m, 2H), 5.00 (t, J=3.5 Hz, 1H), 4.16-3.83 (m, 3H), 3.27-3.20 (m, 1H), 2.92 (dd, J=3.3, and 13.6 Hz, 1H), 2.80 (dd, J=4.0, and 13.9 Hz, 1H), 2.52-2.48 (m, 1H), and 1.09 (t, J=7.1 Hz, 3H); Retention Time=6.530 min; HRMS: m/z (M+H)+=(Calculated for $C_{20}H_{21}BrIN_2O_5S_2$, 638.9114) found, 638.9123.

4-((4-(4-bromo-3-iodobenzamido)phenyl)sulfonyl)thiomorpholine-3-carboxylic Acid (105)

Starting with ethyl 4-((4-(4-bromo-3-iodobenzamido)phenyl)sulfonyl)thiomorpholine-3-carboxylate (0.14 g, 0.22 mmol), in a 1M solution of LiOH (1.1 mL, 1.1 mmol) in EtOH (1.1 mL) was heated to 60° C. for 1.5 hr. The reaction was allowed to cool to room temperature and the pH adjusted to 1 with 1 N HCl to give the desired material at the carboxylic acid. The reaction mixture was concentrated and sent for reverse phase purification. $^1$H NMR (400 MHz, DMSO-$d_6$) δ: 13.14 (bs, 1H), 10.66 (s, 1H), 8.45 (d, J=1.9 Hz, 1H), 7.97-7.81 (m, 4H), 7.82-7.73 (m, 2H), 4.84 (s, 1H), 3.89 (d, J=13.9 Hz, 1H), 2.90 (dd, J=2.7, and 13.6 Hz, 1H), 2.74 (dd, J=4.1, and 13.7 Hz, 1H), and 2.47-2.38 (m, 2H); Retention Time=5.616 min; HRMS: m/z (M+H)+=(Calculated for $C_{18}H_{17}BrIN_2O_5S_2$, 612.8781) found, 612.8781.

4-((4-(4-Bromo-3-iodobenzamido)phenyl)sulfonyl)thiomorpholine-3-carboxamide (108)

Synthesize using Method C and thiomorpholine-3-carboxamide as the starting material, and 4-bromo-3-iodobenzoyl chloride as the acid chloride. $^1$H NMR (400 MHz, DMSO-$d_6$): δ 10.69 (s, 1H), 8.46 (dd, J=0.4, and 2.0 Hz, 1H), 7.99-7.76 (m, 6H), 7.28 (d, J=15.5 Hz, 2H), 4.64 (t, J=3.4 Hz, 1H), 3.99-3.91 (m, 1H), 3.50 (ddd, J=5.0, 10.1, and 14.6, Hz, 1H), 2.92 (dd, J=2.8, and 14.0, Hz, 1H), 2.63-2.49 (m, 1H), and 2.45-2.29 (m, 2H); Retention Time=5.298 min; HRMS: m/z (M+H)+=(Calculated for $C_{18}H_{18}BrIN_3O_4S_2$, 611.8941) found, 611.8936.

4-Bromo-3-iodo-N-(4-(thiomorpholinosulfonyl)phenyl)benzamide, TFA (71)

Synthesize using Method C and thiomorpholine as the starting material, and 4-bromo-3-iodobenzoyl chloride as the acid chloride. $^1$H NMR (400 MHz, DMSO-$d_6$): δ 10.71 (s, 1H), 8.46 (dd, J=0.5, and 2.0 Hz, 1H), 8.04-7.96 (m, 2H), 7.93-7.82 (m, 2H), 7.77-7.68 (m, 2H), 3.21-3.14 (m, 4H), and 2.68-2.60 (m, 4H); Retention Time=6.347 min; HRMS: m/z (M+H)+=(Calculated for $C_{17}H_{17}BrIN_2O_3S_2$, 568.8883) found, 568.8906.

N-(4-((3-(tert-butyl)thiomorpholino)sulfonyl)phenyl)-3-iodo-4-methoxybenzamide (104)

Synthesize using Method C and 3-(tert-butyl)thiomorpholine as the starting material, and 3-iodo-4-methoxybenzoyl chloride as the acid chloride. $^1$H NMR (400 MHz DMSO-$d_6$): δ 10.50 (s, 1H), 8.39 (d, J=2.2 Hz, 1H), 8.05-7.90 (m, 3H), 7.91-7.78 (m, 2H), 7.13 (d, J=8.8 Hz, 1H), 4.03-3.93 (m, 1H), 3.89 (s, 3H), 3.38 (ddd, J=3.7, 12.3, and 15.7 Hz, 1H), 2.99 (s, 1H), 2.76-2.66 (m, 1H), 2.57-2.47 (m, 1H), 2.29 (d, J=14.3 Hz, 1H), 1.98 (td, J=4.6, and 12.6 Hz, 1H), and 1.01 (s, 9H); Retention Time=6.413 min; HRMS: m/z (M+H)+=(Calculated for $C_{22}H_{28}IN_2O_4S_2$, 575.0530) found, 575.0544.

N-(4-(((2-ethylthiomorpholino)sulfonyl)phenyl)-3-iodo-4-methoxybenzamide (103)

Synthesize using Method C and 2-ethylthiomorpholine as the starting material. $^1$H NMR (400 MHz DMSO-$d_6$): δ 10.51 (s, 1H), 8.39 (d, J=2.2 Hz, 1H), 8.00 (dq, J=2.5, and 9.5, Hz, 3H), 7.76-7.67 (m, 2H), 7.13 (d, J=8.7 Hz, 1H), 3.90 (s, 3H), 3.61 (td, J=4.7, 11.5, and 12.1 Hz, 2H), 2.77-2.62 (m, 4H), 2.56-2.48 (m, 1H), 1.62-1.48 (m, 1H), 1.39 (dq, J=7.5, and 14.2 Hz, 1H), and 0.91 (t, J=7.4 Hz, 3H); Retention Time=6.149 min; HRMS: m/z (M+H)+=(Calculated for $C_{20}H_{24}IN_2O_4S_2$, 547.0217) found, 547.0224.

N-(4-((2,3-dimethylthiomorpholino)sulfonyl)phenyl)-3-iodo-4-methoxybenzamide (106)

Synthesize using Method C and 2,3-dimethylthiomorpholine as the starting material. $^1$H NMR (400 MHz, DMSO-d$_6$,): δ 10.48 (s, 1H), 8.38 (d, J=2.2 Hz, 1H), 8.06-7.91 (m, 3H), 7.80-7.69 (m, 2H), 7.13 (d, J=8.8 Hz, 1H), 4.10 (qd, J=3.2, and 6.6 Hz, 1H), 3.89 (s, 3H), 3.85 (dt, J=3.2, and 14.0 Hz, 1H), 3.07-2.93 (m, 3H), 2.57 (td, J=3.3, 12.5, and 13.1 Hz, 1H), and 0.96 (dd, J=6.9, and 9.7 Hz, 6H); Retention Time=6.050 min; HRMS: m/z (M+H)+=(Calculated for C$_{20}$H$_{24}$IN$_2$O$_4$S$_2$, 547.0217) found, 547.0216.

3-Iodo-4-methoxy-N-(4-((2-methylthiomorpholino)sulfonyl)phenyl) benzamide (107)

Synthesize using Method C and 3-methylthiomorpholine as the starting material. $^1$H NMR (400 MHz DMSO-d$_6$): δ 10.52 (s, 1H), 8.38 (d, J=2.1 Hz, 1H), 8.00 (dq, J=2.5, and 9.6 Hz, 3H), 7.75-7.67 (m, 2H), 7.13 (d, J=8.7 Hz, 1H), 3.90 (s, 3H), 3.73 (dd, J=3.0, and 12.3 Hz, 2H), 2.89 (ddt, J=3.5, 7.0, and 10.9 Hz, 1H), 2.78-2.64 (m, 2H), 2.60-2.49 (m, 1H), 2.30 (dd, J=9.6, and 12.2 Hz, 1H), and 1.10 (d, J=6.8 Hz, 3H); Retention Time=5.880 min; HRMS: m/z (M+H)+=(Calculated for C$_{19}$H$_{22}$IN$_2$O$_4$S$_2$, 533.0060) found, 533.0072.

N-(4-((1,1-dioxidothiomorpholino)sulfonyl)phenyl)-3-iodo-4-methoxybenzamide (89)

Synthesize using Method C and thiomorpholine 1,1-dioxide as the starting material. $^1$H NMR (400 MHz, DMSO-d$_6$): δ 10.56 (s, 1H), 8.39 (d, J=2.2 Hz, 1H), 8.08-7.98 (m, 3H), 7.83-7.75 (m, 2H), 7.14 (d, J=8.8 Hz, 1H), 3.90 (s, 3H), 3.41 (dd, J=3.7, and 7.1 Hz, 4H), and 3.27-3.19 (m, 4H); Retention Time=5.177 min; HRMS: m/z (M+H)+=(Calculated for C$_{18}$H$_{20}$IN$_2$O$_6$S, 550.9802) found, 550.9811.

N-(4-(N-cyclopropylsulfamoyl)phenyl)-3-iodo-4-methoxybenzamide (11)

Synthesize using Method C and cyclopropanamine as the starting material. $^1$H NMR (400 MHz, DMSO-d$_6$) δ 10.47 (s, 1H), 8.39 (d, J=2.2 Hz, 1H), 8.12-7.92 (m, 3H), 7.87-7.66 (m, 3H), 7.13 (d, J=8.7 Hz, 1H), 3.90 (s, 3H), 2.22-1.93 (m, 1H), and 0.56-0.03 (m, 4H); Retention Time=5.337 min; HRMS: m/z (M+H)+=(Calculated for C$_{17}$H$_{18}$IN$_2$O$_4$S, 473.0026) found, 473.0047.

N-(4-(N,N-dipropylsulfamoyl)phenyl)-3-iodo-4-methoxybenzamide (48)

Synthesize using Method C and dipropylamine as the starting material. $^1$H NMR (400 MHz, DMSO-d$_6$): δ 10.46 (s, 1H), 8.38 (d, J=2.2 Hz, 1H), 8.05-7.91 (m, 3H), 7.79-7.70 (m, 2H), 7.13 (d, J=8.8 Hz, 1H), 3.90 (s, 3H), 3.03-2.94 (m, 4H), 1.51-1.37 (m, 4H), and 0.79 (t, J=7.4 Hz, 6H); Retention Time=6.522 min; HRMS: m/z (M+H)+=(Calculated for C$_{20}$H$_{26}$IN$_2$O$_4$S, 517.0652) found, 517.0642.

3-Iodo-4-methoxy-N-(4-(N-(pentan-3-yl)sulfamoyl)phenyl)benzamide (15)

Synthesize using Method C and pentan-3-amine as the starting material. $^1$H NMR (400 MHz, DMSO-d$_6$) δ 10.42 (s, 1H), 8.38 (d, J=2.2 Hz, 1H), 8.01 (dd, J=2.2, and 8.6 Hz, 1H), 7.95-7.87 (m, 2H), 7.78-7.69 (m, 2H), 7.35 (d, J=8.0 Hz, 1H), 7.13 (d, J=8.8 Hz, 1H), 3.89 (s, 3H), 2.90 (h, J=6.6 Hz, 1H), 1.39-1.13 (m, 4H), and 0.64 (t, J=7.4 Hz, 6H); Retention Time=5.971 min; HRMS: m/z (M+Na)+=(Calculated for C$_{19}$H$_{23}$IN$_2$NaO$_4$S, 525.0315) found, 525.0318.

3-Iodo-4-methoxy-N-(4-((2-(methoxymethyl)pyrrolidin-1-yl)sulfonyl)phenyl)benzamide (79)

Synthesize using Method C and 2-(methoxymethyl)pyrrolidine as starting material. $^1$H NMR (400 MHz, DMSO-d$_6$,): δ 10.49 (s, 1H), 8.38 (d, J=2.2 Hz, 1H), 8.05-7.94 (m, 3H), 7.83-7.76 (m, 2H), 7.13 (d, J=8.8 Hz, 1H), 3.90 (s, 3H), 3.64 (tt, J=3.4, and 7.5 Hz, 1H), 3.45 (dd, J=3.8, and 9.3 Hz, 1H), 3.36-3.20 (m, 2H), 3.25 (s, 3H), 3.05 (dt, J=7.0, and 10.0 Hz, 1H), 1.82-1.62 (m, 2H), 1.49-1.37 (m, 1H), and 1.43 (s, 1H); Retention Time=5.783 min; HRMS: m/z (M+Na)+=(Calculated for C$_{20}$H$_{23}$IN$_2$NaO$_5$S, 553.0265) found, 553.0269.

3-Iodo-4-methoxy-N-(4-((2-phenylpiperidin-1-yl)sulfonyl)phenyl)benzamide (90)

Synthesize using Method C and 2-phenylpiperidine as the starting material. $^1$H NMR (400 MHz, DMSO-d$_6$): δ 10.44 (s, 1H), 8.40 (d, J=2.2 Hz, 1H), 8.08-7.94 (m, 3H), 7.89-7.78 (m, 2H), 7.42-7.29 (m, 4H), 7.27-7.22 (m, 1H), 7.13 (d, J=8.7 Hz, 1H), 5.15 (d, J=5.1 Hz, 1H), 3.91 (s, 3H), 3.79-3.65 (m, 1H), 3.03-2.83 (m, 1H), 2.16 (d, J=14.0 Hz, 1H), 1.60-1.29 (m, 3H), and 1.29-0.99 (m, 2H); Retention Time=6.715 min; HRMS: m/z (M+H)+=(Calculated for C$_{25}$H$_{26}$IN$_2$O$_4$S, 577.0652) found, 577.0666.

3-Iodo-N-(4-((2-isopropylpiperidin-1-yl)sulfonyl)phenyl)-4-methoxybenzamide (85)

Synthesize using Method C and 2-isopropylpiperidine as the starting material. $^1$H NMR (400 MHz, DMSO-d$_6$): δ 10.41 (s, 1H), 8.39 (d, J=2.2 Hz, 1H), 8.05-7.90 (m, 3H), 7.81-7.74 (m, 2H), 7.13 (d, J=8.9 Hz, 1H), 3.90 (s, 3H), 3.67 (dd, J=4.4, and 14.5 Hz, 1H), 3.44 (dd, J=4.9, and 10.6 Hz, 1H), 3.04-2.78 (m, 1H), 2.05 (dq, J=6.6, and 10.7 Hz, 1H), 1.59 (d, J=13.9 Hz, 1H), 1.49-1.27 (m, 3H), 1.16-0.89 (m, 2H), and 0.84 (dd, J=6.0, and 18.0 Hz, 6H); Retention Time=6.686 min; HRMS: m/z (M+H)+=(Calculated for C$_{23}$H$_{28}$IN$_2$O$_4$S, 543.0809) found, 543.0805.

3-Iodo-N-(4-((2-isopropylpyrrolidin-1-yl)sulfonyl)phenyl)-4-methoxybenzamide (88)

Synthesize using Method C and isopropylpyrrolidine as the starting material. $^1$H NMR (400 MHz, DMSO-d$_6$): δ 10.48 (s, 1H), 8.38 (d, J=2.2 Hz, 1H), 8.05-7.93 (m, 3H), 7.83-7.74 (m, 2H), 7.13 (d, J=8.9 Hz, 1H), 3.90 (s, 3H), 3.42 (ddd, J=4.6, 5.7, and 8.1 Hz, 1H), 3.30-3.11 (m, 2H), 2.04-1.89 (m, 1H), 1.67-1.49 (m, 2H), 1.42-1.28 (m, 1H), 1.27-1.14 (m, 1H), and 0.84 (dd, J=6.9, and 18.8 Hz, 6H); Retention Time=6.494 min; HRMS: m/z (M+H)+=(Calculated for C$_{21}$H$_{26}$IN$_2$O$_4$S, 529.0652) found, 529.0659.

N-(4-((2-ethylpiperidin-1-yl)sulfonyl)phenyl)-3-iodo-4-methoxybenzamide (82)

Synthesize using Method C and 2-ethylpiperidine as the starting material. $^1$H NMR (400 MHz, DMSO-d$_6$): δ 10.46 (s, 1H), 8.39 (d, J=2.2 Hz, 1H), 8.05-7.91 (m, 3H), 7.81-7.74 (m, 2H), 7.13 (d, J=8.8 Hz, 1H), 3.90 (s, 3H), 3.80 (p, J=7.1

Hz, 1H), 3.63 (dd, J=4.2, and 14.3 Hz, 1H), 3.00-2.88 (m, 1H), 1.65-1.46 (m, 1H), 1.50-1.36 (m, 3H), 1.35 (s, 1H), 1.35-1.15 (m, 2H), 1.08-0.93 (m, 1H), and 0.78 (t, J=7.4 Hz, 3H); Retention Time=6.409 min; HRMS: m/z (M+H)+= (Calculated for $C_{21}H_{26}IN_2O_4S$, 529.0652) found, 529.0673. The enantiomers were separated using Column: CHIRAL-PAK AS, Mobile Phase: MeOH 100%, at 35 mL/min to give the enantiomers at a >95% purity.

Methyl-1-((4-(3-iodo-4-methoxybenzamido)phenyl) sulfonyl)piperidine-2-carboxylate (87)

Synthesize using Method C and methylpiperidine-2-carboxylate as the starting material. $^1$H NMR (400 MHz, DMSO-$d_6$): δ 10.45 (d, J=17.0 Hz, 1H), 8.39 (d, J=2.2 Hz, 1H), 8.09-7.90 (m, 3H), 7.79-7.63 (m, 2H), 7.13 (d, J=8.8 Hz, 1H), 4.68-4.52 (m, 1H), 3.90 (d, J=1.8 Hz, 3H), 3.62 (d, J=12.8 Hz, 1H), 3.51 (d, J=3.1 Hz, 3H), 3.18-3.01 (m, 1H), 1.94 (d, J=13.4 Hz, 1H), 1.62-1.46 (m, 2H), and 1.31-1.06 (m, 3H); Retention Time=5.959 min; HRMS: m/z (M+Na)+ =(Calculated for $C_{21}H_{23}IN_2NaO_6S$, 581.0234) found, 581.0214.

N-(4-((2-ethylpyrrolidin-1-yl)sulfonyl)phenyl)-3-iodo-4-methoxybenzamide (91)

Synthesize using Method C and 2-ethylpyrrolidine as the stating material. $^1$H NMR (400 MHz, DMSO-$d_6$): δ 10.48 (s, 1H), 8.38 (d, J=2.2 Hz, 1H), 8.05-7.93 (m, 3H), 7.82-7.74 (m, 2H), 7.13 (d, J=8.8 Hz, 1H), 3.90 (s, 3H), 3.45 (tt, J=4.6, and 9.0 Hz, 1H), 3.32-3.19 (m, 1H), 3.18-3.06 (m, 1H), 1.75-1.60 (m, 1H), 1.55-1.43 (m, 2H), 1.47-1.26 (m, 3H), and 0.84 (t, J=7.4 Hz, 3H); Retention Time=6.201 min; HRMS: m/z (M+H)+=(Calculated for $C_{20}H_{24}IN_2O_4S$, 515.0496) found, 515.0489.

3-Iodo-4-methoxy-N-(4-((4-methylpiperazin-1-yl) sulfonyl)phenyl)benzamide, TFA (9)

Synthesize using Method C and 4-methylpiperazine. $^1$H NMR (400 MHz, DMSO-$d_6$): δ 10.52 (s, 1H), 8.39 (d, J=2.2 Hz, 1H), 8.01 (dt, J=2.0, and 8.9 Hz, 3H), 7.69 (d, J=8.6 Hz, 2H), 7.13 (d, J=8.8 Hz, 1H), 3.90 (d, J=1.6 Hz, 3H), 2.85 (s, 4H), 2.34 (s, 4H), and 2.12 (s, 3H); Retention Time=4.003 min; HRMS: m/z (M+H)+=(Calculated for $C_{19}H_{23}IN_3O_4S$, 516.0448) found, 516.0469.

N-(4-((3,4-dimethylpiperazin-1-yl)sulfonyl)phenyl)-3-iodo-4-methoxy benzamide (93)

Synthesize using Method C and 3,4-dimethylpiperazine as the starting material. $^1$H NMR (400 MHz, DMSO-$d_6$): δ 10.51 (s, 1H), 8.39 (d, J=2.2 Hz, 1H), 8.06-7.97 (m, 3H), 7.73-7.66 (m, 2H), 7.14 (d, J=8.7 Hz, 1H), 3.90 (s, 3H), 3.43-3.28 (m, 2H), 2.71 (dt, J=2.9, and 11.6 Hz, 1H), 2.39-2.29 (m, 1H), 2.10 (s, 3H), 2.19-2.02 (m, 1H), 1.95 (dd, J=9.8, and 11.0 Hz, 1H), and 0.92 (d, J=6.1 Hz, 3H); Retention Time=4.449 min; HRMS: m/z (M+Na)+=(Calculated for $C_{20}H_{24}IN_3NaO_4S$, 552.0424) found, 552.0447.

N-(4-((4-ethyl-2-methylpiperazin-1-yl)sulfonyl)phenyl)-3-iodo-4-methoxybenzamide, NH$_4^+$ (95)

Synthesize using Method C and 4-ethyl2-methylpiperazine as the starting material. $^1$H NMR (400 MHz, DMSO-$d_6$): δ 10.47 (s, 1H), 8.39 (d, J=2.2 Hz, 1H), 8.05-7.92 (m, 3H), 7.78-7.71 (m, 2H), 7.13 (d, J=8.8 Hz, 1H), 3.90 (s, 3H), 3.53-3.44 (m, 1H), 3.18-3.02 (m, 1H), 2.72-2.64 (m, 1H), 2.53 (dt, J=2.0, and 11.3 Hz, 1H), 2.26-2.11 (m, 2H), 1.88 (dd, J=3.7, and 11.2 Hz, 1H), 1.75 (td, J=3.4 and 11.5, Hz, 2H), 1.04 (d, J=6.7 Hz, 3H), and 0.90 (t, J=7.2 Hz, 3H); Retention Time=4.204 min; HRMS: m/z (M+H)+=(Calculated for $C_{21}H_{27}IN_3O_4S$, 544.0761) found, 544.0766.

N-(4-((2,4-dimethylpiperazin-1-yl)sulfonyl)phenyl)-3-iodo-4-methoxybenzamide, NH$_4^+$ (96)

Synthesize using Method C and 2,4-dimethylpiperazine as the starting material. $^1$H NMR (400 MHz, DMSO-$d_6$): δ 10.47 (s, 1H), 8.39 (d, J=2.2 Hz, 1H), 8.05-7.92 (m, 3H), 7.79-7.71 (m, 2H), 7.13 (d, J=8.8 Hz, 1H), 3.90 (s, 3H), 3.52-3.44 (m, 1H), 3.18-3.02 (m, 1H), 2.60 (d, J=11.5 Hz, 1H), 2.48-2.41 (m, 1H), 2.05 (s, 3H), 1.87 (dd, J=3.8, and 11.3 Hz, 1H), 1.72 (td, J=3.5, and 11.5 Hz, 2H), and 1.04 (d, J=6.7 Hz, 3H); Retention Time=4.378 min; HRMS: m/z (M+H)+=(Calculated for $C_{20}H_{25}IN_3O_4S$, 530.0605) found, 530.0613.

3-Iodo-4-methoxy-N-(4-(N-(tetrahydro-2H-pyran-4-yl)sulfamoyl)phenyl)benzamide (84)

Synthesize using Method C and tetrahydro-2H-pyran-4-amine, 2HCl as the starting material. $^1$H NMR (400 MHz, DMSO-$d_6$): δ 10.44 (s, 1H), 8.38 (d, J=2.2 Hz, 1H), 8.01 (dd, J=2.2, and 8.6 Hz, 1H), 7.96-7.89 (m, 2H), 7.81-7.74 (m, 2H), 7.65 (d, J=7.3 Hz, 1H), 7.13 (d, J=8.8 Hz, 1H), 3.90 (s, 3H), 3.69 (dt, J=3.8, and 11.7 Hz, 2H), 3.32-3.07 (m, 4H), 1.53-1.44 (m, 1H), and 1.40-1.25 (m, 2H); Retention Time=4.977 min; HRMS: m/z (M+H)+=(Calculated for $C_{19}H_{22}IN_2O_5S$, 517.0289) found, 517.0295.

3-Iodo-4-methoxy-N-(4-((3-methyl-3,8-diazabicyclo [3.2.1]octan-8-yl)sulfonyl)phenyl) benzamide, NH$_4^+$ (81)

Synthesize using Method C and 3-methyl-3,8-diazabicyclo[3.2.1]octane as the starting material. $^1$H NMR (400 MHz, DMSO-$d_6$): δ 10.54 (s, 1H), 9.23 (s, 1H), 8.39 (d, J=2.2 Hz, 1H), 8.00 (td, J=1.8, and 8.9 Hz, 3H), 7.86 (d, J=8.5 Hz, 2H), 7.14 (d, J=8.8 Hz, 1H), 4.37 (s, 2H), 3.90 (s, 3H), 3.18 (s, 2H), 2.75 (s, 3H), 2.20 (s, 1H), 1.76 (d, J=9.9 Hz, 2H), and 1.41 (s, 2H); Retention Time=4.398 min; HRMS: m/z (M+H)+=(Calculated for $C_{21}H_{25}IN_3O_4S$, 542.0605) found, 542.0596.

N-(4-((2,6-dimethylpiperidin-1-yl)sulfonyl)phenyl)-3-iodo-4-methoxybenzamide, NH$_4^+$ (111)

Synthesize using Method C and 2,6-dimethylpiperidine as the starting material. $^1$H NMR (400 MHz, DMSO-$d_6$) δ: 10.46 (s, 1H), 8.38 (d, J=2.2 Hz, 1H), 8.01 (dd, J=2.3, and 8.6 Hz, 1H), 7.98-7.90 (m, 2H), 7.80-7.72 (m, 2H), 7.13 (d, J=8.8 Hz, 1H), 4.06 (h, J=6.4 Hz, 2H), 3.90 (s, 3H), 3.33-3.23 (m, 1H), 1.74-1.58 (m, 1H), 1.37 (d, J=13.3 Hz, 2H), and 1.24 (d, J=7.1 Hz, 8H); Retention Time=6.417 min; HRMS: m/z (M+Na)+=(Calculated for $C_{21}H_{25}IN_2NaO_4S$, 551.0472) found, 551.0481.

3-Iodo-4-methoxy-N-(4-((2-methyl-4-oxopiperidin-1-yl)sulfonyl)phenyl)benzamide

Synthesize using Method C and 2-methylpiperidin-4-one as the starting material. $^1$H NMR (400 MHz, DMSO-$d_6$): δ 10.50 (s, 1H), 8.38 (d, J=2.2 Hz, 1H), 8.04-7.90 (m, 3H), 7.87-7.79 (m, 2H), 7.11 (dd, J=8.7, and 13.3 Hz, 1H), 4.43-4.35 (m, 1H), 3.89 (d, J=3.7 Hz, 4H), 3.41-3.30 (m, 1H), 2.53 (dd, J=6.5, and 14.5 Hz, 1H), 2.37 (ddd, J=7.1, 11.3, and 15.3 Hz, 1H), 2.18 (d, J=15.7 Hz, 1H), 2.12-2.02 (m, 1H), and 0.95 (d, J=6.8 Hz, 3H); Retention Time=5.199 min; HRMS: m/z (M+H)+=(Calculated for $C_{20}H_{22}IN_2O_5S$, 529.0289) found, 529.0298.

N-(4-((4-hydroxy-2-methylpiperidin-1-yl)sulfonyl) phenyl)-3-iodo-4-methoxybenzamide (110)

Follow the synthesis for 3-iodo-4-methoxy-N-(4-((2-methyl-4-oxopiperidin-1-yl)sulfonyl) phenyl)benzamide. 3-Iodo-4-methoxy-N-(4-((2-methyl-4-oxopiperidin-1-yl) sulfonyl)phenyl) benzamide (0.13 g, 0.25 mmol), was stirred in EtOH (2.5 mL) and treated with sodium borohydride (0.03 g, 0.75 mmol) at room temp. This reaction was stirred for 3 hrs. at which time the reaction pH was adjusted with 1 N HCl. The reaction was concentrated and purified on reverse phase to give the desired compound as a mixture of diastereomers. $^1$H NMR (400 MHz, DMSO-$d_6$): δ 10.46 (d, J=3.0 Hz, 1H), 8.38 (d, J=2.2 Hz, 1H), 8.04-7.90 (m, 3H), 7.75 (dd, J=1.8, and 8.9 Hz, 2H), 7.12 (d, J=8.7 Hz, 1H), 4.61 (dd, J=2.1, and 3.7 Hz, 1H), 3.89 (s, 3H), 3.86-3.61 (m, 2H), 3.34 (t, J=5.8 Hz, 1H), 1.61-1.48 (m, 2H), 1.48-1.39 (m, 2H), 1.30-1.18 (m, 1H), and 1.17-0.91 (m, 3H); Retention Time=4.877 and 4.964 min; HRMS: m/z (M+H)+=(Calculated for $C_{20}H_{24}IN_2O_5S$, 531.0445) found, 531.0459.

4-Bromo-N-(4-(N,N-dipropylsulfamoyl)phenyl)-3-iodobenzamide (94)

Synthesize using Method C and N,N-dipropylamine HCl as the starting material, and 4-bromo-3-iodobenzoyl chloride as the acid chloride. $^1$H NMR (400 MHz, DMSO-$d_6$): δ 10.65 (s, 1H), 8.46 (dd, J=0.5, and 2.0 Hz, 1H), 7.98-7.91 (m, 2H), 7.95-7.81 (m, 2H), 7.80-7.72 (m, 2H), 3.03-2.94 (m, 4H), 1.51-1.37 (m, 4H), and 0.79 (t, J=7.4 Hz, 6H); Retention Time=6.906 min; HRMS: m/z (M+H)+=(Calculated for $C_{19}H_{23}BrIN_2O_3S$, 564.9652) found, 564.9663.

4-Bromo-3-iodo-N-(4-((2-methylpiperidin-1-yl) sulfonyl)phenyl)benzamide (73)

Synthesize using Method C and 2-methylpiperidine as the starting material and 4-bromo-3-iodobenzoyl chloride as the acid chloride. $^1$H NMR (400 MHz, DMSO-$d_6$): δ 10.65 (s, 1H), 8.45 (dd, J=0.5, and 2.0 Hz, 1H), 7.98-7.90 (m, 2H), 7.95-7.81 (m, 2H), 7.81-7.72 (m, 2H), 4.06 (s, 1H), 3.57 (d, J=11.0 Hz, 1H), 2.93 (td, J=2.7, and 13.0 Hz, 1H), 1.54-1.45 (m, 1H), 1.49-1.35 (m, 1H), 1.38 (s, 3H), 1.24-1.10 (m, 1H), and 0.97 (d, J=6.9 Hz, 3H); Retention Time=6.646 min; HRMS: m/z (M+H)+=(Calculated for $C_{19}H_{21}BrIN_2O_3S$, 564.9476) found, 564.9479.

4-Bromo-3-iodo-N-(4-((2-(trifluoromethyl)piperidin-1-yl)sulfonyl)phenyl)benzamide (109)

Synthesize using Method C and 2-trifluoromethylpiperidine as the starting material and 4-bromo-3-iodobenzoyl chloride as the acid chloride. $^1$H NMR (DMSO-$d_6$, 400 MHz): δ 10.71 (s, 1H), 8.45 (d, J=2.0 Hz, 1H), 8.02-7.93 (m, 2H), 7.94-7.81 (m, 4H), 4.74 (s, 1H), 3.69 (dd, J=4.4, and 14.5 Hz, 1H), 3.03 (t, J=13.9 Hz, 1H), 1.80 (d, J=11.8 Hz, 1H), 1.40 (d, J=14.6 Hz, 4H), and 0.77 (d, J=12.2 Hz, 1H); Retention Time=6.765 min; HRMS: m/z (M+H)+=(Calculated for $C_{19}H_{18}BrF_3IN_2O_3S$, 618.9194) found, 618.9168.

4-Bromo-3-iodo-N-(4-((2-propylpiperidin-1-yl) sulfonyl)phenyl)benzamide (97)

Synthesize using Method C and 2-propylpiperidine as the starting material and 4-bromo-3-iodobenzoyl chloride as the acid chloride. $^1$H NMR (400 MHz, DMSO-$d_6$): δ 10.65 (s, 1H), 8.46 (dd, J=0.5, and 1.9 Hz, 1H), 7.98-7.90 (m, 2H), 7.92-7.81 (m, 2H), 7.83-7.74 (m, 2H), 3.93-3.85 (m, 1H), 3.66-3.57 (m, 2H), 3.36-3.23 (m, 2H), 2.95 (t, J=12.4 Hz, 1H), 1.61-1.11 (m, 6H), 0.99 (ddt, J=4.4, 8.7, and 13.2 Hz, 1H), and 0.84 (t, J=7.3 Hz, 3H); Retention Time=7.158 min; HRMS: m/z (M+H)+=(Calculated for $C_{21}H_{25}BrIN_2O_3S$, 592.7803) found, 592.9790.

4-Bromo-N-(4-((4,4-difluoropiperidin-1-yl)sulfonyl) phenyl)-3-iodobenzamide (112)

Synthesize using Method C and 4,4-difluoropiperidine as the starting material and 4-bromo-3-iodobenzoyl chloride as the acid chloride. $^1$H NMR (400 MHz, DMSO-$d_6$): δ 10.72 (s, 1H), 8.45 (dd, J=0.4, and 2.0, Hz, 1H), 8.05-7.97 (m, 2H), 7.92-7.81 (m, 2H), 7.80-7.72 (m, 2H), 3.03 (d, J=5.9 Hz, 4H), and 2.03 (ddt, J=5.8, 13.5, and 19.7 Hz, 4H); Retention Time=6.299 min; HRMS: m/z (M+H)+=(Calculated for $C_{21}H_{25}BrIN_2O_3S$, 592.7803) found, 592.9790.

3-Iodo-4-methoxy-N-(4-(morpholinosulfonyl)phenyl)benzamide (5)

Synthesize using Method C and morpholine as the starting material and 4-methoxy-3-iodobenzoyl chloride as the acid chloride. $^1$H NMR (400 MHz DMSO-$d_6$): δ 10.53 (s, 1H), 8.39 (d, J=2.3 Hz, 1H), 8.07-7.98 (m, 3H), 7.74-7.66 (m, 2H), 7.14 (d, J=8.8 Hz, 1H), 3.90 (s, 3H), 3.61 (dd, J=5.5, 3.8 Hz, 4H), and 2.83 (dd, J=3.8, and 5.7 Hz, 4H):); Retention Time=5.342 min; HRMS: m/z (M+Na)+=(Calculated for $C_{18}H_{19}IN_2NaO_5S$, 524.9952) found, 524.9974.

4-Bromo-3-iodo-N-(4-((3-methylmorpholino)sulfonyl)phenyl)benzamide (113)

Synthesize using Method C and 3-methylmorpholine as the starting material and 4-bromo-3-iodobenzoyl chloride as the acid chloride. Retention Time=5.955 min; HRMS: m/z (M+H)+=(Calculated for $C_{18}H_{19}BrIN_2O_4S$, 566.9269) found, 566.9254.

4-bromo-3-iodo-N-(4-((3-isopropylmorpholino) sulfonyl)phenyl)benzamide (114)

Synthesize using Method C and 3-isopropylmorpholine as the starting material and 4-bromo-3-iodobenzoyl chloride as the acid chloride. $^1$H NMR (400 MHz DMSO-$d_6$): δ 10.67 (s, 1H), 8.46 (dd, J=0.5, and 1.9 Hz, 1H), 8.00-7.91 (m, 2H), 7.92-7.78 (m, 3H), 7.77 (s, 1H), 3.70 (d, J=12.0 Hz, 1H), 3.54-3.43 (m, 1H), 3.30-3.11 (m, 2H), 2.97-2.79 (m, 2H), 2.22-2.07 (m, 1H), 2.04 (s, 1H), and 0.87 (dd, J=6.7, and 9.0 Hz, 6H); Retention Time=6.426 min; HRMS: m/z (M+H)+=(Calculated for $C_{20}H_{23}BrIN_2O_4S$, 594.9582) found, 594.9583.

3-Iodo-4-methoxy-N-(4-(N-phenylsulfamoyl)phenyl)benzamide (29)

Synthesize using Method C and aniline as the starting material. $^1$H NMR (400 MHz, DMSO-$d_6$) δ 7.80-7.68 (m, 1H), 7.49-7.38 (m, 3H), 7.38-7.26 (m, 3H), 7.24-7.06 (m, 2H), 6.80 (d, J=8.8 Hz, 1H), 6.65-6.50 (m, 2H), 6.25 (s, 2H), and 3.74 (s, 3H); Retention Time=5.378 min; HRMS: m/z (M+H)+=(Calculated for $C_{20}H_{18}IN_2O_4S$, 509.0026) found, 509.0044.

3-Iodo-4-methoxy-N-(4-(N-(3-(trifluoromethyl)phenyl)sulfamoyl)phenyl)benzamide, $NH_4^+$ (24)

Synthesize using Method C and 3-trifluoromethylaniline as the starting material. $^1$H NMR (DMSO-$d_6$, 400 MHz) δ 7.80 (d, J=2.2 Hz, 1H), 7.74 (s, 1H), 7.77-7.66 (m, 1H), 7.56-7.38 (m, 4H), 7.39-7.31 (m, 1H), 6.82 (d, J=8.8 Hz, 1H), 6.62-6.54 (m, 2H), 6.31 (s, 2H), and 3.75 (s, 3H); Retention Time=5.774 min; HRMS: m/z (M+Na)+=(Calculated for $C_{21}H_{16}F_3IN_2NaO4S$, 598.9720) found, 598.9734.

N-(4-(N-(2,3-dimethylphenyl)sulfamoyl)phenyl)-3-iodo-4-methoxybenzamide (27)

Synthesize using Method C and 2,3-dimethylaniline as the starting material. $^1$H NMR (400 MHz, DMSO-$d_6$) δ 7.60 (d, J=2.2 Hz, 1H), 7.55-7.47 (m, 2H), 7.28 (dd, J=2.2, and 8.7 Hz, 1H), 7.17-7.10 (m, 1H), 7.04 (t, J=7.7 Hz, 1H), 6.91 (d, J=7.4 Hz, 1H), 6.78 (d, J=8.7 Hz, 1H), 6.64-6.55 (m, 2H), 6.28 (s, 2H), 3.73 (s, 3H), 2.17 (s, 3H), and 2.04 (s, 3H); Retention Time=5.733 min; HRMS: m/z (M+H)+=(Calculated for $C_{22}H_{22}IN_2O_4S$, 537.0339) found, 537.0356.

3-Iodo-4-methoxy-N-(4-((2-methylpiperidin-1-yl)sulfonyl)phenyl)benzimidamide, TFA (117)

Synthesize using Method C and 2-methylpiperidine as the starting material. To a stirred solution of 4-((2-methylpiperidin-1-yl)sulfonyl)aniline, HCl (0.16 g, 0.55 mmol), in DMF (1.0 mL), was added NaH (95%) (0.04 g, 1.65 mmol) and let stir at rt for 30 min before adding 3-iodo-4-methoxybenzonitrile (0.17 g, 0.66 mmol). The reaction mixture was stirred for 8 h, and quenched with water followed by EtOAc, the organic layer was washed with brine, dried over MgSO$_4$, filtered, concentrated, and purified to give the desired material. $^1$H NMR (400 MHz, DMSO-$d_6$): δ 8.33 (s, 1H), 7.92 (s, 1H), 7.63 (d, J=8.5 Hz, 2H), 7.02 (d, J=8.7 Hz, 1H), 6.94 (d, J=8.1 Hz, 2H), 4.06 (p, J=5.5 Hz, 1H), 3.85 (s, 3H), 3.68-3.44 (m, 1H), 2.93 (t, J=8.0 Hz, 1H), 1.56-1.32 (m, 6H), 1.31-1.12 (m, 1H), and 0.99 (d, J=6.9 Hz, 3H); Retention Time=4.471 min; HRMS: m/z (M+H)+=(Calculated for $C_{20}H_{25}IN_3O_3S$, 514.0656) found, 514.0650.

N-(3-Iodo-4-methoxybenzyl)-4-((2-methylpiperidin-1-yl)sulfonyl)aniline, TFA (116)

Synthesize using Method C using 2-methylpiperidine as the starting material. 4-((2-methylpiperidin-1-yl)sulfonyl)aniline (0.17 g, 0.67 mmol), and 3-iodo-4-methoxybenzaldehyde (0.26 g, 1.00 mmol), in EtOH (4.00 mL) underwent a rapid reflux for 18 h to form the imine. The reaction was cooled to rt before the addition of NaBH$_4$ (0.08 g, 2.00 mmol) and let stir for 4 h before quenching with saturated bicarb and MeOH. The mixture was allowed to stir for 30 min before concentrating. The solid was taken up in EtOAc, filtered, and washed with water and brine. The organic layer was dried with MgSO$_4$, filtered, concentrated, and purified to give the desired product. $^1$H NMR (400 MHz, DMSO-$d_6$): δ 7.71 (d, J=2.1 Hz, 1H), 7.45-7.35 (m, 2H), 7.31 (dd, J=2.2, and 8.4 Hz, 1H), 7.02 (t, J=6.0 Hz, 1H), 6.94 (d, J=8.5 Hz, 1H), 6.67-6.56 (m, 2H), 4.22 (d, J=5.9 Hz, 2H), 3.97 (dd, J=4.5, and 7.1 Hz, 1H), 3.77 (s, 3H), 3.44 (dd, J=3.8, and 12.6, Hz, 1H), 2.84 (m, 2H), 1.50-1.32 (m, 3H), 1.27-1.10 (m, 2H), and 0.94 (d, J=6.9 Hz, 3H); Retention Time=6.431 min; HRMS: m/z (M+H)+=(Calculated for $C_{20}H_{26}IN_2O_3S$, 501.0703) found, 501.0728.

4-Bromo-3-cyano-N-(4-((2-methylpiperidin-1-yl)sulfonyl)phenyl)benzamide (115)

Synthesize using Method C using 2-methylpiperidine as the starting material and 4-bromo-3-cyanobenzoyl chloride as the acid chloride. This acid chloride was synthesized in the following manner. 4-bromo-3-cyanobenzoic acid (0.10 g, 0.44 mmol), and oxalyl chloride (0.05 mL, 0.58 mmol) was stirred in DCM (0.44 mL) at rt before DMF (2.0 µl, 0.03 mmol) was added. The mixture was stirred at rt for 72 h, at which time the reaction was concentrate to a white solid. The white solid was used as is in the next reaction by making a 1 M solution in dry DCM. 1H NMR (400 MHz DMSO-$d_6$): δ 10.75 (s, 1H), 8.68-8.32 (m, 1H), 8.13 (dd, J=2.2, and 8.5 Hz, 1H), 8.08-8.03 (m, 1H), 7.97-7.90 (m, 2H), 7.81-7.75 (m, 2H), 4.08 (dd, J=3.7, and 7.1 Hz, 1H), 3.73-3.47 (m, 1H), 2.93 (td, J=2.7, and 13.0 Hz, 1H), 1.61-1.30 (m, 5H), 1.30-1.01 (m, 1H), and 0.97 (d, J=6.9 Hz, 3H); Retention Time=6.234 min; HRMS: m/z (M+H)+=(Calculated for $C_{20}H_{21}BrN_3O_3S$, 464.0463) found, 464.0451.

4-Bromo-3-ethynyl-N-(4-((2-methylpiperidin-1-yl)sulfonyl)phenyl)benzamide (119)

Synthesize using Method C using 2-methylpiperidine as the starting material and 4-bromo-3-iodobenzoyl chloride as the acid chloride. Chill 4-bromo-3-iodo-N-(4-((2-methylpiperidin-1-yl)sulfonyl)phenyl)benzamide (0.20 g, 0.36 mmol), bis(triphenylphosphine)palladium(II) chloride (7.50 mg, 10.65 µmol), copper(I) iodide (4.00 mg, 0.02 mmol), TEA (0.500 mL, 3.55 mmol), and triphenylphosphine (5.60 mg, 0.02 mmol) in degasses THF (1.00 mL). Add ethynyltrimethylsilane (0.05 mL, 0.37 mmol), at 0° C. and take out of ice bath and let stir for 4 h at rt. When the reaction was complete thiol resin was added and stirred for 2 h at rt. The reaction was filtered through celite, and concentrated. The crude material was placed on normal phase silica column with Hex/EtOAc 0 to 70%. 4-Bromo-N-(4-((2-methylpiperidin-1-yl)sulfonyl)phenyl)-3-((trimethylsilyl)ethynyl)benzamide (0.12 g, 0.23 mmol), and K$_2$CO$_3$ (0.03 g, 0.23 mmol) was stirred in MeOH (3.0 mL) for 3 hr at rt. The reactions was concentrated and turned in for purification. $^1$H NMR (400 MHz, DMSO-$d_6$) δ: 10.67 (s, 1H), 8.15 (dd, J=0.6, and 2.1 Hz, 1H), 7.99-7.91 (m, 2H), 7.96-7.81 (m, 2H), 7.81-7.72 (m, 2H), 4.71 (s, 1H), 4.10-4.03 (m, 1H), 3.61-3.51 (m, 1H), 2.92 (td, J=2.6, and 13.1 Hz, 1H), 1.62-1.24 (m, 5H), 1.23-1.09 (m, 1H), and 0.96 (d, J=6.9 Hz, 3H); Retention Time=5.914 min; HRMS: m/z (M+H)+=(Calculated for $C_{21}H_{22}BrN_2O_3S$, 463.051) found, 463.0502.

N-(4-((4-hydroxypiperidin-1-yl)sulfonyl)phenyl)-3-iodo-4-methoxybenzamide (54)

Piperidin-4-ol (0.05 g, 0.45 mmol), and pyridine (0.15 mL, 1.81 mmol) were stirred in THF (2.30 mL) before 4-nitrobenzene-1-sulfonyl chloride (0.10 g, 0.45 mmol) was added to the mixture. This mixture was stirred for 3 hr, concentrated under a stream of nitrogen to give 1-((4-nitrophenyl)sulfonyl)piperidin-4-ol and used as is for the next reaction. 1-((4-nitrophenyl)sulfonyl)piperidin-4-ol (0.13 g, 0.45 mmol), AcOH (0.08 mL, 1.35 mmol), zinc (0.09 g, 1.35 mmol) in MeOH (2.250 mL) were stirred for 18 h, filter wash with acetonitrile and place on 10/90 gradient water/acetonitrile (0.1% TFA) reverse phase for purification. Retention Time=2.148 min. 1-((4-aminophenyl)sulfonyl)piperidin-4-ol, TFA (1 equiv) was treated with DIPEA (3 equiv) in DCM (0.2M) and 1 M solution of 3-iodo-4-methoxybenzoyl chloride (1.5 equiv) in DCM was added to the reaction at rt. This mixture was allowed to stir overnight and was quenched after 18 h with MeOH. The reaction was concentrated and purified to give the targeted compound. $^1$H NMR (400 MHz, DMSO-d$_6$): δ 10.50 (s, 1H), 8.39 (d, J=2.2 Hz, 1H), 8.05-7.95 (m, 3H), 7.73-7.65 (m, 2H), 7.13 (d, J=8.8 Hz, 1H), 4.63 (d, J=3.9 Hz, 1H), 3.90 (s, 3H), 3.49 (dq, J=3.8, and 7.7 Hz, 1H), 3.22-2.99 (m, 2H), 2.68 (ddd, J=3.2, 8.3, and 11.4 Hz, 2H), 1.71 (ddd, J=3.7, 6.0, and 12.6 Hz, 2H), and 1.40 (dtd, J=3.6, 8.1, and 12.2 Hz, 2H); Retention Time=4.884 min; HRMS: m/z (M+Na)+=(Calculated for C$_{19}$H$_{21}$IN$_2$NaO$_5$S, 539.0108) found, 539.0121.

N-(4-(1,4-dioxa-8-azaspiro[4.5]decan-8-ylsulfonyl) phenyl)-3-iodo-4-methoxybenzamide (60)

Synthesize using Method D and 1,4-dioxa-8-azaspiro[4.5] decane as the starting material. Retention Time=4.884 min; HRMS: m/z (M+H)+=(Calculated for C$_{21}$H$_{24}$IN$_2$O$_6$S, 559.0394) found, 559.0390.

N-(4-((4-ethylpiperazin-1-yl)sulfonyl)phenyl)-3-iodo-4-methoxybenzamide, NH$_4$+ (57)

Synthesize using Method D and 1-ethylpiperazine as the starting material. The reduction of the nitro to the amine was done on an H-Cube pro flow reactor on a 70 mm Catcart of 10% Pd/C at 50° C. and 50 Barr at 0.9 mL/min on 0.1 M solution MeOH/EtOAc (1/1) for 2 h. The solvent was concentrated and the material was used as is in the next reaction. $^1$H NMR (400 MHz, DMSO-d$_6$): δ 10.52 (s, 1H), 8.39 (t, J=1.7 Hz, 1H), 8.05-7.97 (m, 3H), 7.73-7.65 (m, 2H), 7.17-7.10 (m, 1H), 3.90 (d, J=1.5 Hz, 3H), 2.84 (s, 4H), 2.38 (s, 4H), 2.32-2.23 (m, 2H), and 0.90 (t, J=7.2 Hz, 3H); Retention Time=4.161 min; HRMS: m/z (M+H)+=(Calculated for C$_{20}$H$_{25}$IN$_3$O$_4$S, 530.0605) found, 530.0610.

N-(4-(N-(2-(cyclohex-1-en-1-yl)ethyl)sulfamoyl) phenyl)-3-iodo-4-methoxybenzamide (45)

Synthesize using Method D and 2-(cyclohex-1-en-1-yl) ethanamine as the starting material and the zinc reduction of the nitro group. $^1$H NMR (400 MHz, DMSO-d$_6$): δ 10.45 (s, 1H), 8.39 (d, J=2.2 Hz, 1H), 8.05-7.89 (m, 3H), 7.78-7.69 (m, 2H), 7.38 (t, J=5.9 Hz, 1H), 7.13 (d, J=8.8 Hz, 1H), 5.30 (dd, J=1.7, and 3.3, Hz, 1H), 3.90 (s, 3H), 2.81-2.71 (m, 2H), 1.96 (s, 1H), 2.00-1.91 (m, 1H), 1.90-1.84 (m, 2H), 1.77-1.69 (m, 2H), and 1.54-1.37 (m, 4H); Retention Time=6.455 min; HRMS: m/z (M+H)+=(Calculated for C$_{22}$H$_{26}$IN$_2$O$_4$S, 541.0652) found, 541.0656.

N-(4-((2-(hydroxymethyl)pyrrolidin-1-yl)sulfonyl) phenyl)-3-iodo-4-methoxybenzamide (99)

Synthesize using Method D and pyrrolidin-2-ylmethanol as the starting material, and the zinc reduction. $^1$H NMR (400 MHz, DMSO-d$_6$): δ 10.49 (s, 1H), 8.39 (d, J=2.2 Hz, 1H), 8.05-7.94 (m, 3H), 7.84-7.73 (m, 2H), 7.13 (d, J=8.8 Hz, 1H), 4.78 (d, J=5.9 Hz, 1H), 3.90 (s, 3H), 3.57-3.44 (m, 2H), 3.28-3.20 (m, 2H), 3.03 (dt, J=7.2, and 10.0 Hz, 1H), 1.86-1.63 (m, 2H), and 1.48-1.32 (m, 1H); Retention Time=5.030 min; HRMS: m/z (M+H)+=(Calculated for C$_{19}$H$_{21}$IN$_2$O$_5$S, 517.0289) found, 517.0296.

3-Iodo-4-methoxy-N-(4-(N-(2-(pyrrolidin-1-yl) ethyl)sulfamoyl)phenyl)benzamide, TFA (69)

Synthesize using Method D and 2-(pyrrolidin-1-yl) ethanamine as the starting material. Retention Time=4.066 min; HRMS: m/z (M+H)+=(Calculated for C$_{20}$H$_{25}$IN$_3$O$_4$S, 530.0605) found, 530.0618.

3-Iodo-4-methoxy-N-(4-(N-(2-(piperidin-1-yl)ethyl) sulfamoyl)phenyl)benzamide, TFA (63)

Synthesize using Method D and 2-(piperidin-1-yl) ethanamine as the starting material. $^1$H NMR (400 MHz, DMSO-d$_6$): δ 10.49 (s, 1H), 9.03 (s, 1H), 8.39 (d, J=2.2 Hz, 1H), 8.05-7.93 (m, 3H), 7.78 (d, J=8.9 Hz, 2H), 7.13 (d, J=8.8 Hz, 1H), 3.90 (s, 3H), 3.46-3.35 (m, 2H), 3.14-3.01 (m, 4H), 2.96-2.82 (m, 2H), 1.83-1.72 (m, 2H), 1.60 (d, J=15.6 Hz, 3H), and 1.33 (d, J=12.5 Hz, 1H); Retention Time=4.155 min; HRMS: m/z (M+H)+=(Calculated for C$_{21}$H$_{27}$IN$_3$O$_4$S, 544.0786 found, 544.0786.

N-(4-(N-(2-(diethylamino)ethyl)sulfamoyl)phenyl)-3-iodo-4-methoxybenzamide, TFA (66)

Synthesize using Method D and N,N-diethylethane-1,2-diamine as the starting material. $^1$H NMR (400 MHz, DMSO-d$_6$): δ 10.50 (s, 1H), 9.05 (s, 1H), 8.39 (d, J=2.3 Hz, 1H), 8.05-7.94 (m, 3H), 7.79 (d, J=8.7 Hz, 2H), 7.13 (d, J=8.8 Hz, 1H), 3.90 (s, 3H), 3.23-2.91 (m, 8H), and 1.23-1.05 (m, 6H); Retention Time=4.140 min; HRMS: m/z (M+H)+=(Calculated for C$_{20}$H27IN$_3$O$_4$S, 532.0761) found, 532.0758.

N-(4-(azepan-1-ylsulfonyl)phenyl)-3-iodo-4-methoxybenzamide (70)

Synthesize using Method D and azepane as the starting material. $^1$H NMR (400 MHz, DMSO-d$_6$): δ 10.46 (s, 1H), 8.38 (d, J=2.2 Hz, 1H), 8.12-7.88 (m, 3H), 7.81-7.65 (m, 2H), 7.13 (d, J=8.8 Hz, 1H), 3.90 (s, 3H), 3.21-3.12 (m, 4H), 1.63-1.55 (m, 4H), and 1.47 (ddd, J=2.5, 3.5, and 7.1 Hz, 4H); Retention Time=6.292 min; HRMS: m/z (M+Na)+=(Calculated for C$_{20}$H$_{23}$IN$_2$NaO$_4$S, 537.0315) found, 537.0332.

3-Iodo-4-methoxy-N-(4-(N-(2-morpholinoethyl) sulfamoyl)phenyl)benzamide, TFA (78)

Synthesize using Method D and 2-morpholinoethanamine as the starting material. $^1$H NMR (400 MHz, DMSO-d$_6$): δ 10.49 (s, 1H), 9.68 (s, 1H), 8.39 (d, J=2.2 Hz, 1H), 8.05-7.93 (m, 3H), 7.83-7.74 (m, 2H), 7.13 (d, J=8.8 Hz, 1H), 3.90 (s, 5H), 3.73-3.56 (m, 2H), and 3.23-3.13 (m, 8H); Retention Time=4.022 min; HRMS: m/z (M+Na)+=(Calculated for C$_{20}$H$_{24}$IN$_3$NaO$_5$S, 568.0374) found, 568.0387.

3-Iodo-4-methoxy-N-(4-((4-(pyrimidin-2-yl)piperazin-1-yl)sulfonyl)phenyl)benzamide, NH$_4$+ (75)

Synthesize using Method D and 2-(piperazin-1-yl)pyrimidine, 2HCl as starting material. $^1$H NMR (400 MHz, DMSO-d$_6$): δ 10.50 (s, 1H), 8.37 (d, J=2.2 Hz, 1H), 8.30 (d, J=4.8 Hz, 2H), 8.03-7.95 (m, 3H), 7.74-7.67 (m, 2H), 7.12

(d, J=8.8 Hz, 1H), 6.60 (t, J=4.7 Hz, 1H), 3.89 (s, 3H), 3.80 (t, J=5.1 Hz, 4H), and 2.92 (t, J=5.1 Hz, 4H); Retention Time=5.645 min; HRMS: m/z (M+Na)+=(Calculated for $C_{22}H_{22}IN_5NaO_4S$, 602.0329) found, 602.0347.

3-Iodo-4-methoxy-N-(4-(piperazin-1-ylsulfonyl) phenyl)benzamide, TFA (61)

Synthesize using Method D and N-boc-piperazine as starting material. The Boc group was removed using 4 M HCl/dioxanes (3 equiv) stirred at rt for 1 h and concentrated to give desired product. $^1$H NMR (400 MHz, DMSO-d$_6$) δ 10.58 (s, 1H), 8.49 (s, 1H), 8.40 (d, J=2.2 Hz, 1H), 8.09-7.98 (m, 3H), 7.80-7.71 (m, 2H), 7.14 (d, J=8.8 Hz, 1H), 3.90 (s, 3H), 3.18 (t, J=5.1 Hz, 4H), and 3.06 (d, J=5.4 Hz, 4H); Retention Time=4.386 min; HRMS: m/z (M+H)+=(Calculated for $C_{18}H_{21}IN_3O_4S$, 502.0311) found, 502.0310.

4-Bromo-3-iodo-N-(4-((2-methylpiperazin-1-yl) sulfonyl)phenyl)benzamide, TFA (86)

Synthesize using Method D and tert-butyl-3-methylpiperazine-1-carboxylate as the starting material and 4-bromo-3-iodobenzoyl chloride as the acid chloride. After the amide formation the boc group was removed with 4 M HCl in dioxanes, at rt for 1 h. $^1$H NMR (400 MHz, DMSO-d$_6$): δ 10.72 (s, 1H), 8.67 (s, 2H), 8.45 (d, J=2.0 Hz, 1H), 8.03-7.96 (m, 2H), 7.93-7.79 (m, 2H), 4.13 (s, 1H), 3.29 (s, 3H), 3.27-3.16 (m, 1H), 3.14 (s, 2H), 2.93 (dd, J=4.3, and 13.0 Hz, 1H), 2.85-2.74 (m, 1H), and 1.09 (d, J=7.0 Hz, 2H); Retention Time=4.489 min; HRMS: m/z (M+Na)+=(Calculated for $C_{18}H_{19}BrIN_3NaO_3S$, 587.9248) found, 587.9237.

4-Bromo-3-iodo-N-(4-((3-methylpiperazin-1-yl) sulfonyl)phenyl)benzamide, TFA (83)

Synthesize using Method D and tert-butyl-2-methylpiperazine-1-carboxylate as the starting material and 4-bromo-3-iodobenzoyl chloride as the acid chloride. After the amide formation the boc group was removed with 4 M HCl in dioxanes, at rt for 1 h. $^1$H NMR (400 MHz, DMSO-d$_6$): δ 10.75 (s, 1H), 8.46 (dd, J=0.4, and 2.0 Hz, 1H), 8.06-8.01 (m, 2H), 7.92-7.84 (m, 2H), 7.80-7.74 (m, 2H), 3.71-3.54 (m, 2H), 3.42-3.23 (m, 2H), 3.17-3.04 (m, 2H), 2.56-2.48 (m, 1H), 2.33-2.27 (m, 1H), and 1.16 (d, J=6.5 Hz, 3H); Retention Time=4.503 min; HRMS: m/z (M+H)+=(Calculated for $C_{18}H_{20}BrIN_3O_3S$, 565.9429) found, 565.9406.

4-Bromo-3-iodo-N-(4-(piperazin-1-ylsulfonyl)phenyl)benzamide, HCl (121)

Synthesize using Method D and tert-butyl piperazine-1-carboxylate as the starting material and 4-bromo-3-iodobenzoyl chloride as the acid chloride. After the amide formation the boc group was removed with 4 M HCl in dioxanes, at rt for 1 hr. $^1$H NMR (400 MHz, DMSO-d$_6$) δ: 10.82 (s, 1H), 8.48 (t, J=1.2 Hz, 1H), 8.11-8.01 (m, 2H), 7.88 (d, J=1.2 Hz, 2H), 7.80-7.71 (m, 2H), and 3.19-3.06 (m, 8H); Retention Time=4.437 min; HRMS: m/z (M+H)+=(Calculated for $C_{17}H_{18}BrIN_3O_3S$, 551.9272) found, 551.929.

1-((4-(3-iodo-4-methoxybenzamido)phenyl)sulfonyl) piperazine-2-carboxamide, TFA (122)

Synthesize using Method D and 1-(tert-butyl) 3-methyl piperazine-1,3-dicarboxylate as the starting material, followed by reduction using a H-Cube Pro with a Pd/C Catcart at 50° C., and 50 Barr at 0.1 M in methanol and ethyl acetate (1/1). Once the reaction was complete the solvents were concentrated and the reaction was carried through without further purification. The amide coupling was done as previously described using 3-iodo-4-methoxybenzoyl chloride. The ester hydrolysis was done using 1 M LiOH/MeOH (1:1) heating to 70° C. for 1 hr. The carboxamide was done under standard conditions with EDC, HOBt, and ammonium hydroxide in DMF at rt overnight. When reaction was complete by LCMS it was poured into EtOAc and water. The organic layer was washed with water and brine, dried over Na$_2$SO$_4$, filtered, and concentrated. The crude boc protected piperazine was deprotected using 4 M HCl/dioxanes 1 h, at rt. This crude material was purified by reverse phase to give the desired material. $^1$H NMR (400 MHz DMSO-d$_6$): δ (10.57 (s, 1H), 8.39 (d, J=2.3 Hz, 1H), 8.15-7.88 (m, 3H), 7.93-7.75 (m, 2H), 7.72-7.45 (m, 2H), 7.14 (d, J=8.8 Hz, 1H), 4.59 (d, J=4.7 Hz, 1H), 3.90 (s, 4H), 3.53 (t, J=12.0 Hz, 2H), 3.19-2.94 (m, 2H), 2.81 (dd, J=5.0, and 13.4 Hz, 1H), and 2.72-2.55 (m, 1H); Retention Time=3.922 min; HRMS: m/z (M+H)+=(Calculated for $C_{19}H_{22}IN_4O_5S$, 545.035) found, 545.0344.

3,4-Dibromo-N-(4-((3-methylpiperazin-1-yl)sulfonyl)phenyl)benzamide, TFA (120)

Synthesize using Method D and tert-butyl-2-methylpiperazine-1-carboxylate as the starting material and 3,4-dibromobenzoyl chloride as the acid chloride. The dibromobenzoyl chloride was synthesized the same as previously described for the 3-iodo-4methyoxybenzolyl chloride. After the amide formation the boc group was removed with 4 M HCl in dioxanes, at rt for 1 h. $^1$H NMR (400 MHz DMSO-d$_6$): δ 10.78 (s, 1H), 8.31 (d, J=2.1 Hz, 1H), 8.07-7.99 (m, 2H), 7.95 (d, J=8.4 Hz, 1H), 7.86 (dd, J=2.1, and 8.4 Hz, 1H), 7.82-7.73 (m, 2H), 3.61 (t, J=12.9 Hz, 2H), 3.27 (s, 1H), 3.07 (t, J=12.0 Hz, 1H), 2.69-2.59 (m, 2H), 2.25 (t, J=11.4 Hz, 1H), and 1.13 (d, J=6.4 Hz, 3H); Retention Time=4.439 min; HRMS: m/z (M+H)+=(Calculated for $C_{18}H_{20}Br_2N_3O_3S$, 517.9548) found, 517.9569.

N-(4-((3,3-dimethylpiperazin-1-yl)sulfonyl)phenyl)-3-iodo-4-methoxybenzamide, TFA (123)

Synthesize using Method D and tert-butyl-2,2-dimethylpiperazine-1-carboxylate as the starting material. After the amide formation the boc group was removed with 4 M HCl in dioxanes, at rt for 1 hr. $^1$H NMR (400 MHz, DMSO-d$_6$) δ: 10.56 (s, 1H), 8.68 (s, 2H), 8.39 (d, J=2.2 Hz, 1H), 8.14-7.94 (m, 3H), 7.82-7.65 (m, 2H), 7.13 (d, J=8.7 Hz, 1H), 3.90 (s, 3H), 3.29-3.17 (m, 2H), 3.05 (s, 2H), 2.87 (s, 2H), and 1.29 (s, 6H); Retention Time=4.334 min; HRMS: m/z (M+H)+=(Calculated for $C_{18}H_{20}Br_2N_3O_3S$, 519.9548) found, 519.9569.

N-(4-((3,5-dimethylpiperazin-1-yl)sulfonyl)phenyl)-3-iodo-4-methoxybenzamide, TFA (125)

Synthesize using Method D and tert-butyl-2,2-dimethylpiperazine-1-carboxylate as the starting material. After the amide formation the boc group was removed with 4 M HCl in dioxanes, at rt for 1 h. $^1$H NMR (400 MHz, DMSO-d$_6$) δ: 10.56 (s, 1H), 9.03 (s, 1H), 8.39 (d, J=2.2 Hz, 1H), 8.07-7.98 (m, 3H), 7.80-7.73 (m, 2H), 7.13 (d, J=8.7 Hz, 1H), 4.05 (s, 1H), 3.90 (s, 3H), 3.76 (d, J=11.4 Hz, 2H), 3.13 (s, 1H), 2.14 (t, J=11.9 Hz, 2H), and 1.15 (d, J=6.4 Hz, 6H); Retention Time=4.371 min; HRMS: m/z (M+H)+=(Calculated for $C_{18}H_{20}Br_2N_3O_3S$, 519.9548) found, 519.9569.

N-(4-((1H-pyrrolo[2,3-c]pyridin-1-yl)sulfonyl)phenyl)-3-iodo-4-methoxybenzamide, TFA (14)

Synthesize using Method D and 1H-pyrrolo[2,3-c]pyridine as the starting material. $^1$H NMR (400 MHz, DMSO-d$_6$) δ 10.56 (s, 1H), 9.32 (d, J=1.0 Hz, 1H), 8.43 (d, J=5.6 Hz, 1H), 8.33 (d, J=2.3 Hz, 1H), 8.24 (d, J=3.5 Hz, 1H), 8.15-8.06 (m, 2H), 8.01-7.91 (m, 3H), 7.85 (d, J=5.7 Hz, 1H), 7.11 (d, J=8.8 Hz, 1H), 7.03 (dd, J=0.8, and 3.6 Hz, 1H), and 3.88 (s, 3H); Retention Time=4.671 min; HRMS: m/z (M+H)+=(Calculated for $C_{21}H_{17}IN_3O_4S$, 533.9979) found, 534.0000.

3-Iodo-4-methoxy-N-(4-(pyrrolidine-1-carbonyl)phenyl)benzamide (26)

(4-aminophenyl)(pyrrolidin-1-yl)methanone (0.06 g, 0.33 mmol), stirred in DCM (1.65 mL) with DIPEA (0.23 mL, 1.32 mmol) for 5 min before the addition of 3-iodo-4-methoxybenzoyl chloride (0.33 mL, 0.33 mmol) as a 1 M solution in DCM. This reaction stirred at rt for 18 h and was quenched with MeOH, concentrated, and was purified by reverse phase chromatography. $^1$H NMR (400 MHz, DMSO-d$_6$) δ 10.28 (s, 1H), 8.38 (d, J=2.2 Hz, 1H), 8.00 (dd, J=2.3, and 8.6 Hz, 1H), 7.83-7.74 (m, 2H), 7.54-7.46 (m, 2H), 7.12 (d, J=8.7 Hz, 1H), 3.89 (s, 3H), 3.58-3.16 (m, 4H), and 1.82 (dt, J=6.7, and 13.4 Hz, 4H); Retention Time=4.995 min; HRMS: m/z (M+H)+=(Calculated for $C_{19}H_{20}IN_2O_3$, 451.0513) found, 451.0521.

N-(4-(diethylcarbamoyl)phenyl)-3-iodo-4-methoxybenzamide (7)

Synthesize using Method A and 4-amino-N,N-diethylbenzamide. $^1$H NMR (400 MHz, DMSO-d$_6$) δ 10.26 (s, 1H), 8.38 (d, J=2.2 Hz, 1H), 8.01 (dd, J=2.2, and 8.6 Hz, 1H), 7.83-7.75 (m, 2H), 7.36-7.28 (m, 2H), 7.13 (d, J=8.8 Hz, 1H), 3.90 (s, 3H), 3.29-3.11 (m, 4H) and 1.07 (d, J=8.2 Hz, 6H); Retention Time=5.154 min; HRMS: m/z (M+H)+=(Calculated for $C_{19}H_{22}IN_2O_3$, 453.0670) found, 453.0674.

N-(4-((diethylamino)methyl)phenyl)-3-iodo-4-methoxybenzamide (43)

Tert-butyl (4-aminobenzyl)carbamate (73 mg, 0.33 mmol), DIPEA (0.23 mL, 1.32 mmol) was stirred in DCM (1.65 mL) for about 5 min before the addition of a 1 M solution of 3-iodo-4-methoxybenzoyl chloride (0.330 mL, 0.33 mmol) in DCM. The reaction mixture was allowed to stir for 18 h, poured into 10% citric acid solution, and extracted 3 times with DCM. The organic layers were combined and washed 1 time with saturated NaHCO$_3$ and one time with brine, dried over Na$_2$SO$_4$, filtered, and concentrated under reduced pressure. This crude material was used as is in the next reaction without further purification. The crude material was treated with 4 M HCl in dioxanes and stir at rt for 1 hr and concentrated, titrated with diethyl ether and dried under reduced pressure to give the product as an HCl. This product was used as is in the next reaction. N-(4-(aminomethyl)phenyl)-3-iodo-4-methoxybenzamide, HCl (0.14 g, 0.33 mmol), Cs$_2$CO$_3$ (0.11 g, 0.33 mmol), and iodoethane (0.07 mL, 0.83 mmol) were stirred in DMF (2.0 mL) overnight. The crude mixture was purified on reverse phase chromatography to give the desired compound with an overall yield of 14% over 3 steps. $^1$H NMR (400 MHz, DMSO-d$_6$) δ 10.29 (s, 1H), 8.37 (d, J=2.2 Hz, 1H), 8.00 (dd, J=2.2, and 8.6 Hz, 1H), 7.92-7.72 (m, 2H), 7.58-7.35 (m, 2H), 7.12 (d, J=8.7 Hz, 1H), 4.24 (d, J=5.3 Hz, 2H), 3.89 (s, 3H), 3.04 (tt, J=5.8, and 11.8 Hz, 4H), and 1.20 (t, J=7.2 Hz, 6H); Retention Time=4.038 min; HRMS: m/z (M+Na)+=(Calculated for $C_{19}H_{23}IN_2NaO_2$, 461.0696) found, 461.0771.

N-(4-bromo-3-iodophenyl)-4-((2-methylpiperidin-1-yl)sulfonyl)benzamide (127)

4-(Chlorosulfonyl)benzoic acid (0.50 g, 2.27 mmol), 2-methylpiperidine (0.53 mL, 4.53 mmol), TEA (0.32 mL, 2.27 mmol), was stirred in DCM (11.30 mL) overnight. The reaction was diluted with DCM and washed with 1 N HCl. The acidic layer was extracted 2×'s with DCM, all organic layers were combine and washed with NaHCO$_3$, and brine. The organic layer was dried over Na$_2$SO$_4$, filtered, and concentrated to give an oil which was used as is in the next reaction. 4-((2-methylpiperidin-1-yl)sulfonyl)benzoic acid (0.12 g, 0.41 mmol), 4-bromo-3-iodoaniline (0.12 g, 0.41 mmol), TEA (0.17 mL, 1.23 mmol), and propane phosphonic acid anhydride (0.39 mL, 0.61 mmol) in DMF (2.1 mL) was heated to 70° C. for 24 hr. The reaction was cooled to rt, poured into EtOAc and washed with 1 N HCl, bicarb, brine, dried over Na$_2$SO$_4$, filtered, concentrated, and turned in for purification and testing. $^1$H NMR (400 MHz, DMSO-d$_6$): δ 10.58 (s, 1H), 8.41 (d, J=2.4 Hz, 1H), 8.14-8.05 (m, 2H), 7.98-7.90 (m, 2H), 7.78-7.65 (m, 2H), 4.15 (tq, J=3.5, and 7.1 Hz, 1H), 3.64 (dd, J=4.0, and 13.5 Hz, 1H), 2.99 (td, J=2.6, and 13.1 Hz, 1H), 1.57-1.42 (m, 2H), 1.40 (dd, J=3.8, and 7.8 Hz, 3H), 1.24-1.09 (m, 1H), and 1.00 (d, J=6.9 Hz, 3H); Retention Time=5.514 min; HRMS: m/z (M+Na)+=(Calculated for $C_{19}H_{20}BrIN_2NaO_3S$, 586.9296) found, 586.9271.

N-(3-iodo-4-methoxyphenyl)-4-((2-methylpiperidin-1-yl)sulfonyl)benzamide (128)

4-((2-methylpiperidin-1-yl)sulfonyl)benzoic acid (0.05 g, 0.18 mmol), DIPEA (0.10 mL, 0.529 mmol), HOBt (8.00 mg, 0.05 mmol), and 3-iodo-4-methoxyaniline (0.05 g, 0.21 mmol), and HATU (0.10 g, 0.27 mmol) was stirred in DMF (1.00 mL) for 3 h at rt. The reaction was poured into EtOAc and washed with 1 N HCl, 1 N NaOH, and 2×'s with brine. The solution was dried over Na$_2$SO$_4$, filtered, concentrated, and sent to purification. $^1$H NMR (400 MHz, DMSO-d$_6$): δ 10.37 (s, 1H), 8.20 (d, J=2.5 Hz, 1H), 8.11-8.04 (m, 2H), 7.95-7.88 (m, 2H), 7.72 (dd, J=2.5, and 8.9 Hz, 1H), 7.00 (d, J=9.0 Hz, 1H), 4.12 (dq, J=3.7, and 7.1 Hz, 1H), 3.78 (s, 3H), 3.63 (dd, J=4.3, and 14.7, Hz, 1H), 2.97 (td, J=2.6, and 13.1, Hz, 1H), 1.60-1.30 (m, 5H), 1.29-1.03 (m, 1H), and 0.98 (d, J=6.9 Hz, 3H); Retention Time=6.049 min; HRMS: m/z (M+Na)+=(Calculated for $C_{20}H_{23}IN_2NaO_4S$, 537.0315) found, 537.0318.

N-(3-iodo-4-methoxyphenyl)-4-((3-methylthiomorpholino)sulfonyl)benzamide (126)

Follow the procedure for N-(4-bromo-3-iodophenyl)-4-((2-methylpiperidin-1-yl)sulfonyl)benzamide (127) using 3-methylthiomorpholine instead of 2-methylpiperidine. $^1$H NMR (400 MHz, DMSO-d$_6$): δ 10.40 (s, 1H), 8.22 (d, J=2.5 Hz, 1H), 8.15-8.07 (m, 2H), 7.98-7.90 (m, 2H), 7.74 (dd, J=2.5, and 8.9 Hz, 1H), 7.01 (d, J=9.0 Hz, 1H), 4.34 (qt, J=2.9, and 6.6 Hz, 1H), 3.93 (dt, J=3.1, and 14.0 Hz, 1H), 3.80 (s, 3H), 3.18 (ddd, J=4.1, 10.6, and 14.3, Hz, 1H), 2.82-2.73 (m, 1H), 2.49-2.33 (m, 3H), and 1.16-1.09 (m, 3H); Retention Time=5.718 min; HRMS: m/z (M+H)+= (Calculated for $C_{19}H_{22}IN_2O_4S_2$, 533.0060) found, 533.0065.

N-(4-bromo-3-iodophenyl)-4-((3-ethylmorpholino)sulfonyl)benzamide (129)

Follow synthesis for N-(4-bromo-3-iodophenyl)-4-((2-methylpiperidin-1-yl)sulfonyl)benzamide (127) using 3-ethyl morpholine as the starting material. For the amide formation use the following procedure. 4-((3-Ethylmorpholino)sulfonyl)benzoic acid (0.10 g, 0.334 mmol), DIPEA (0.18 mL, 1.00 mmol), HOBt (0.02 g, 0.10 mmol), and 4-bromo-3-iodoaniline (0.12 g, 0.40 mmol) were all stirred at rt before HATU (0.19 g, 0.50 mmol) was added. The reaction was stirred at rt for 4 hr and quenched with water and EtOAc. Wash EtOAc layer with water and brine, dry over $Na_2SO_4$, filter, concentrate and turn in for purification. $^1$H NMR (400 MHz DMSO-$d_6$): δ 10.59 (s, 1H), 8.40 (d, J=2.4 Hz, 1H), 8.14-8.06 (m, 2H), 8.02-7.94 (m, 2H), 7.77-7.64 (m, 2H), 3.68-3.49 (m, 4H), 3.20 (ddd, J=3.4, 12.2, and 14.1 Hz, 1H), 3.17-3.07 (m, 1H), 2.99 (td, J=3.0, and 11.8 Hz, 1H), 1.64-1.48 (m, 2H), and 0.80 (t, J=7.4 Hz, 3H); Retention Time=6.215 min; HRMS: m/z (M+Na)+= (Calculated for $C_{19}H_{20}BrIN_2NaO_4S$, 602.9245) found, 602.9246.

4-((3-Ethylmorpholino)sulfonyl)-N-(3-iodo-4-methoxyphenyl)benzamide (132)

Follow synthesis for N-(4-bromo-3-iodophenyl)-4-((3-ethylmorpholino)sulfonyl)benzamide (127) using 3-iodo-4-methoxyaniline as the starting material for the amide coupling. $^1$H NMR (400 MHz, DMSO-$d_6$): δ 10.39 (s, 1H), 8.21 (d, J=2.5 Hz, 1H), 8.14-8.06 (m, 2H), 8.01-7.93 (m, 2H), 7.73 (dd, J=2.6, and 8.9 Hz, 1H), 7.00 (d, J=9.0 Hz, 1H), 3.79 (s, 3H), 3.69-3.47 (m, 4H), 3.26-3.06 (m, 2H), 2.99 (td, J=3.0, and 11.8 Hz, 1H), 1.65-1.46 (m, 2H), and 0.80 (t, J=7.4 Hz, 3H); Retention Time=5.610 min; HRMS: m/z (M+H)+=(Calculated for $C_{20}H_{24}IN_2O_5S$, 531.0445) found, 531.0442.

(+)-(S)-3-iodo-4-methoxy-N-(4-((2-methylpiperazin-1-yl)sulfonyl)phenyl)benzamide, HCl (130)

Positive enantiomer $^1$H NMR (400 MHz, DMSO-$d_6$): δ 10.47 (s, 1H), 8.39 (d, J=2.2 Hz, 1H), 8.05-7.91 (m, 3H), 7.79-7.71 (m, 2H), 7.13 (d, J=8.8 Hz, 1H), 4.12-4.04 (m, 1H), 3.90 (s, 3H), 3.61-3.52 (m, 1H), 2.93 (td, J=2.6, and 13.0, Hz, 1H), 1.54-1.36 (m, 2H), 1.38 (s, 3H), 1.25-1.10 (m, 1H), and 0.98 (d, J=6.9 Hz, 3H); Retention Time=6.152 min; HRMS: m/z (M+H)+=(Calculated for $C_{20}H_{24}IN_2O_4S$ 515.0496) found, 515.0498. The enantiomers were separated using CHIRALPAK AS column, at 35 mL/min, isocratic MeOH, to give ee's of >99% for the positive, and 98.7% of the negative compound.

(−)-(R)-3-iodo-4-methoxy-N-(4-((2-methylpiperazin-1-yl)sulfonyl)phenyl)benzamide, HCl (131)

1st negative enantiomer $^1$H NMR (DMSO-$d_6$ 400 MHz): δ 10.47 (s, 1H), 8.39 (d, J=2.2 Hz, 1H), 8.05-7.91 (m, 3H), 7.79-7.71 (m, 2H), 7.13 (d, J=8.8 Hz, 1H), 4.12-4.04 (m, 1H), 3.90 (s, 3H), 3.61-3.52 (m, 1H), 2.93 (td, J=2.6, and 13.0, Hz, 1H), 1.54-1.36 (m, 2H), 1.38 (s, 3H), 1.25-1.10 (m, 1H), and 0.98 (d, J=6.9 Hz, 3H); Retention Time=6.157 min; HRMS: m/z (M+H)+=(Calculated for $C_{20}H24IN_2O_4S$, 515.0496) found, 515.0516. The enantiomers were separated using CHIRALPAK AS column, at 35 mL/min, isocratic MeOH, to give ee's of >99% for the positive, and 98.7% of the negative compound.

(S)-4-((4-(3-iodo-4-methoxybenzamido)phenyl)sulfonyl)thiomorpholine-3-carboxamide (133)

$1^{st}$ negative enantiomer $^1$H NMR (400 MHz, DMSO-$d_6$): δ 10.49 (s, 1H), 8.39 (d, J=2.2 Hz, 1H), 8.05-7.92 (m, 3H), 7.83-7.74 (m, 2H), 7.26 (d, J=12.1 Hz, 2H), 7.14 (d, J=8.8 Hz, 1H), 4.64 (t, J=3.4 Hz, 1H), 3.99-3.91 (m, 1H), 3.90 (s, 3H), 3.51 (ddd, J=5.9, 9.2, and 14.5 Hz, 1H), 2.93 (dd, J=2.9, and 14.1 Hz, 1H), 2.59 (dd, J=4.1, and 13.9 Hz, 1H), and 2.41-2.33 (m, 2H); Retention Time=4.930 min; HRMS: m/z (M+H)+=(Calculated for $C_{19}H_{21}IN_3O_5S_2$, 561.9962) found, 561.9954. The enantiomers were separated using CHIRALPAK. IA Mobile Phase: MeCN/IPA 80:20, flow rate: 35 mL/min; 1st_neg: ee>99%, 2nd_pos: ee 93.9%.

(R)-4-((4-(3-iodo-4-methoxybenzamido)phenyl)sulfonyl)thiomorpholine-3-carboxamide (134)

$2^{nd}$ positive enantiomer $^1$H NMR (400 MHz, DMSO-$d_6$): δ 10.49 (s, 1H), 8.39 (d, J=2.2 Hz, 1H), 8.05-7.92 (m, 3H), 7.83-7.74 (m, 2H), 7.26 (d, J=12.1 Hz, 2H), 7.14 (d, J=8.8 Hz, 1H), 4.64 (t, J=3.4 Hz, 1H), 3.99-3.91 (m, 1H), 3.90 (s, 3H), 3.51 (ddd, J=5.9, 9.2, and 14.5 Hz, 1H), 2.93 (dd, J=2.8, and 14.1 Hz, 1H), 2.59 (dd, J=4.1, and 13.9 Hz, 1H), and 2.41-2.33 (m, 2H); Retention Time=4.928 min; HRMS: m/z (M+H)+=(Calculated for $C_{19}H_{21}IN_3O_5S_2$, 561.9962) found, 561.9981.

Example 2

Figure 1B:
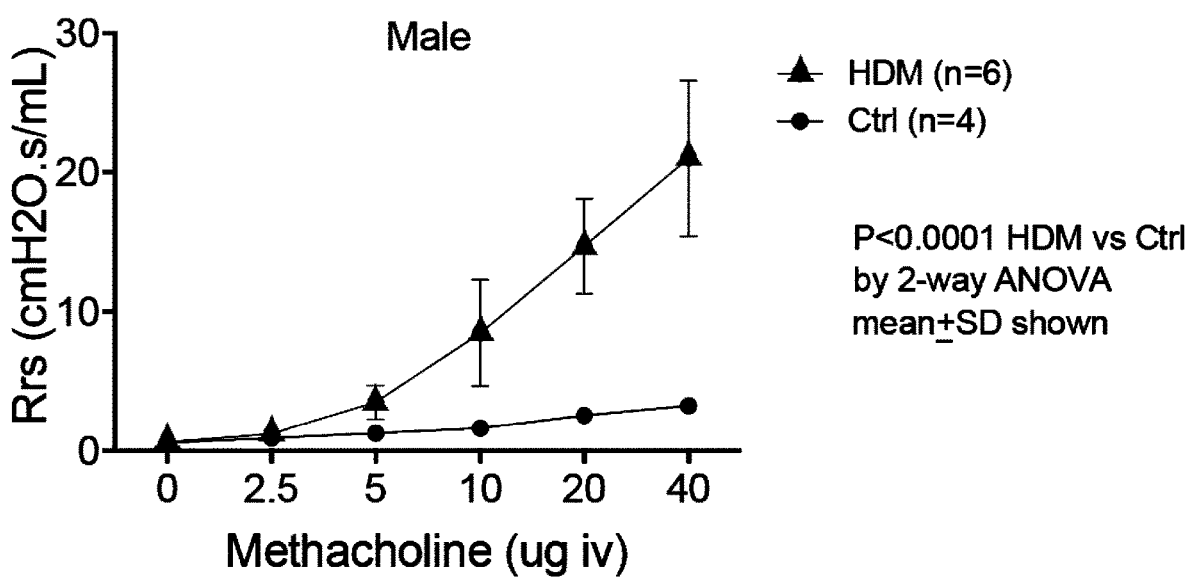
Figure 2:
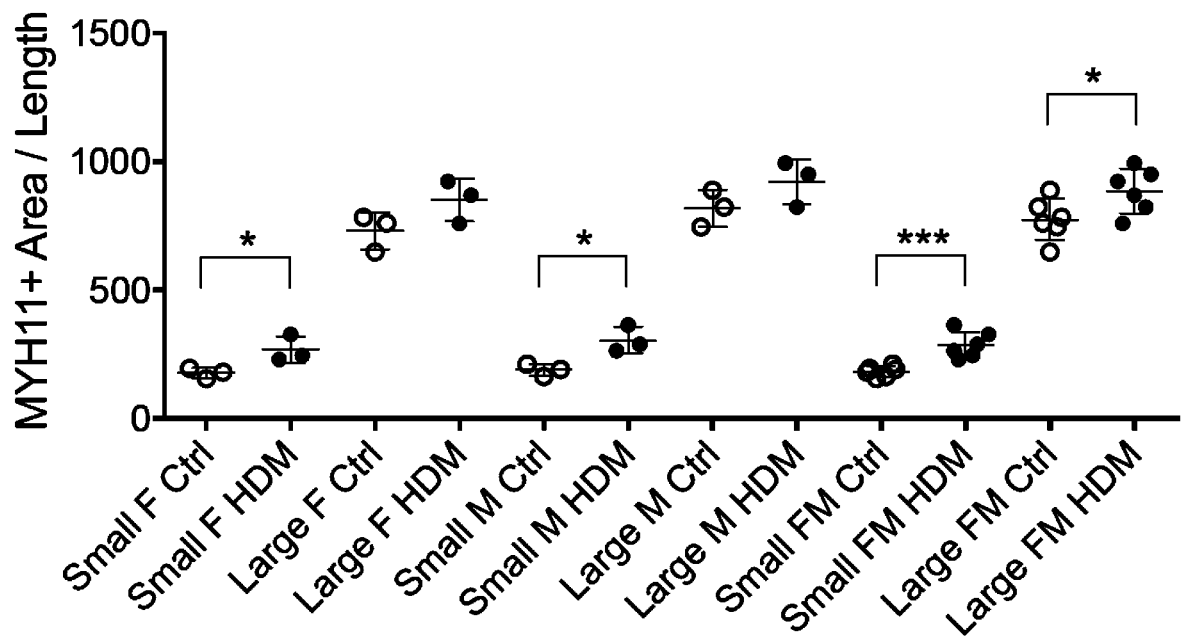
FIG. 2. Demonstration of airway remodeling in HDM-treated mice. Length-normalized smooth muscle myosin heavy-chain immunostain-positive (MYH11) area was significantly increased in the small airways by 51.6% in female (F) and by 61.9% in male (M) HDM-treated mice, compared with control mice. When both sexes (FM) were considered together, large airways of HDM-treated mice also demonstrated a significant increase of 14.5% in MYH11+ area/epithelial length (and the same trend was seen in both sexes individually). Furthermore, three-way analysis of variance (Ctrl vs HDM, Female vs Male, Small vs Large Airways) confirmed that the HDM influence on airway remodeling was significant at $P=0.0007$.

Validate Robustness of HDM Sensitization/Challenge and IL33-Alone Mouse Models of Airway Remodeling and their Suitability for Remodilin Efficacy Testing, in Each Sex A mouse model of acute allergic asthma was used in which mice were sensitized with house dust mite (HDM) extracts. Airway constrictor hyperresponsiveness was defined as significantly greater increases in respiratory system resistance during methacholine challenge. As depicted in FIGS. 1A and 1B, male and female Balb/c mice treated with HDM were subjected to methacholine challenge. Both sexes exhibited dose-response respiratory system resistance (Rrs) and airway constrictor hyperresponsiveness. The HDM model demonstrated statistically significant airway constrictor hyperresponsiveness in both sexes following challenge with i.v. methacholine. The area under the curve increased by at least 3.6-fold in each sex.

Example 3

Demonstration of Airway Remodeling in HDM-Treated Mice

Length-normalized smooth muscle myosin heavy-chain (MYH11) immunoreactive airway smooth muscle area was significantly increased in the small airways by 51.6% in female (F) and by 61.9% in male (M) HDM-treated mice, compared with control mice. When both sexes (FM) were considered together, large airways of HDM-treated mice also demonstrated a significant increase of 14.5% in MYH11+area/epithelial length (and the same trend was seen in both sexes individually). Furthermore, three-way analysis of variance (Ctrl vs HDM, Female vs Male, Small vs Large Airways) confirmed that the HDM influence on airway remodeling was significant at P=0.0007.

The HDM model demonstrated statistically significant increases in smooth muscle myosin-positive area normalized to epithelial length in both sexes. This airway remodeling was greater in small airways (average increase of 57.0%), but was also present in the large airways (average increase of 14.5%). Thus, significant and substantial airway constrictor hyperresponsiveness and airway remodeling have been validated in the HDM model.

Example 4

Pharmacokinetic Evaluations of Remodilins

Studies were performed to characterize plasma pharmacokinetics (PK) and tissue distribution (liver, lung, thyroid) of 5 potential lead candidates in male C57Bl/6 mice receiving single oral doses of 10 mg/kg or 50 mg/kg. As shown in FIGS. 3A-3E, three of the five remodilins (remodilin 61, remodilin 83, and remodilin 86) are found in higher concentrations in lung (open squares) than in plasma (filled-in circle), liver (open circles), or thyroid (upside-down, filled-in triangles) after oral administration. For >8 hours after a single oral dose of 10 or 50 mg/kg, the concentration of each of the three remodilins in the lung substantially exceeds the 3 µM concentration (dotted horizontal line in all panels in FIGS. 3A-3E) that have been shown to be effective in in vitro studies (in vitro efficacy defined as reduced MYH11 or smooth muscle alpha actin accumulation in cultured HASM cells).

The higher concentration of remodilins in the lung after oral administration is highly desirable, as it mirrors the expected advantage of aerosol delivery (increased exposure at the target tissue with the possibility of reduced systemic exposure and resulting off-target effects).

Example 5

Figure 4A:
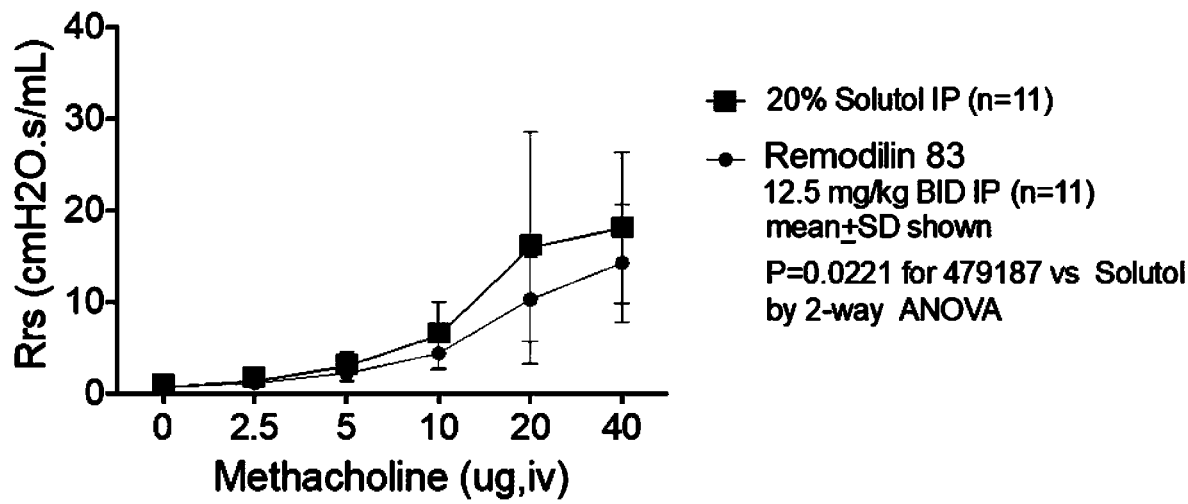
FIGS. 4A-4B. Effect of remodilin treatment (remodilin 83, 12.5 mg/kg BID IP) on airway constrictor hyperresponsiveness and remodeling induced by house dust mite (HDM) exposure in female Balb/c mice.
Figure 4B:
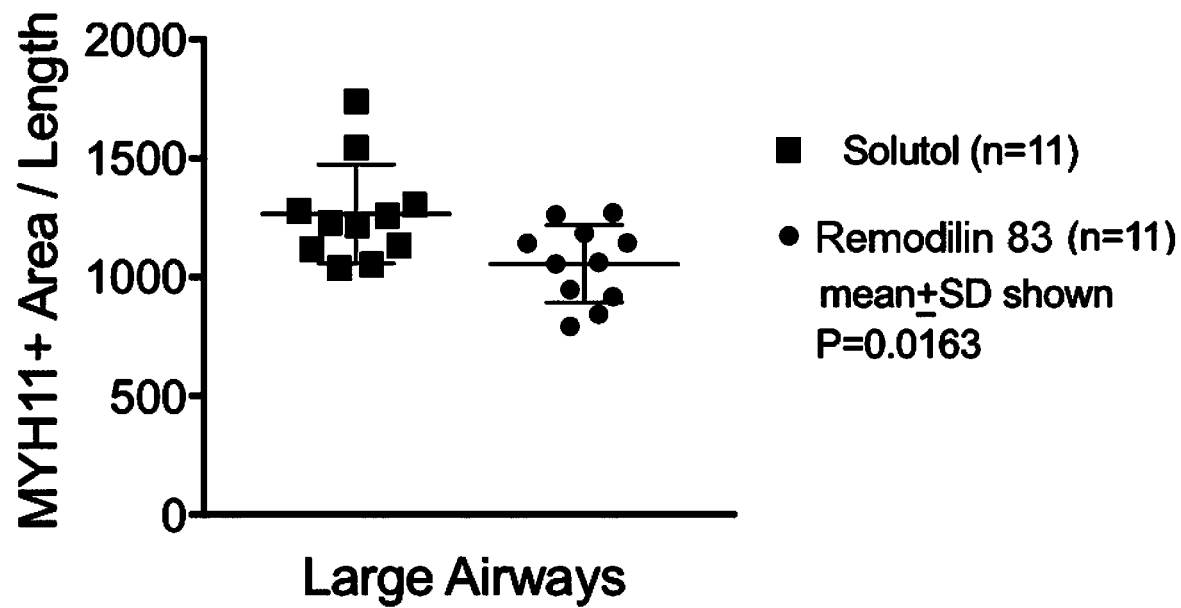
Figure 5:
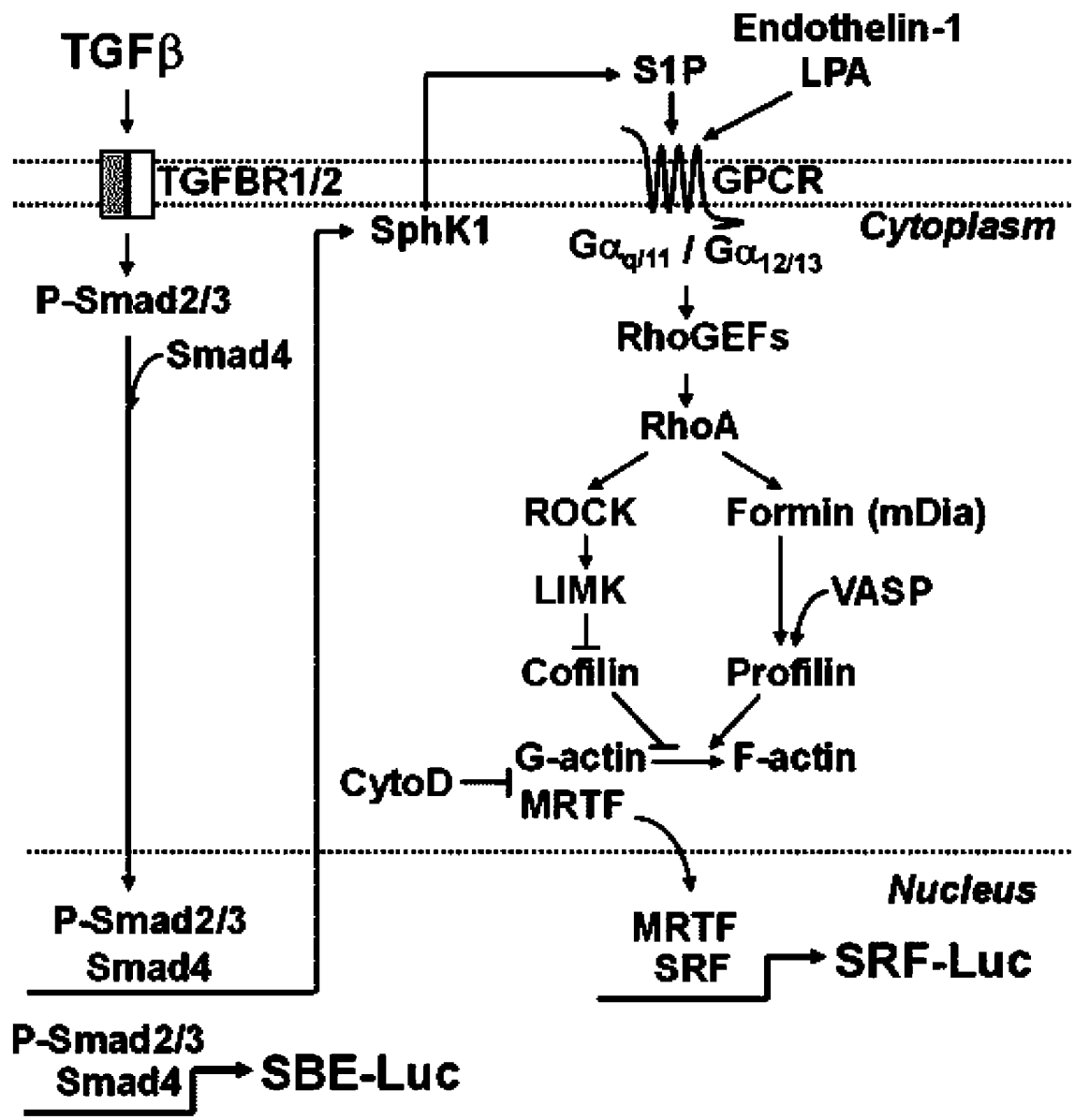
FIG. 5. RhoA signaling pathway that includes Smad and serum response factor (SRF). Remodilins act downstream of Smad signaling, which remains intact even though TGFβ-induced SRF activation is blocked, suggesting that remodilins act along the RhoA pathway.

Effect of Remodilin on HDM-Induced Airway Constrictor Hyperresponsiveness and Airway Remodeling As depicted in FIG. 4A, twice-daily intraperitoneal administration of remodilins (12.5 mg/kg) was evaluated. Remodilin 83 significantly blunted development of airway constrictor hyperresponsiveness in the HDM model. Remodilin 83 significantly lowered MYH11 immunostain-positive airway smooth muscle area normalized to epithelial length compared with 20% Solutol (vehicle), in the large airways.

Example 6

Figure 6A:
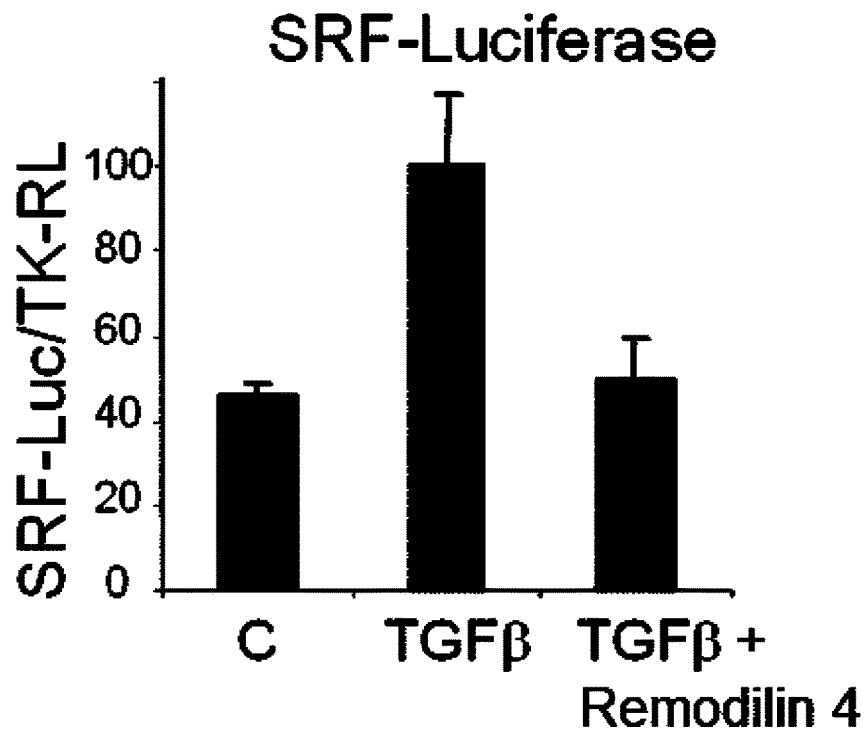
FIGS. 6A-6B. Remodilins inhibit myofibroblast transformation. Remodilin 4 inhibits TGFβ-stimulated serum response factor (SRF) activation (FIG. 6B) but not Smad signaling (FIG. 6A), as determined using luciferase reporter assays.
Figure 6B:
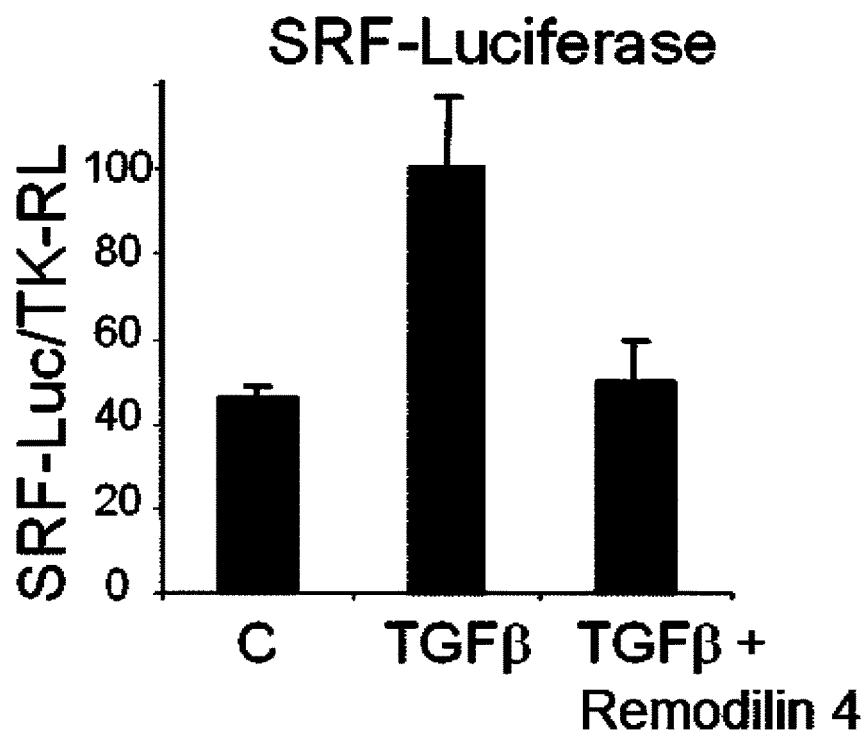
Figure 7:
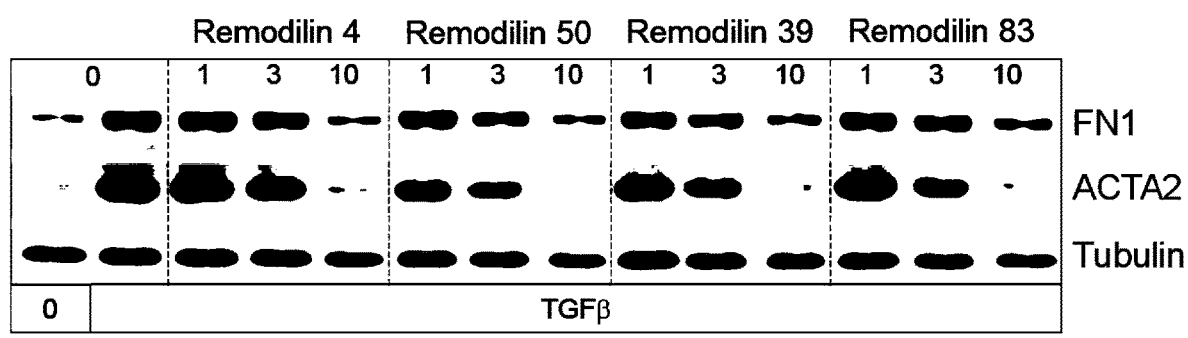
FIG. 7. Dose-response effect of remodelins on smooth muscle α-actin (ACTA2) or fibronectin-1 (FN1) protein expression (markers of MFT). Serum deprived human lung-derived fibroblasts were treated with 1 ng/mL TGFβ1 (or not, left lane) and 0, 1, 3, or 10 µM remodilin for 2 d. Four remodilins inhibited smooth muscle ACTA2 and fibronectin-1 (FN1) protein expression in dose-dependent fashion.

Effect of TGFβ-Induced Transformation of Human Lung Fibroblasts into Myofibroblasts It is well-established that myofibroblast transformation (MFT) is a critical step in the development of pulmonafy fibrisos. Luciferase reporter studies show that remodilins do not affect TGFβ-induced Smad activation (FIG. 6B, an initial step in TGFβ signaling), but they do inhibit the more downstream TGFβ-stimulated serum response factor (SRF) activation (FIG. 6A). Remodilins act downstream of Smad signaling (SBE=Smad binding element), which remains intact even though TGFβ-induced SRF activation is blocked, suggesting that remodilins act along the RhoA pathway. Maintenance of Smad signaling can preserve other beneficial effects of TGFβ. As depicted in FIG. 7, four remodilins inhibited smooth muscle ACTA2 and fibronectin-1 (FN1) protein expression (markers of MFT) in dose-dependent fashion.

Example 7

Inhibition of Bleomycin-Induced Lung Fibrosis

Figure 8A:
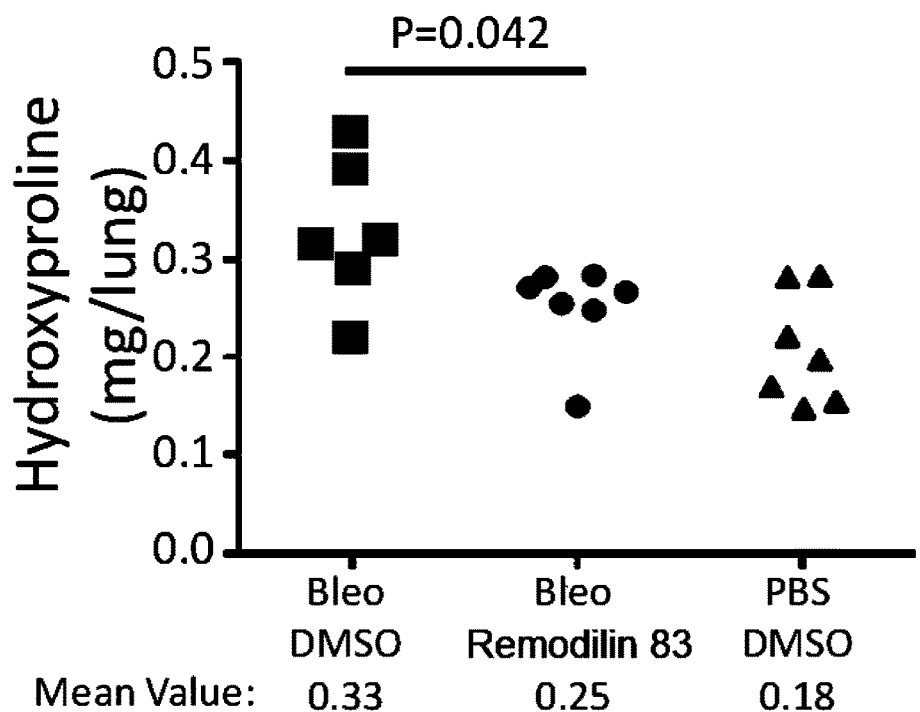
FIGS. 8A-8B. Treatment with remodilin 83 (25 mg/kg QD IP) reduced pulmonary fibrosis in bleomycin-treated mice. Remodilin or vehicle (DMSO) was given on days 7-21 after i.t. bleomycin (1 U/kg). Both lung hydroxyproline (FIG. 8A) and collagen levels (FIG. 8B) were lower in remodilin 83-treated mice than in control mice.
Figure 8B:
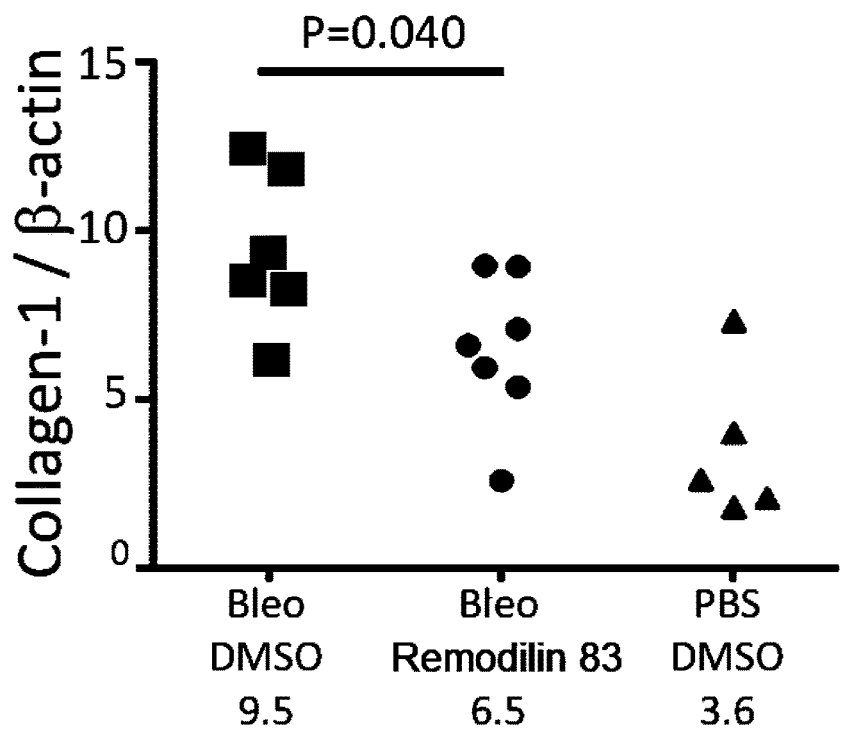
Figure 9A:
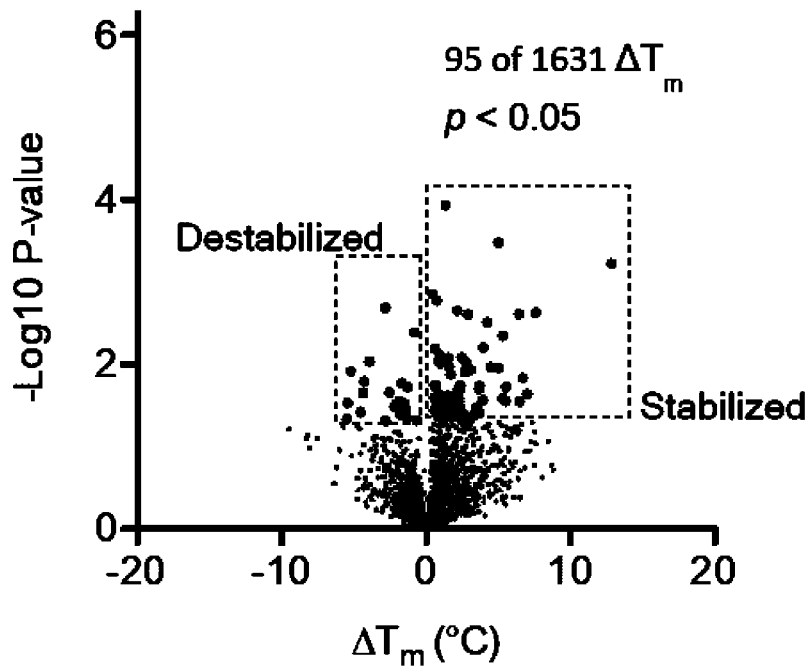
FIGS. 9A-9B. Hotspot thermal profiling for investigation of remodilin molecular targets. "Volcano" plots demonstrate the distributions of melting temperature change, and their log p-values, induced by incubation with remodilins 39 (FIG. 9A) and 83 (FIG. 9B).
Figure 9B:
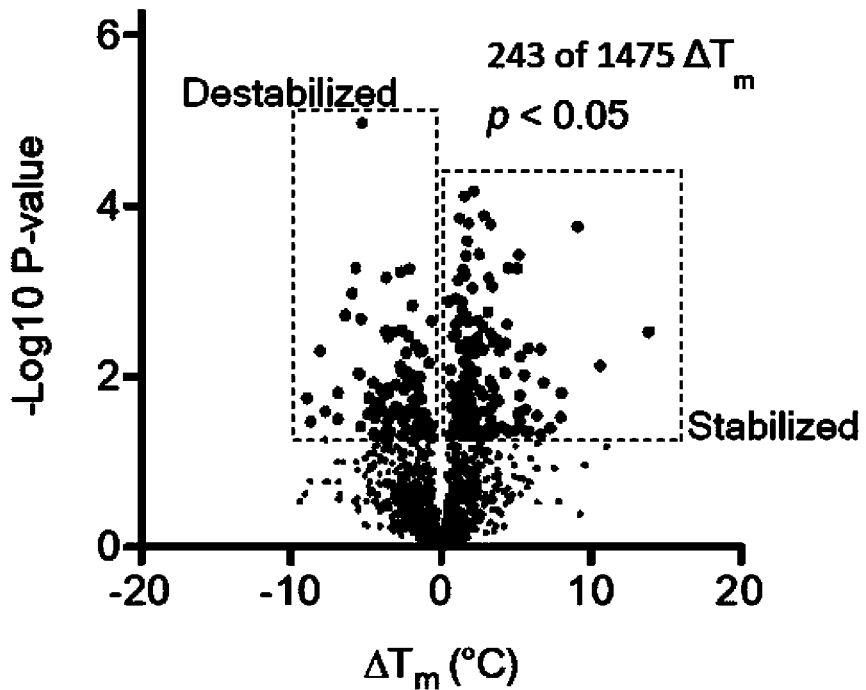

The inhibitory activity of remodilin 83 against bleomycin-induced lung fibrosis in mice was confirmed. Both lung hydroxyproline (FIG. 8A) and collagen levels (FIG. 8B) were lower in remodilin 83-treated mice (systemically-administered) than in control mice.

The data demonstrate that administration of remodilins attenuate airway constrictor hyperresponsiveness and airway remodeling in HDM mice. Remodilins were also shown to inhibit bleomycin-induced lung fibrosis and transformation of human lung fibroblasts into myofibroblasts. These lung diseases are amenable to inhalation therapy, which offers organ-selective drug targeting and reduced systemic exposure. Many millions of asthma patients are treated routinely with inhalation therapy, and inhalation therapy of remodilins is an attractive approach for treatment of the lung diseases described herein. For treatment of fibrotic diseases outside the lung, systemic or topical delivery may be the preferred approach.

Example 8

Identifying the Molecular Binding Partners of Remodilins

The molecular targets of remodelins was investigated using hotspot thermal profiling (HTP) chemoproteomic methods. Primary human lung fibroblasts at low passage were grown to 90% confluence, then serum starved for 24 hrs. Cells were treated for 3 hours with remodilin 39 (10 µM), remodilin 83 (10 µM), or DMSO (control diluent for remodilins), then washed, resuspended in DPBS with protease inhibitors, and aliquots heated for 3 min to 37° C. to 67° C. Cells were returned for 3 min to 25° C., then lysed by freeze-thaw in liquid $N_2$ thrice, centrifuged at 17,000 g for 10 mins to remove debris, and supernatant collected.

Proteins in each supernatant were denatured, reduced, and alkylated, digested overnight with trypsin, desalted, and labeled with a tandem mass tag (TMT). TMT-labeled aliquots were combined and again desalted. The resulting peptides were analyzed using LC-MS/MS, using ProLucid to identify and quantify each species. Thermal denaturation curve fit analysis was performed using R, and the melting temperatures of each protein compared across the 3 treatments, using 3-4 mass spec injections per treatment. Table 1 summarizes unique proteins identified (3486 in all) for each treatment, the number shared between each remodilin and DMSO treatment, and the number for which differences in melting temperature (ΔTm) could be determined.

TABLE 1

Potential Molecular Targe Proteins Identified

| Treatment | # MS injections | Proteins detected | Proteins detected in DMSO and remodilin | Proteins for which ΔTm was determined |
|---|---|---|---|---|
| DMSO | 4 | 2955 | | |
| Remodilin 39 | 4 | 2819 | 2445 | 1631 |
| Remodilin 83 | 3 | 2443 | 2195 | 1475 |

Of the proteins significantly stabilized or significantly destabilized by remodilin treatment, 28 were significantly affected by both remodilin 39 and remodilin 83 (FIGS. 10A-10B). Starred Protein IDs indicate those proteins that exhibited significant ΔTm shifts of 2° C. or greater. These include multiple potential targets that could modulate myofibroblast transformation and pulmonary fibrosis.

Remodilins represent an entirely new class of therapeutics that could prevent or potentially reverse lung scarring in IPF. No currently available medication blocks myofibroblast transformation, a "checkpoint" step in the pathogenesis of IPF. Currently available IPF drugs offer modest clinical benefit, and remodilins could be added to existing regimens, as they likely operate through different mechanisms of action.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A composition comprising a compound of

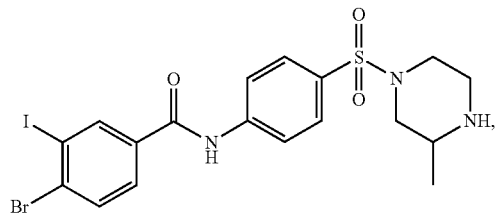 [SMILES: CC1CN(S(=O)(=O)c2ccc(NC(=O)c3ccc(Br)c(I)c3)cc2)CCN1]

or a salt, enantiomer, or diastereomer thereof.

2. The composition of claim 1, wherein the composition is formulated to be administered orally, intraadiposally, intraarterially, intraarticularly, intracranially, intradermally, intralesionally, intramuscularly, intraperitoneally, intrapleurally, intranasally, intraocularally, intrapericardially, intraprostaticaly, intrarectally, intrathecally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof.

3. The composition of claim 1, further comprising a second compound of Formula 1:

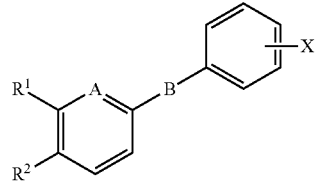

Formula I where:
A is —CH— or —N—;
B is —C(O)—NH—, —NH—C(O)—, —CH$_2$—NH—, or —C(NH)—NH—;
X is —(Y)—NR$^3$R$^4$;
Y is —SO$_2$-, —C(O)—, or —(CH$_2$)—;
R$^1$ and R$^2$ are each independently hydroxyl, substituted or unsubstituted alkyl, substituted or unsubstituted alkynyl, alkoxy, halide, nitrile, amine, acylamine, substituted or unsubstituted aryl, 4-6 member carbocycle, substituted or unsubstituted heterocycle, and R$^3$ and R$^4$ join to form a carbocycle or heterocycle;
or a salt, enantiomer, or diastereomer thereof.

* * * * *

UNITED STATES PATENT AND TRADEMARK OFFICE
CERTIFICATE OF CORRECTION

PATENT NO. : 12,281,060 B2  
APPLICATION NO. : 17/594086  
DATED : April 22, 2025  
INVENTOR(S) : Julian Solway et al.

Page 1 of 1

It is certified that error appears in the above-identified patent and that said Letters Patent is hereby corrected as shown below:

On the Title Page

Item (71) Applicants:
Delete "REGENTS OF THE UNIVERSITY OF MINNESOTA, Minneapolis, MN (US); THE TRUSTEES OF PURDUE UNIVERSITY, Lafayette, IN (US)".

Signed and Sealed this  
Fifteenth Day of July, 2025

Coke Morgan Stewart  
*Acting Director of the United States Patent and Trademark Office*